US011196008B2

(12) United States Patent
Park et al.

(10) Patent No.: US 11,196,008 B2
(45) Date of Patent: Dec. 7, 2021

(54) COMPOUND FOR ORGANIC ELECTRIC ELEMENT, ORGANIC ELECTRIC ELEMENT USING SAME, AND ELECTRONIC APPARATUS THEREOF

(71) Applicant: DUK SAN NEOLUX CO., LTD., Cheonan-si (KR)

(72) Inventors: Jung Cheol Park, Suwon-si (KR); Yeon Hee Choi, Cheonan-si (KR); Mun Jae Lee, Cheonan-si (KR); Soung Yun Mun, Cheonan-si (KR); Ki Won Kim, Suwon-si (KR); Nam Jin Park, Cheonan-si (KR); Sun Pil Hwang, Ansan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 15/739,611

(22) PCT Filed: Apr. 27, 2016

(86) PCT No.: PCT/KR2016/004401
§ 371 (c)(1),
(2) Date: Dec. 22, 2017

(87) PCT Pub. No.: WO2016/208862
PCT Pub. Date: Dec. 29, 2016

(65) Prior Publication Data
US 2018/0226585 A1    Aug. 9, 2018

(30) Foreign Application Priority Data
Jun. 25, 2015 (KR) .................... 10-2015-0009075

(51) Int. Cl.
H01L 51/54        (2006.01)
H01L 51/00        (2006.01)
C07D 307/91       (2006.01)
C09K 11/06        (2006.01)
C07F 7/08         (2006.01)
C07D 405/04       (2006.01)
C07D 409/04       (2006.01)
H01L 27/32        (2006.01)
H01L 51/50        (2006.01)

(52) U.S. Cl.
CPC ........ *H01L 51/0061* (2013.01); *C07D 307/91* (2013.01); *C07D 405/04* (2013.01); *C07D 409/04* (2013.01); *C07F 7/0812* (2013.01); *C07F 7/0814* (2013.01); *C09K 11/06* (2013.01); *H01L 51/006* (2013.01); *H01L 51/0073* (2013.01); *H01L 51/0074* (2013.01); *H01L 27/32* (2013.01); *H01L 51/001* (2013.01); *H01L 51/0052* (2013.01); *H01L 51/0058* (2013.01); *H01L 51/0094* (2013.01); *H01L 51/5012* (2013.01); *H01L 51/5056* (2013.01); *H01L 51/5088* (2013.01)

(58) Field of Classification Search
CPC .. C07D 307/91; C07D 409/00; C07D 409/02; C07D 409/04; C07D 405/00; C07D 405/02; C07D 405/04; C07F 7/0812; C07F 7/0814; C09K 11/06; C09K 2211/00; C09K 2211/10; C09K 2211/1007; H01L 27/32; H01L 51/0032; H01L 51/005; H01L 51/006; H01L 51/0061; H01L 51/0073; H01L 51/0074; H01L 51/001; H01L 51/0058; H01L 51/0052; H01L 51/0094; H01L 51/50; H01L 51/5012; H01L 51/5016; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2014/0027747 A1* 1/2014 Mun .................... H01L 51/006
                                                   257/40

FOREIGN PATENT DOCUMENTS

| KR | 10-2008-0077288 | A  | 8/2008  |            |
|----|-----------------|----|---------|------------|
| KR | 10-2009-0051141 | A  | 5/2009  |            |
| KR | 10-1108519      | B1 | 1/2012  |            |
| KR | 10-2012-0111670 | A  | 10/2012 |            |
| KR | 10-2012-0117676 | A  | 10/2012 |            |
| KR | 10-1493482      | B1 | 2/2015  |            |
| KR | 10-1535606      | B1 | 7/2015  |            |
| WO | WO-2012177006   | A2 * | 12/2012 | ......... H01L 51/0061 |
| WO | WO-2016032066   | A1 * | 3/2016  | ............ H01L 51/50 |

OTHER PUBLICATIONS

Machine translation of WO2012-177006. (Year: 2012).*
Machine translation of WO2016/032066. (Year: 2016).*
Hirata et al., "Efficient Persistent Room Temperature Phosphorescence in Organic Amorphous Materials under Ambient Conditions".
Office Action from China for corresponding Chinese application No. 201680037115.5, ten pages, dated Jan. 26, 2021.
Office Action dated Sep. 27, 2021, in corresponding KR Application No. 10-2015-0090751, 11 pages.

* cited by examiner

*Primary Examiner* — Andrew K Bohaty
(74) *Attorney, Agent, or Firm* — Vorys, Sater, Seymour & Pease LLP; Mih Suhn Koh

(57) ABSTRACT

Provided are a compound capable of lowering a driving voltage, enhancing light emitting efficiency and thermal resistance, and improving lifespan and color purity of the element, an organic element using the same, and an electric device for the same.

9 Claims, 1 Drawing Sheet

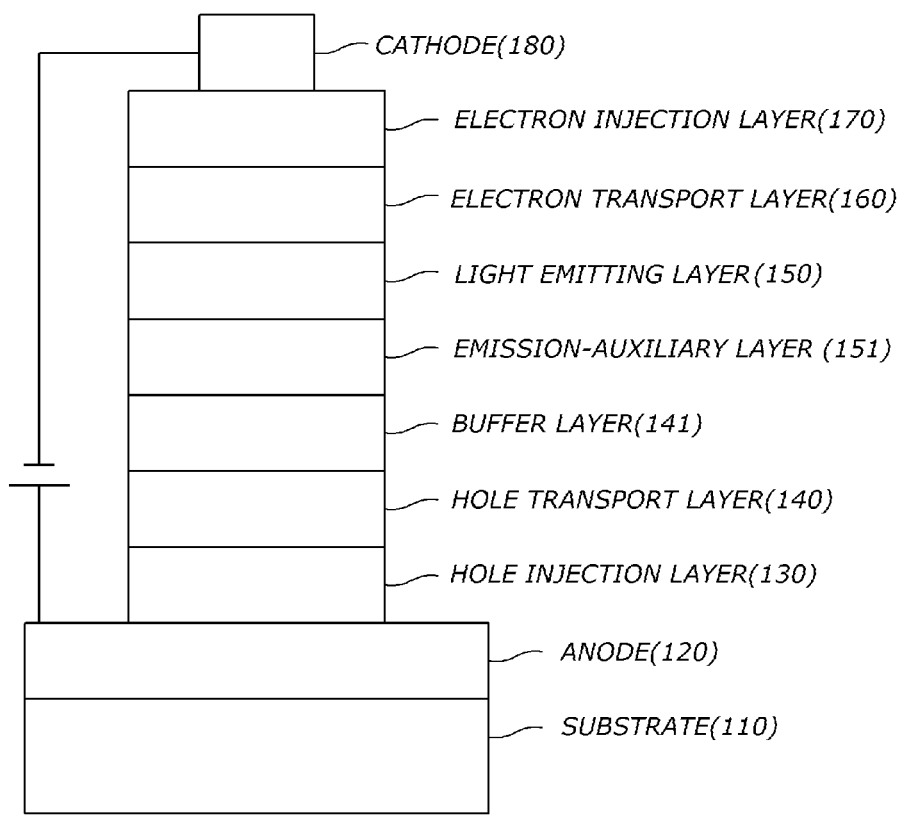

COMPOUND FOR ORGANIC ELECTRIC ELEMENT, ORGANIC ELECTRIC ELEMENT USING SAME, AND ELECTRONIC APPARATUS THEREOF

CROSS-REFERENCE TO RELATED APPLICATION

This application claims priority from and the benefit under 35 U.S.C. § 119(a) of Korean Patent Application No. 10-2015-0090751 filed on Jun. 25, 2015, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

Flat panel display devices are playing a very important role in supporting a high image information society, showing rapid growth mainly in the Internet in recent years.

In particular, an organic electroluminescent device (organic EL device) capable of being driven at low voltage as self-luminous type has excellent viewing angle and contrast ratio, is lightweight and thin because no backlight is required, and has advantages in terms of power consumption, compared with liquid crystal displays (LCDs) which are the mainstream of flat panel display devices. Also, organic EL device is also getting attention as next generation display device because of their high response speed and wide color reproduction range.

Generally, an organic electroluminescent device is formed on a glass substrate in the following order: an anode made of a transparent electrode, an organic thin film including a light emitting region, and a metal electrode. Here, the organic thin film may include a hole injection layer (HIL), a hole transport layer (HTL), an electron transport layer (ETL), or an electron injection layer (EIL) in addition to an emitting layer (EML) and may further include a an emission-auxiliary layer, an electron blocking layer (EBL) or a hole blocking layer (HBL) on the emission characteristics of the light emitting layer.

When an electric field is applied to the organic electroluminescent device having such a structure, holes are injected from the anode and electrons are injected from the cathode. The injected holes and electrons recombine in the light emitting layer through the hole transporting layer and the electron transporting layer, respectively, thereby forming luminescent excitons. The formed luminescent excitons emit light while transitioning to the ground states. At this time, a luminescent dye (guest) is doped in the light emitting layer (host) to increase the efficiency and stability of the luminescent state.

In order to utilize the organic electroluminescent device in various display media, the lifetime of the device is important, and various studies are currently under way to increase the lifetime of the organic electroluminescent device.

Particularly, various studies for an excellent lifetime characteristic of an organic electric device have been conducted on an organic material which is inserted into a buffer layer such as a hole transporting layer or an emission-auxiliary layer. For this purpose, a hole injecting layer and a hole transporting layer material having high uniformity and low crystallinity are required for forming a thin film after deposition, while giving high hole transporting characteristics from the anode to the organic layer.

In addition, it is required to develop material of a hole injection layer and a hole transport layer that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element.

In general, deposition is a main method of forming an OLED, and thus there is an actual need to develop a material that is durable to such a deposition method, that is, a highly heat-resistant material.

Currently, the major overcoming problem of organic light emitting devices is that the problem of power consumption and lifetime must be solved as the panel size of a mobile phone or a tablet PC becomes larger. However, it is difficult to simultaneously overcome the driving voltage and the lifetime solely by the hole transporting layer material.

This is because most of the materials having excellent hole transporting ability, that is, materials having high hole mobility, mostly have a planar structure (e.g., naphthyl, fluorene, phenanthrene), and the hole mobility and life time are increased when compounds having the above structure (with planarity) up to a certain number are introduced as a substituent of a hole transporting material, however, if the molecules are introduced excessively in order to lower a driving voltage required in the present industry, it is possible to drive at low voltage as the driving voltage is going down but the characteristics of lifetime are remarkably deteriorated.

In the case of a molecule in which planar structures are excessively introduced, holes are trapped and stabilized between the plate structures when the constant current is continuously supplied in the evaluation of device lifetime, so that the hole mobility is lowered, as a result, the driving voltage rises in order to apply a constant current, resulting in an adverse effect on the lifetime of the device. This is expressed by the following equation.

$$J = \frac{9}{8}\epsilon\mu\frac{V^2}{d^3}\theta = \frac{9}{8}\epsilon\mu\frac{1}{d}F^2\theta \qquad \langle\text{Equation 1}\rangle$$

J=Space Charge limited current, ε=Permittibility
μ=Mobility Coefficient, θ=Charge Trap Coefficient (Free Carrier/total Carrier)
V=Voltage, d=Thickness When the number of free carriers decreases due to a trap phenomenon, in a current driven organic electroluminescent device requiring a constant current, the value of θ decreases and the driving voltage rises. This may bring about a very fatal effect on the lifetime.

Therefore, as described above, introduction of a certain number or more of the plate structure capable of increasing the hole mobility cause a harmful effect on the lifetime, and thus, there is a limit to lowering the driving voltage by using it.

On the other hand, it can be seen that the compound substituted with deuterium shows much thermodynamic behavior as compared with the non-substituted compound. As an example of such thermodynamic properties, comparing the iridium compound substituted with deuterium with the non-substituted compound, the characteristics are different due to the difference between the bond length of carbon and hydrogen and the bond length of carbon and deuterium. It can be confirmed that the van der Waals force between molecules of the compound substituted with deuterium due to the short bonding length becomes weaker comparing to the non-substituted compound, and thus it shows higher luminous efficiency.

When the compound is substituted with deuterium, the energy of the zero point energy, that is, the bottom state is lowered and the molecular hardcore volume becomes smaller as the bond length of carbon and deuterium becomes shorter than the bond length of carbon and hydrogen. Thus, the electron polarizability can be reduced, and the thin film volume can be increased by weakening the intermolecular interaction (J. Polym. Sci. 1980, 18, 853). It is considered that these characteristics can produce an effect of lowering the crystallinity of the thin film, that is, an amorphous state and, in general, it is very effective to realize the necessary amorphous state in order to improve lifetime and driving characteristics of an organic electroluminescent device (Chem. Rev. 2007, 107, 953).

However, many studies have not been conducted on a hole transporting material which can lower the driving voltage and improve the hole transfer ability by substituting with deuterium, and accordingly, it is strongly required to develop materials of the emission-auxiliary layer and the hole transport layer.

SUMMARY

In order to solve one or more of the above-mentioned problems in prior art, an aspect of the present invention is to provide a compound having efficient electron blocking ability and hole transport ability by using the compound substituted with deuterium, and allowing to lower a driving voltage, to improve luminous efficiency, to have a high heat-resistance, and to improve color purity and lifetime of the element, an organic electric element comprising the same, and an electronic device thereof.

In accordance with an aspect of the present invention, the compound represented by the following formula is provided. The following formula represents a compound in which amine group is bonded to a dibenzofuran core through a linking group (comprising a single bond), wherein at least one of $L^1$, $L^2$, $Ar^1$ and $Ar^2$ is a $C_6$~$C_{60}$ aryl group substituted with one or more deuterium.

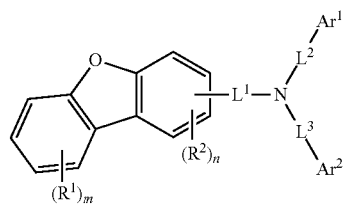

In another aspect of the present invention, organic electric elements comprising the compound represented by the formula 1 above and electronic devices including the organic electric element are provided.

According to the present invention, a specific compound in which a dibenzofuran core and an arylamine group substituted with deuterium are bonded to each other through a linking group is used as a material for the organic electric device, thereby lowering the driving voltage and improving the hole transporting ability and thermal stability. As a result, luminous efficiency, heat-resistance, and lifetime of the organic electric elements can be improved

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine, bromine, chlorine or iodine.

Unless otherwise stated, the term "alkyl" or "alkyl group" as used herein has a single bond of 1 to 60 carbon atoms, and means a radical of a saturated aliphatic functional group including a linear alkyl group, a branched chain alkyl group, a cycloalkyl group (alicyclic), a cycloalkyl group substituted with an alkyl group, an alkyl group substituted with a cycloalkyl group and the like.

Unless otherwise stated, the term "haloalkyl" or "halogen alkyl" as used herein includes an alkyl group substituted with a halogen.

Unless otherwise stated, the term "heteroalkyl" as used herein means alkyl substituted one or more carbon atoms constituting an alkyl group with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an alkyl group to which an oxygen radical is attached, but not limited to, and has 1 to 60 carbon atoms.

Unless otherwise stated, the term "alkenoxyl group", "alkenoxy group", "alkenyloxy group" or "alkynyloxy group" as used herein means an alkenyl group to which an oxygen radical is attached, but not limited to, and has 2 to 60 carbon atoms.

Unless otherwise stated, the term "aryloxyl group" or "aryloxy group" as used herein means an aryl group to which an oxygen radical is attached, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. For example, aryl group may be a phenyl group, a biphenyl group, a fluorene group, spirofluorene group or a spirobifluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, but not limited to, includes at least one of monocyclic and polycyclic rings, and may also be formed in conjunction with an adjacent group.

Unless otherwise stated, the term "heterocyclic group" as used herein contains one or more heteroatoms, but not limited to, has 2 to 60 carbon atoms, includes at least one of monocyclic and polycyclic rings, and may include heteroalicyclic and/or aromatic group containing. Also, the heterocyclic group may also be formed in conjunction with an adjacent group.

Unless otherwise stated, the term "heteroatom" as used herein represents at least one of N, O, S, P, and Si.

Also, the term "heterocyclic group" may include $SO_2$ instead of carbon consisting of cycle. For example, "heterocyclic group" includes compound below.

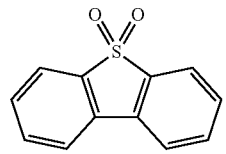 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

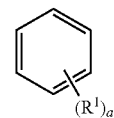

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. When a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

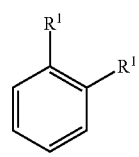

(a = 2)

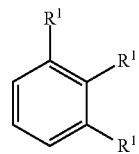

(a = 3)

FIGURE illustrates an organic electric element according to an embodiment of the present invention.

Referring to FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed on the first electrode 120. Here, layers other than a light emitting layer 150 may be omitted. The organic material layer may further include a hole blocking layer, an electron blocking layer, an emission-auxiliary layer 151, a buffer layer 141, etc., and the electron transport layer 160 or the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an electron transport layer 160, an electron injection layer 170, as a host or a dopant material of a light emitting layer 150, or as a material of a capping layer. Preferably, the inventive compound may be used as a hole transport layer 140 and/or the emission-auxiliary layer 151. Also, the inventive compound employed in the organic material layer may be used as a single compound or as a mixture of two or more kinds.

On the other hand, even if the core is the same, the band gap, the electrical characteristics, the interface characteristics, and the like may be different depending on which substituent is bonded at which position. Therefore, the selection of core and the combination of sub-substituents coupled thereto are also very important. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B). On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

Therefore, according to the present invention, energy levels between organic material layers and $T_1$ values, inherent material properties (mobility, interfacial properties, etc.), and the like can be optimized by forming a hole transport layer or an emission-auxiliary layer which comprise the compound represented by the Formula 1, and thus it is possible to simultaneously improve the life span and efficiency of the organic electronic element.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G(Green), B(Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by the following Formula 1.

[Formula 1]

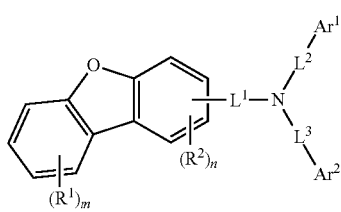

wherein,

R¹ and R² are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, they may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, m is an integer of 0 to 4, and when m is an integer of 2 or more, R¹s may be each the same or different from each other, n is an integer of 0 to 3, and when n is an integer of 2 or more, R²s may be each the same or different from each other.

Ar¹ and Ar² are each independently a $C_6$-$C_{60}$ aryl group, they may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, with the proviso that at least one of L¹, L², Ar¹ and Ar² may be a $C_6$-$C_{60}$ aryl group substituted with one or more deuterium.

L¹ is selected from the group consisting of a single bond; a $C_6$-$C_{60}$ arylene group; a divalent $C_2$-$C_{60}$ heterocyclic group containing at least one heteroatom selected from the group consisting of O, N, S, Si, and P; a fluorenylene group; a divalent fused ring formed by a $C_3$-$C_{60}$ aliphatic ring and a $C_6$-$C_{60}$ aromatic ring; and a divalent $C_1$-$C_{60}$ aliphatic hydrocarbon group, and they (except for a single bond) may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, L² and L³ are each independently selected from the group consisting of a single bond; and a $C_6$-$C_{60}$ arylene group, and they (except for a single bond) may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, with the proviso that when both L² and L³ are $C_6$ arylene group, the case where Ar¹ is a $C_6$ aryl group substituted with deuterium and Ar² is a $C_6$ aryl group substituted with deuterium is excluded.

Here, at least one of Ar¹ and Ar² may be represented by Formula 1a below.

[Formula 1a]

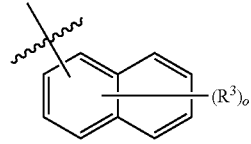

Wherein, R³ may be selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_3$-$C_{20}$ cycloalkyl group, a $C_7$-$C_{20}$ arylalkyl group, and a $C_8$-$C_{20}$ arylalkenyl group, and at least one of R³ may be deuterium.

o is an integer of 0 to 7, and, and R³s are each the same or different from each other when o is an integer of 2 or more, and at least one of R³ is deuterium or a $C_6$-$C_{20}$ aryl group substituted with deuterium when o is an integer of 1 to 7.

Here, Formula 1 above may be represented by any one of Formulas 2 to 5 below.

<Formula 2>

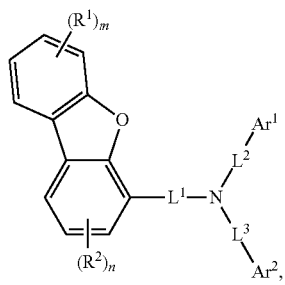

<Formula 3>

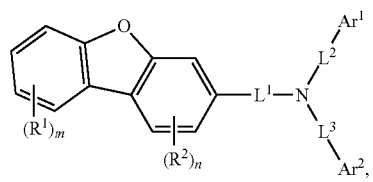

<Formula 4>
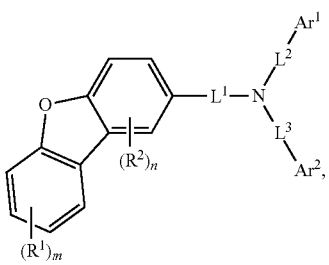
<Formula 5>
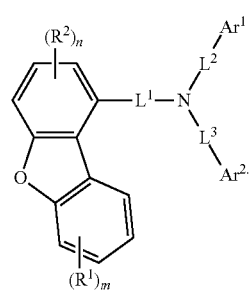
In Formulas 2 to 5, $R^1$, $R^2$, $L^1$ to $L^3$, $Ar^1$, $Ar^2$, m and n are the same as defined in Formula 1 above.
Specifically, the compound represented by Formula 1 may be any one of the following compounds P-1 to P-60.
P-1
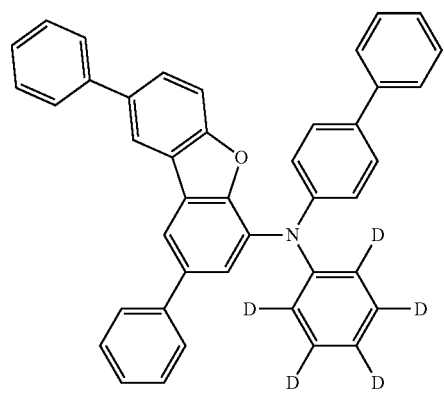
P-2
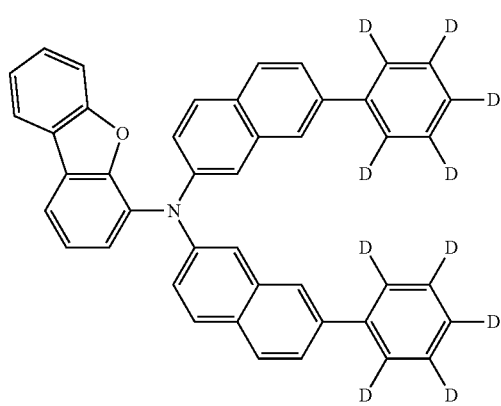
P-3
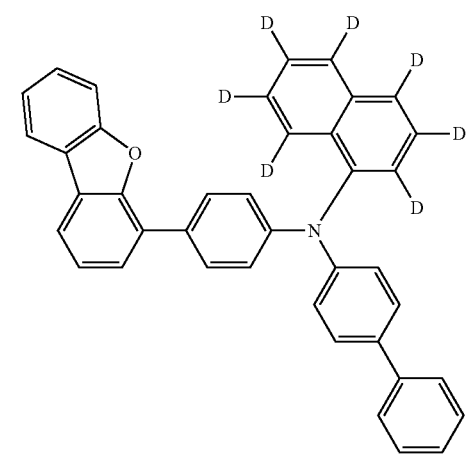
P-4
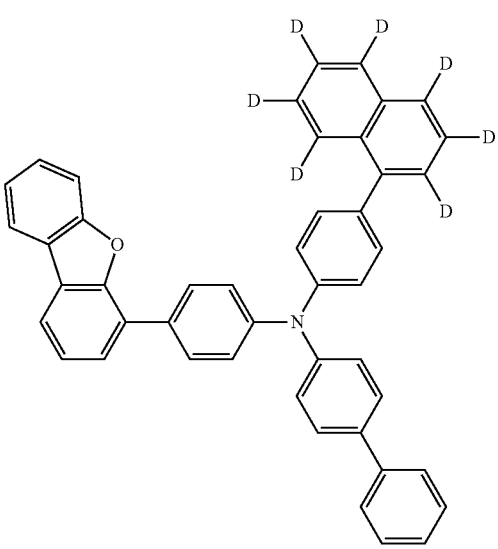
P-5
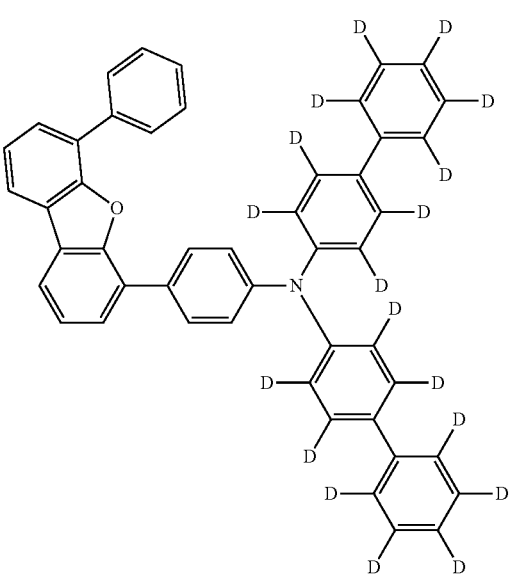

-continued
P-6
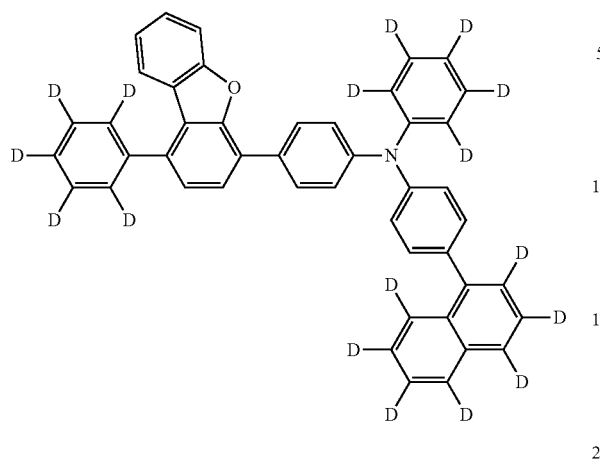
P-7
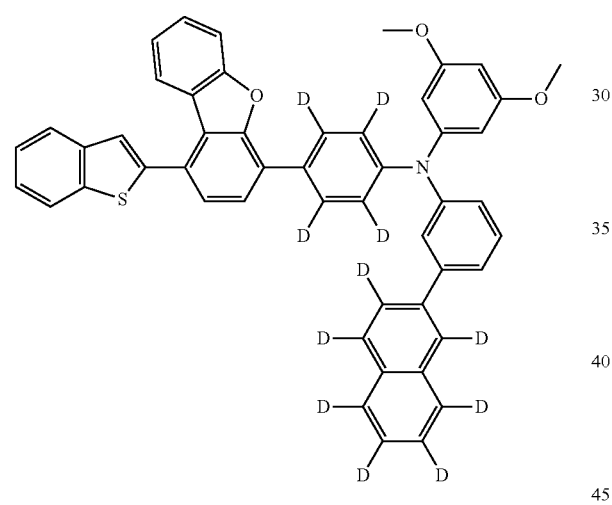
P-8
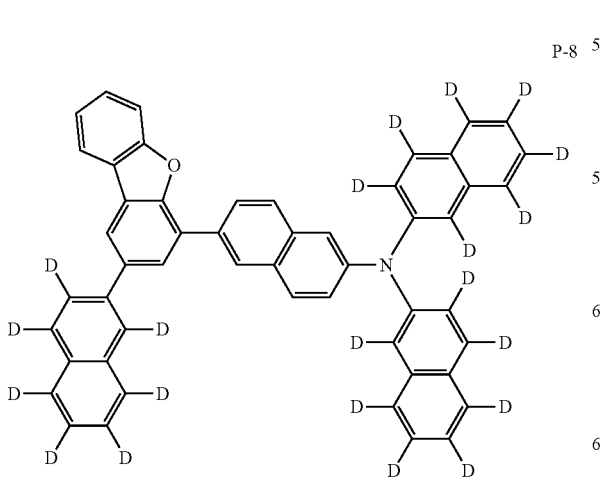
-continued
P-9
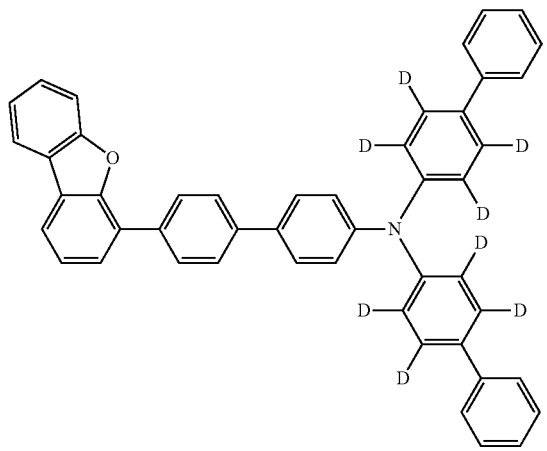
P-10
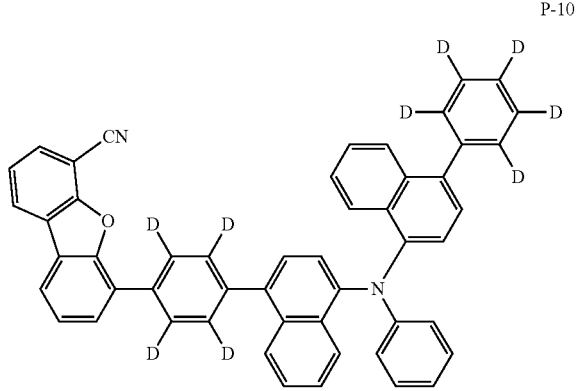
P-11
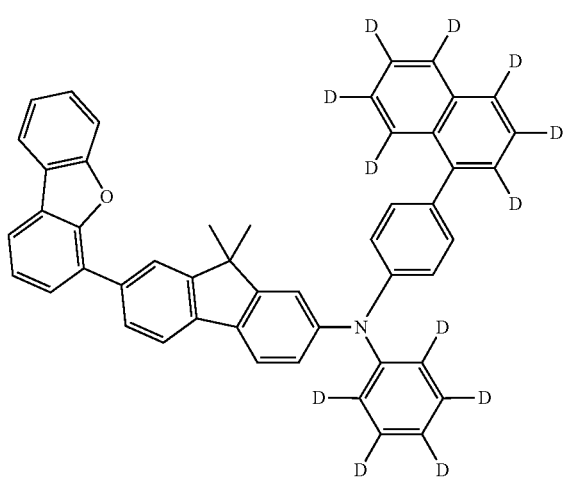

-continued
P-12
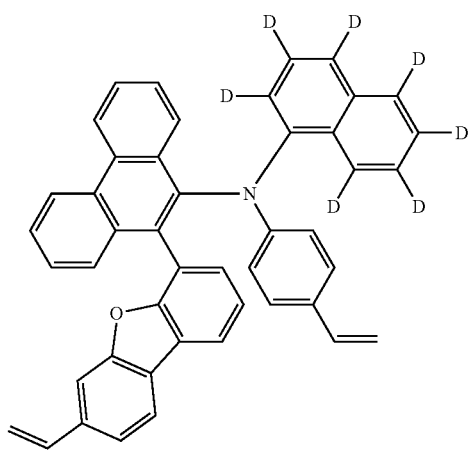
P-13
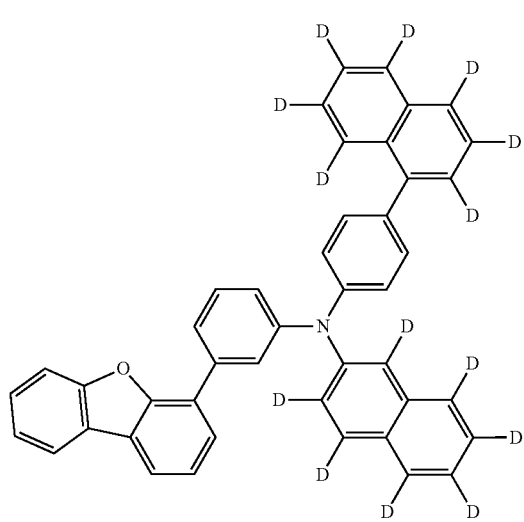
P-14
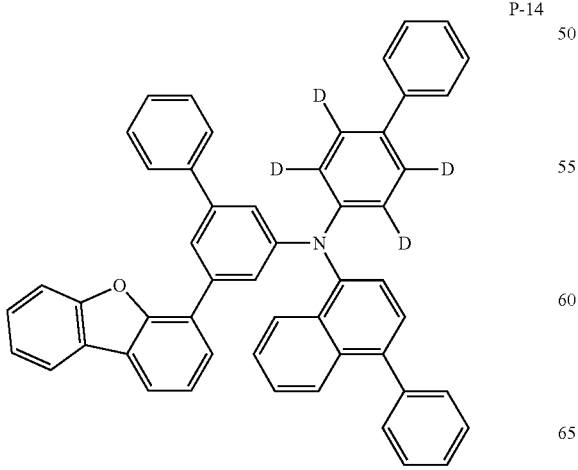
P-15
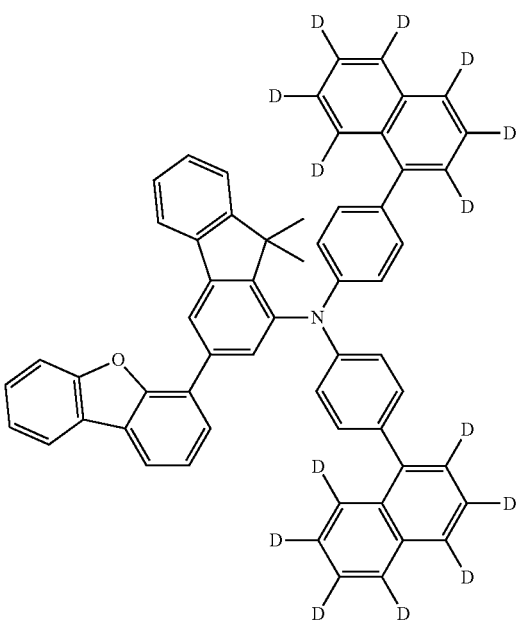
P-16
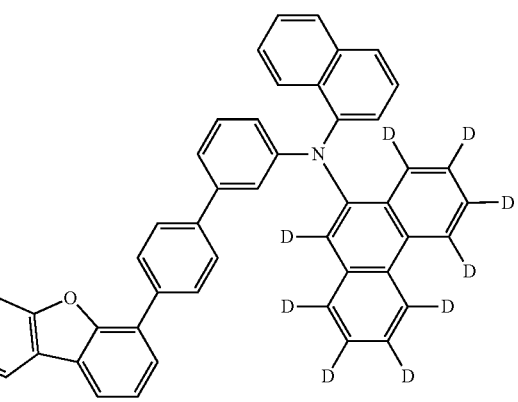
P-17
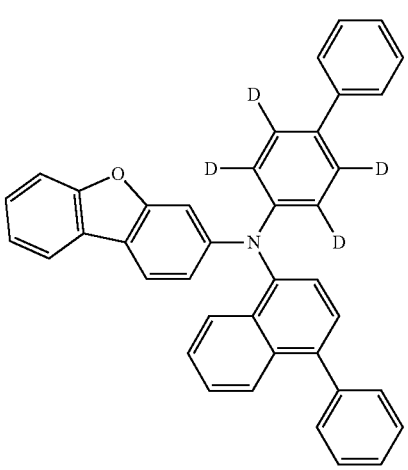

P-18
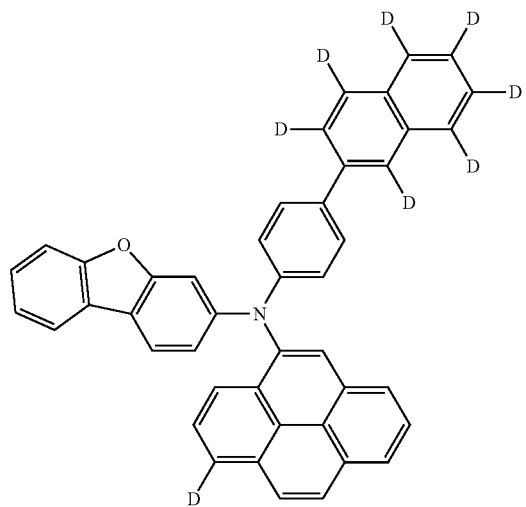
P-19
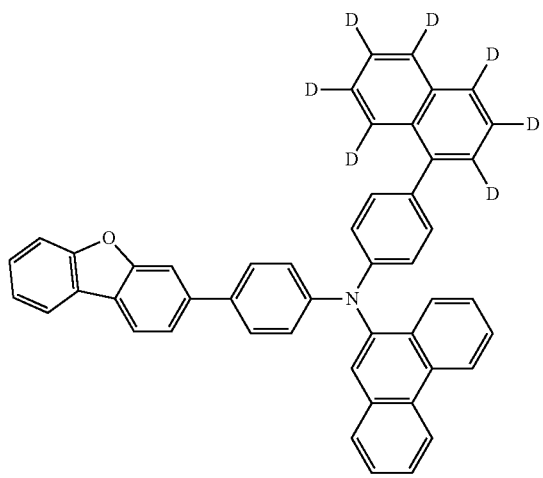
P-20
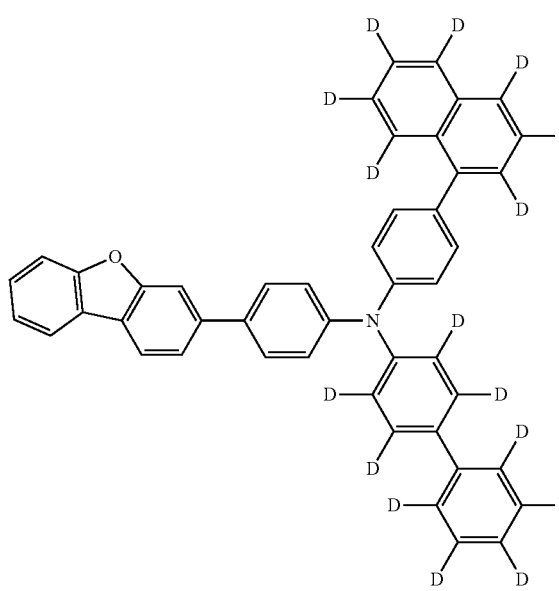
P-21
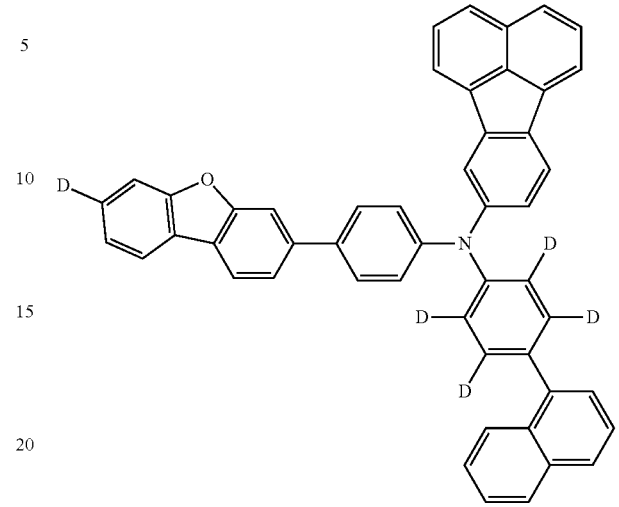
P-22
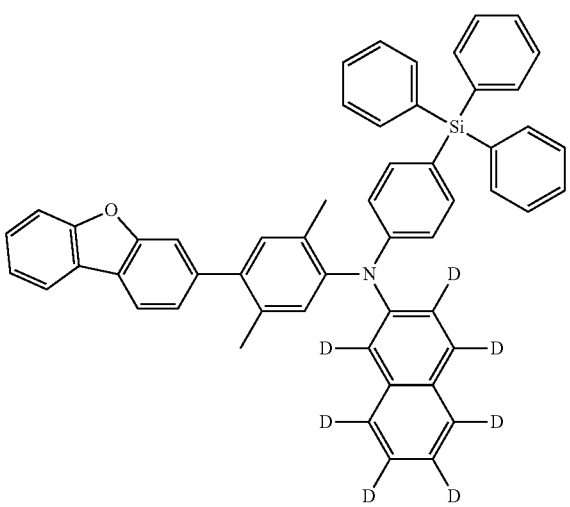
P-23
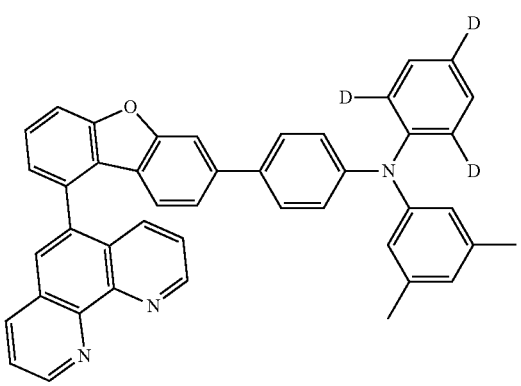

P-24
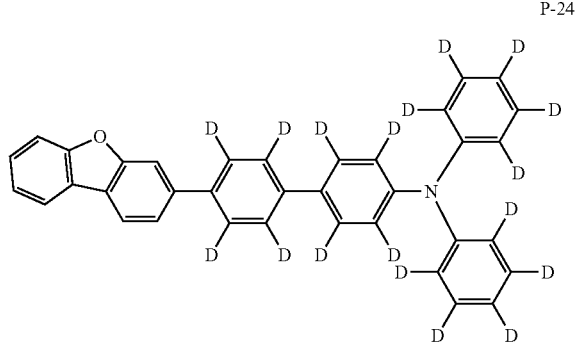
P-27
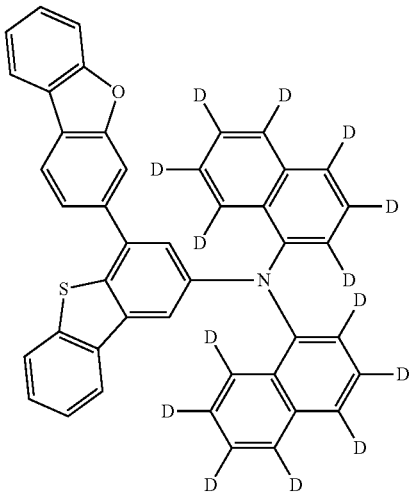
P-25
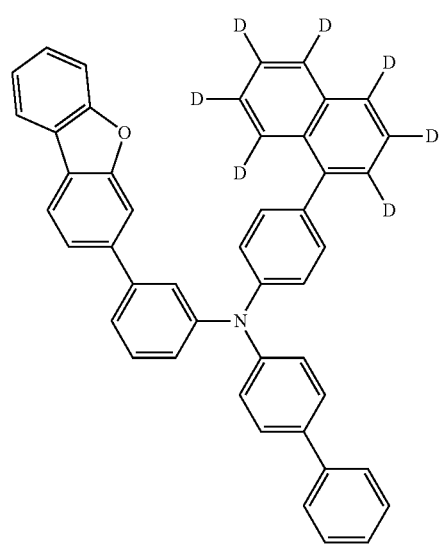
P-28
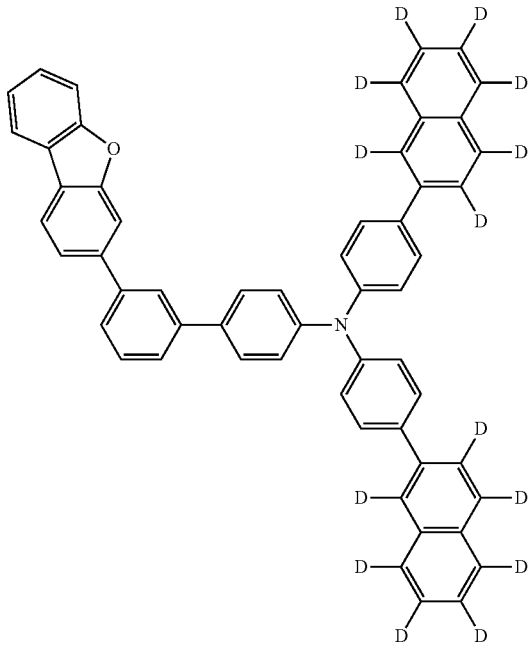
P-26
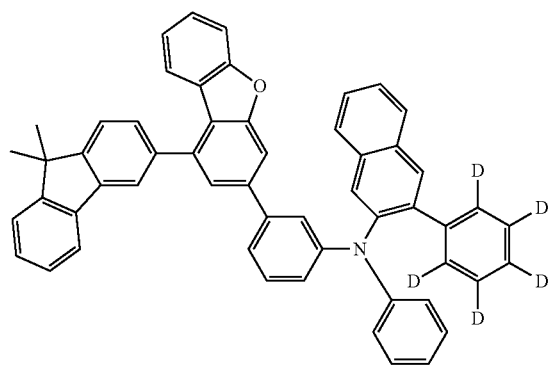
P-29
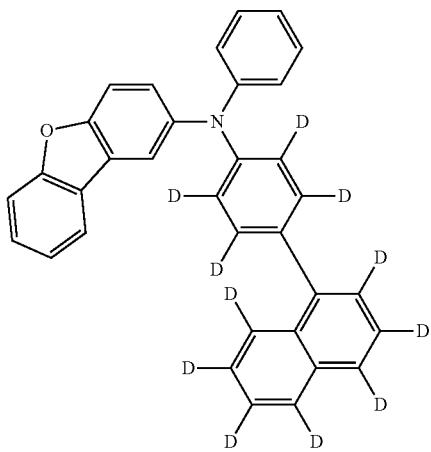

P-30
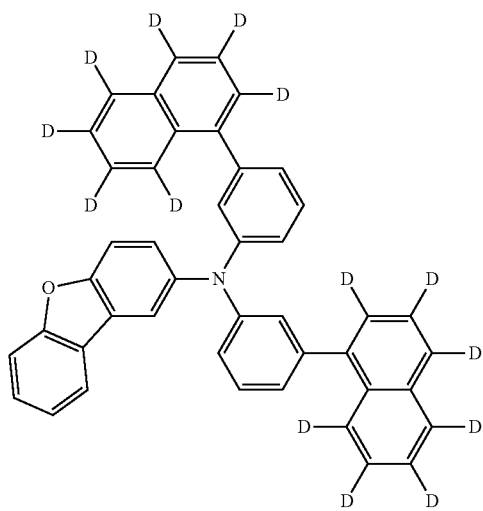
P-33
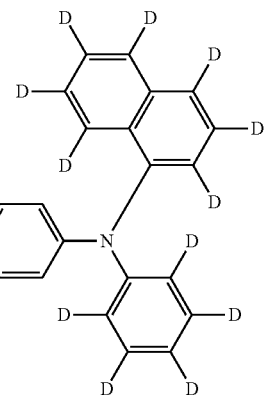
P-31
P-34
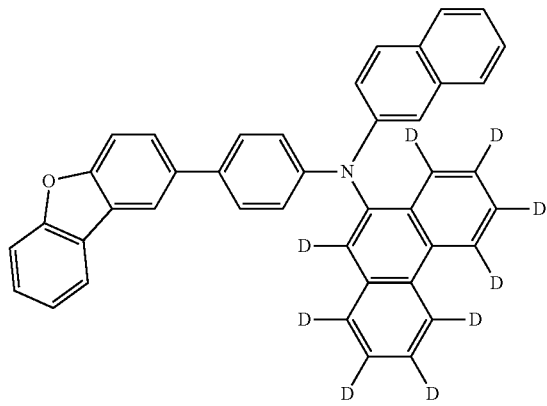
P-32
P-35
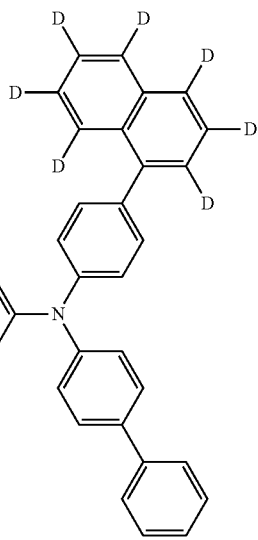

P-36
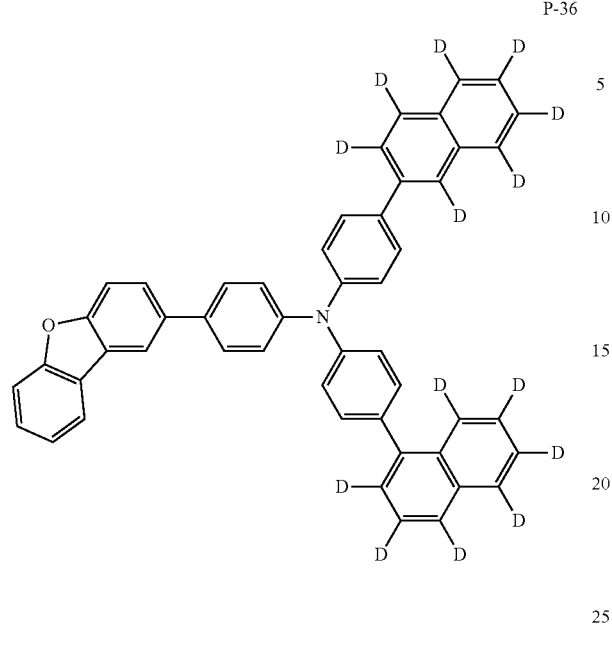
P-38
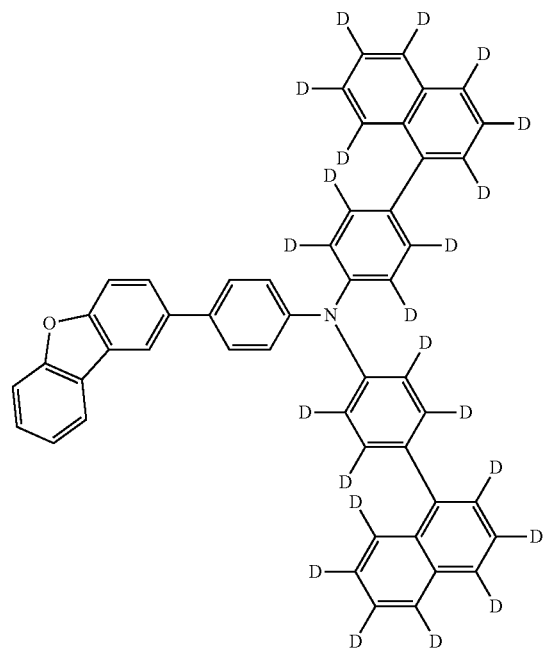
P-37
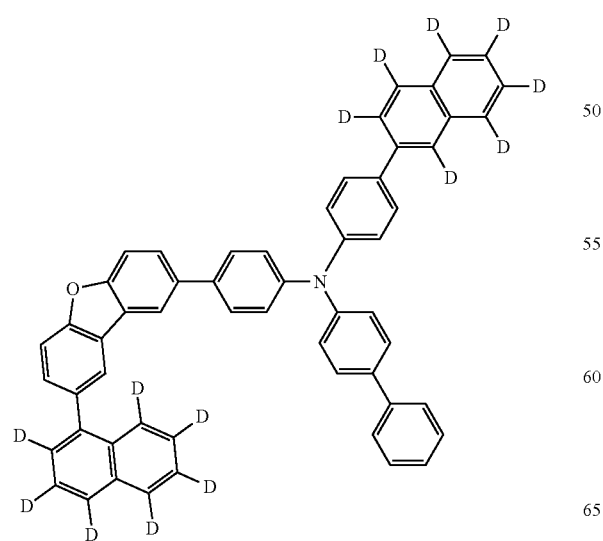
P-39
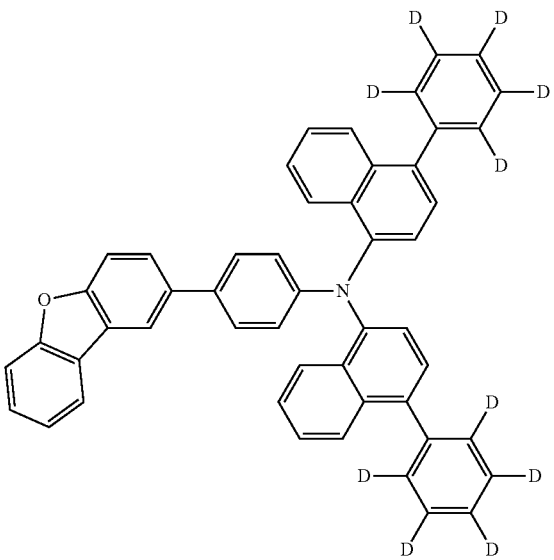

P-40
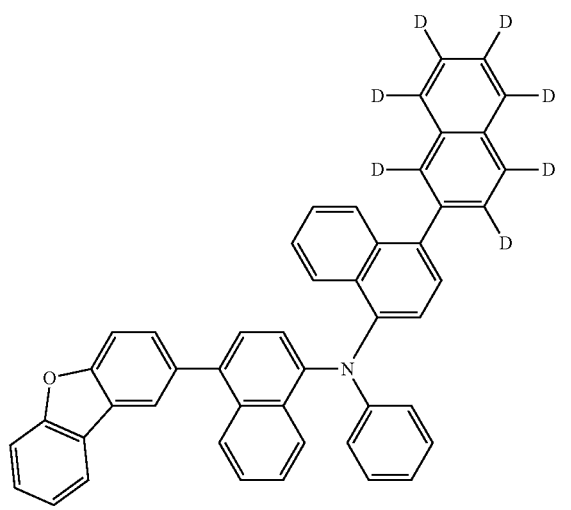
P-43
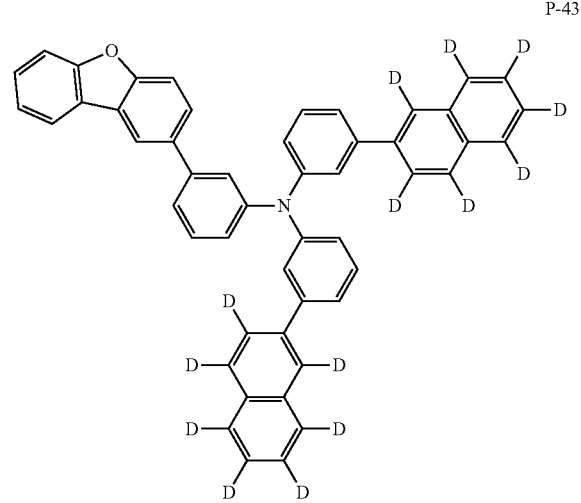
P-41
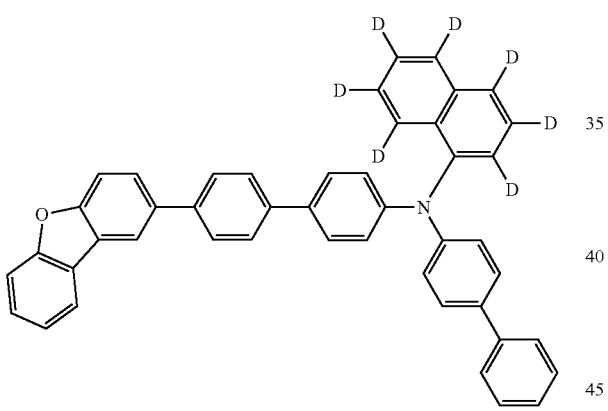
P-44
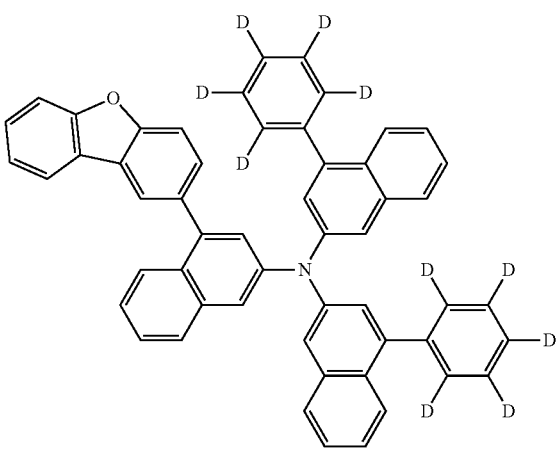
P-42
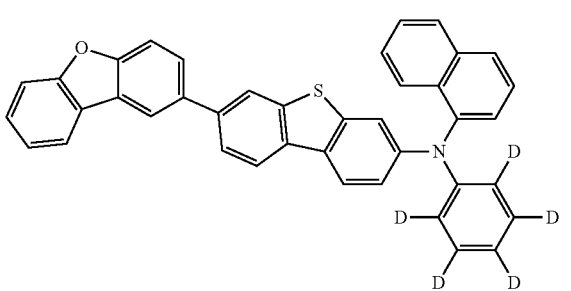
P-45
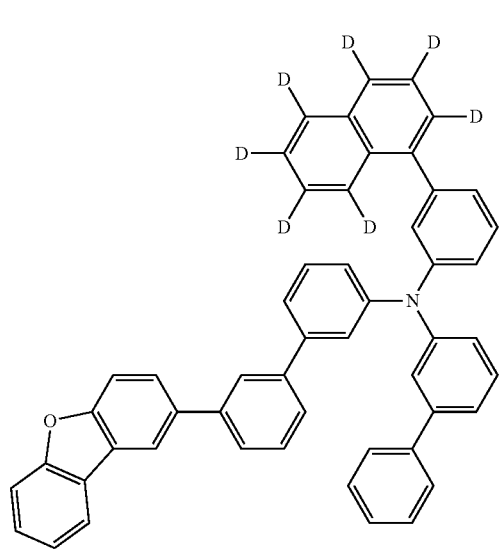

P-46
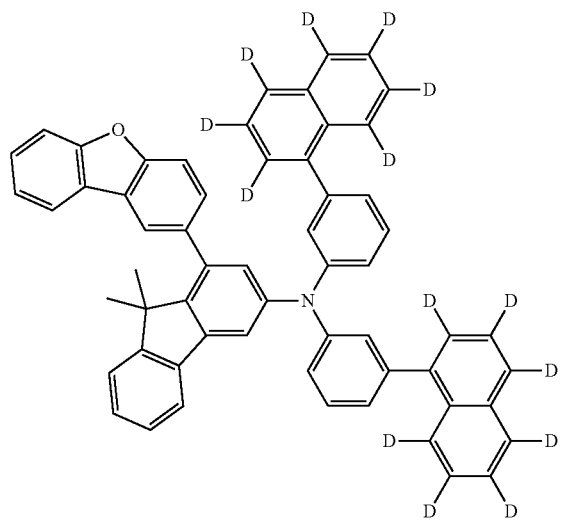
P-47
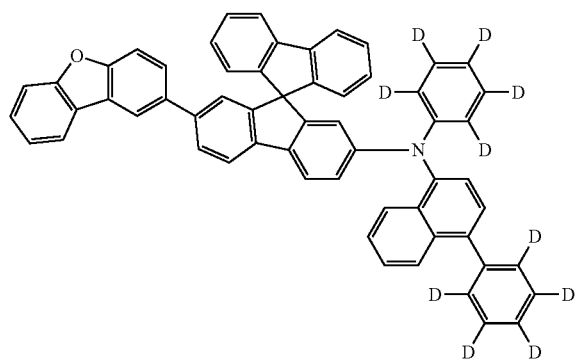
P-48
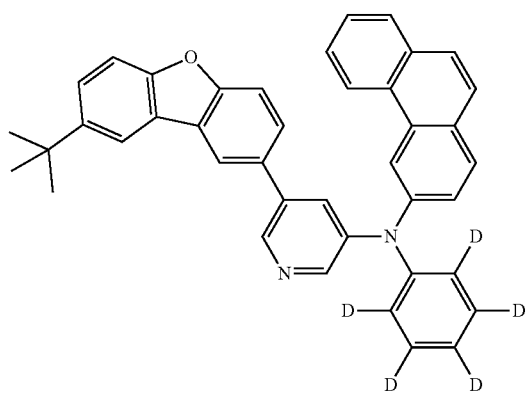
P-49
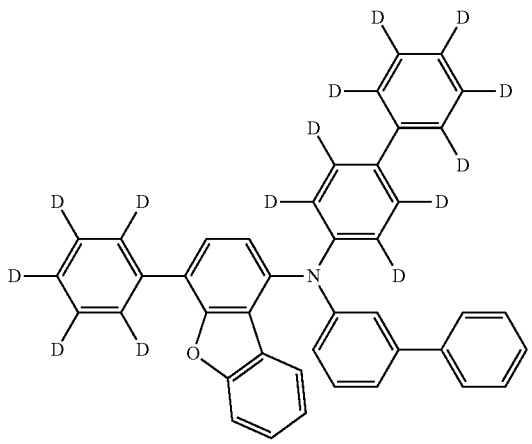
P-50
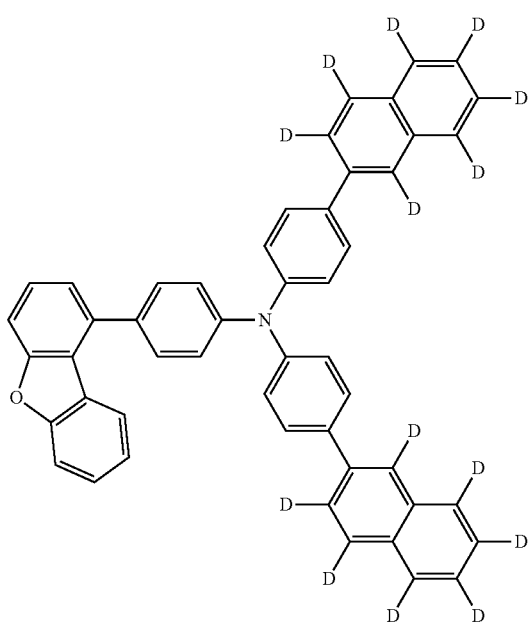
P-51
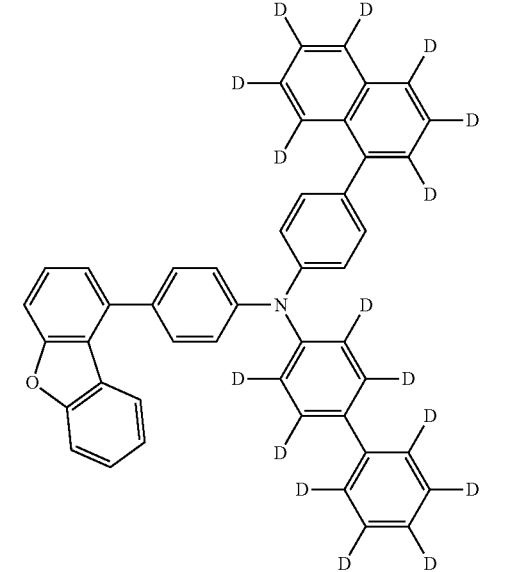

-continued
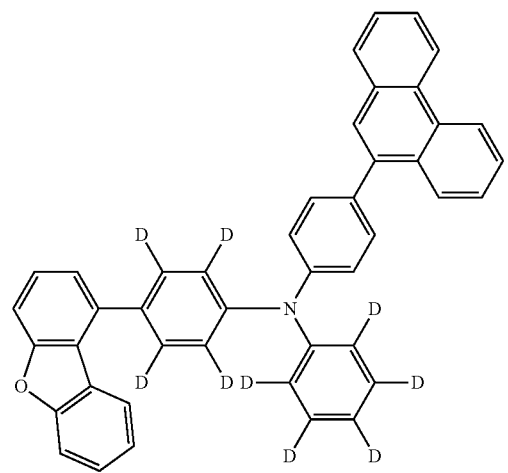
P-52
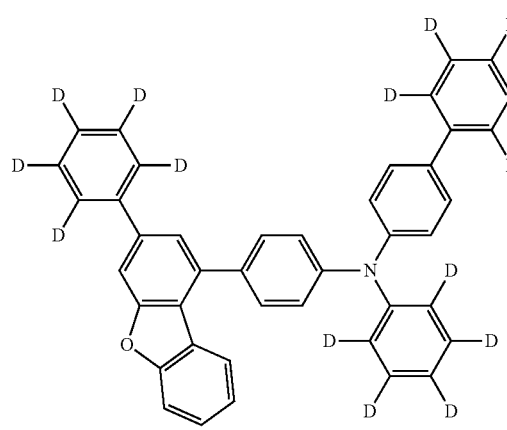
P-53
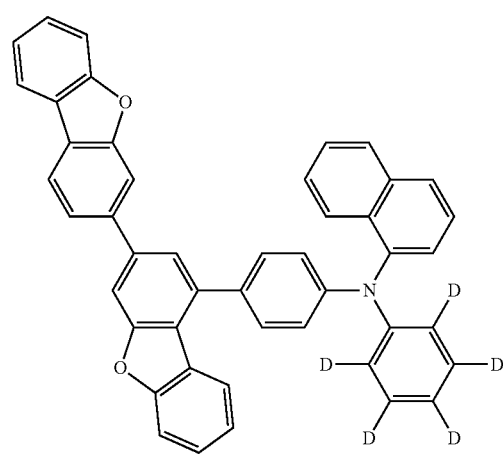
P-54
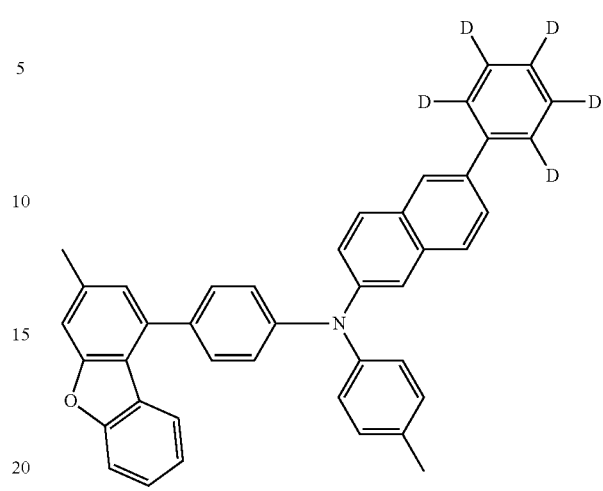
P-55
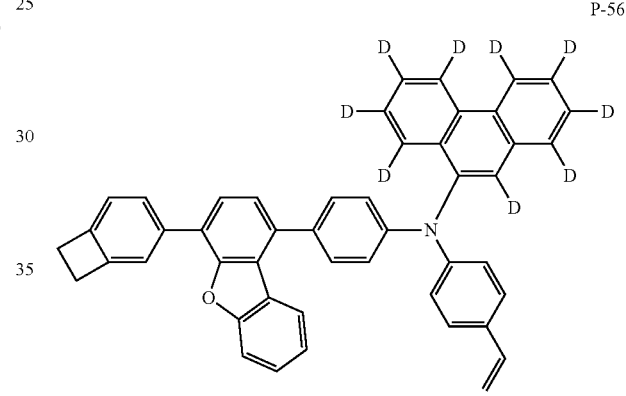
P-56
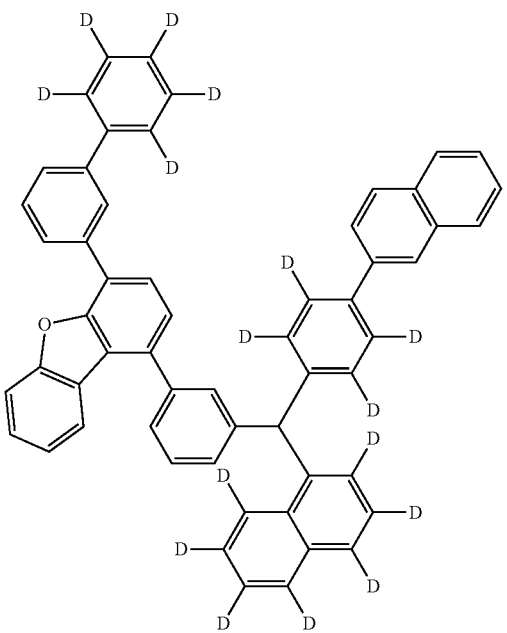
P-57

P-58

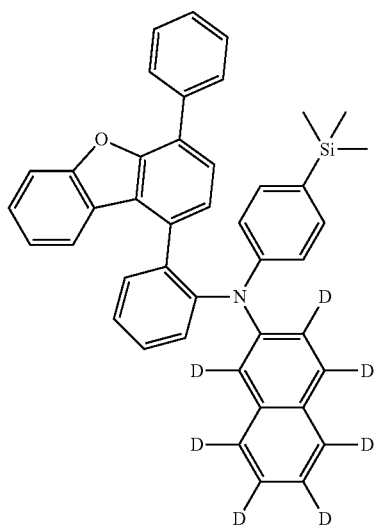

P-59

P-60

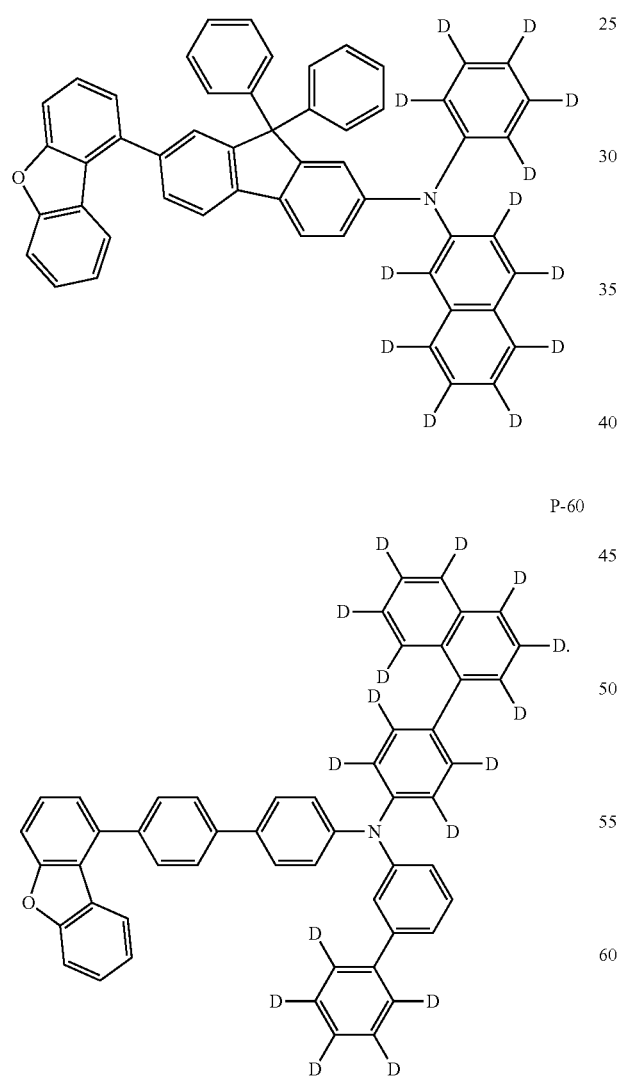

Hereinafter, synthesis examples of the compound represented by Formula 1 according to one embodiment of the present invention and preparation examples of an organic electric element will be described in detail by way of examples. However, these synthesis or preparation examples are only illustrative for those skilled in the art to easily practice the present invention. The scope of the present invention is not limited to these synthesis or preparation examples.

EXAMPLES

Synthesis Example

The compound (final products) represented by Formula 1 according to the present invention are synthesized by reacting Sub 1 and Sub 2 as shown in Reaction Scheme 1, but are not limited thereto.

<Reaction Scheme 1>

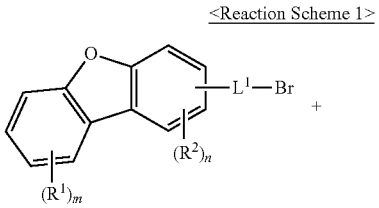

Sub 1

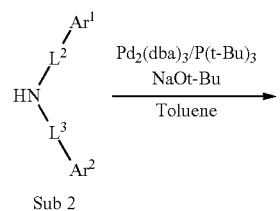

Sub 2

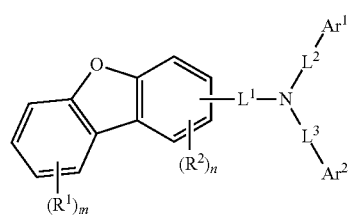

Final Products

I. Synthesis of Sub 1

Sub 1 of the Reaction Scheme 1 can be synthesized according to, but not limited to, the reaction route of the following Reaction Scheme 2.

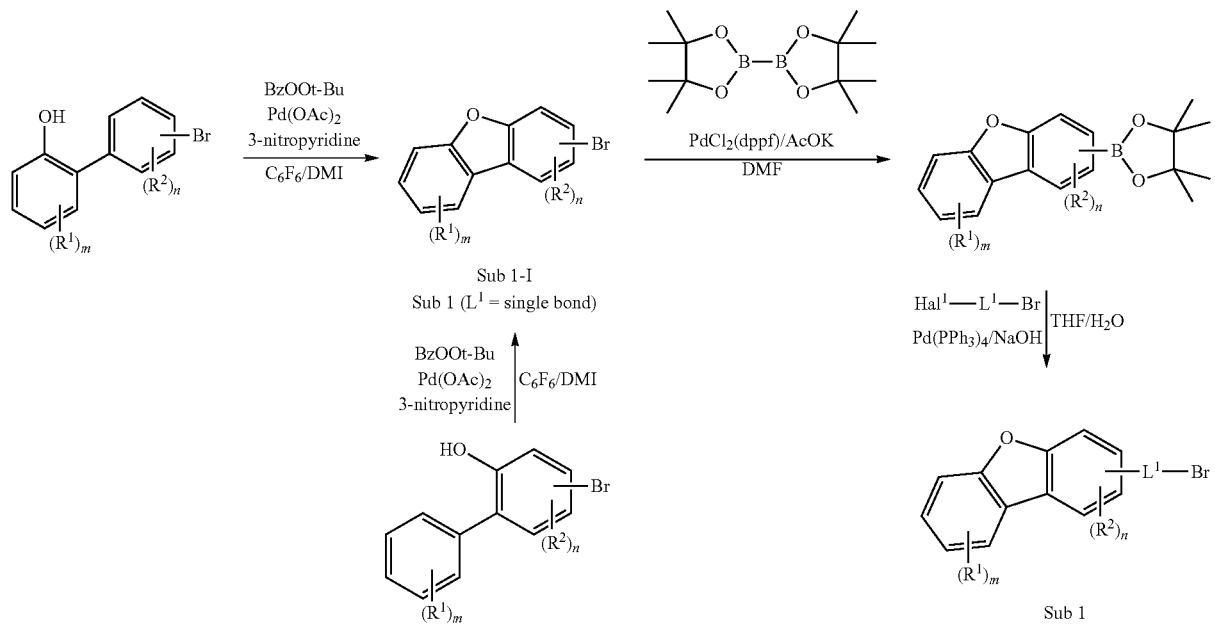

Here, Hal¹ may be Br or I.
Synthesis Examples of compounds comprised in Sub 1 are as follows.

1. Synthesis Example of Sub 1-3

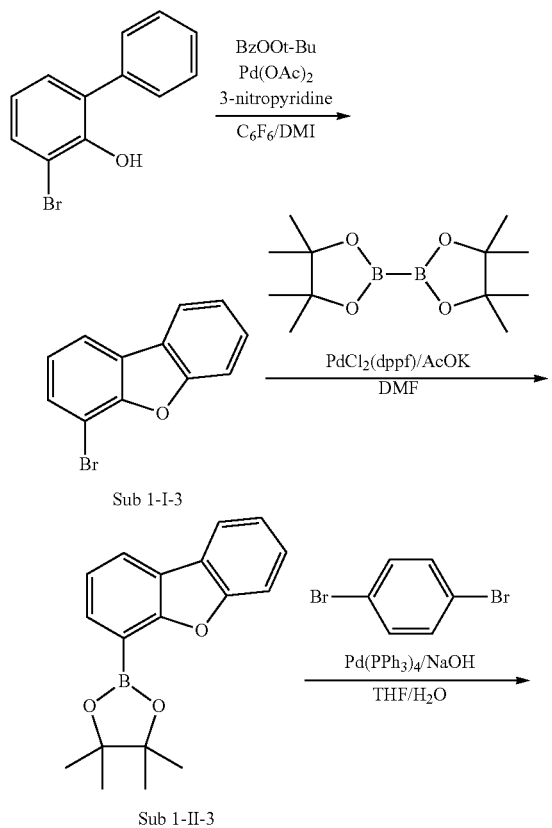

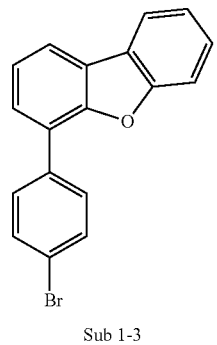

Sub 1-3

(1) Synthesis of Sub 1-I-3

The starting material 3-bromo-[1,1'-biphenyl]-2-ol (59.89 g, 240.43 mmol) was placed in a round bottom flask together with Pd(OAc)$_2$ (5.40 g, 24.04 mmol), 3-nitropyridine (2.98 g, 24.04 mmol), and dissolved in C$_6$F$_6$ (360 ml) and DMI (240 ml). Then, tert-butyl peroxybenzoate (93.40 g, 480.85 mmol) was added and the stirring at 90° C. was followed. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 29.11 g (yield: 49%) of the product.

(2) Synthesis of Sub 1-II-3

Sub 1-I-3 (29.11 g, 117.81 mmol) obtained in the above synthesis was dissolved in DMF (590 ml) in a round bottom flask, and then, Bis(pinacolato)diboron (32.91 g, 129.59 mmol), Pd(dppf)Cl$_2$ (2.89 g, 3.53 mmol), KOAc (34.69 g, 353.43 mmol) were added and stirred at 90° C. When the reaction was completed, DMF was removed by distillation and extracting with CH$_2$Cl$_2$ and water was followed. Then, the organic layer was dried with MgSO$_4$ and concentrated and the concentrate was passed through silica gel column and recrystallized to obtain 28.42 g (yield: 82%) of the product.

(3) Synthesis of Sub 1-3

Sub 1-II-3 (14.21 g, 48.31 mmol) obtained in the above synthesis was dissolved in THF (170 ml) in a round bottom flask, and then, 1,4-dibromobenzene (12.54 g, 53.14 mmol), Pd(PPh$_3$)$_4$ (1.67 g, 1.45 mmol), NaOH (5.80 g, 144.93 mmol), water (85 ml) were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 12.49 g (yield: 80%) of the product.

2. Synthesis Example of Sub 1-6

<Reaction Scheme 4>

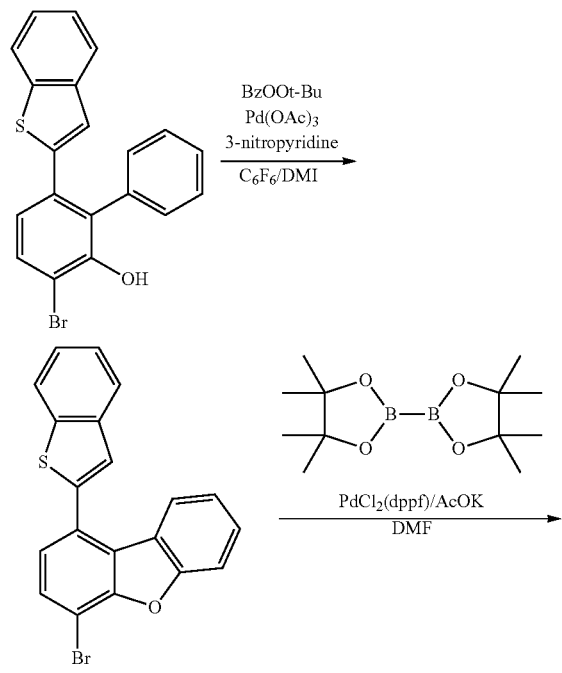

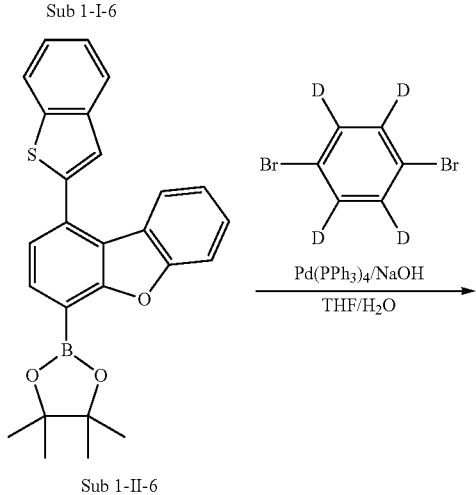

Sub 1-II-6

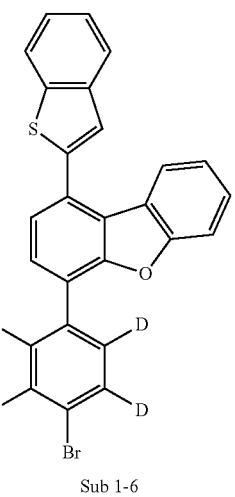

Sub 1-6

(1) Synthesis of Sub 1-I-6

Pd(OAc)$_2$ (3.60 g, 16.03 mmol), 3-nitropyridine (1.99 g, 16.03 mmol), tert-butyl peroxybenzoate (62.28 g, 320.65 mmol), C$_6$F$_6$ (240 ml), DMI (160 ml) were added to the starting material 6-(benzo[b]thiophen-2-yl)-3-bromo-[1,1'-biphenyl]-2-ol (61.13 g, 160.32 mmol), and then 24.32 g (yield: 40%) of the product was obtained by using the same manner as described above for the synthesis of Sub 1-I-3.

(2) Synthesis of Sub 1-II-6

Bis(pinacolato)diboron (17.91 g, 70.54 mmol), Pd(dppf)Cl$_2$ (1.57 g, 1.92 mmol), KOAc (18.88 g, 192.37 mmol), DMF (320 ml) were added to Sub 1-I-6 (24.32 g, 64.12 mmol) obtained in the above synthesis, and then 21.05 g (yield: 77%) of the product was obtained by using the same manner as described above for the synthesis of Sub 1-II-3.

(3) Synthesis of Sub 1-6

1,4-dibromobenzene-d4 (13.03 g, 54.31 mmol), Pd(PPh$_3$)$_4$ (1.71 g, 1.48 mmol), NaOH (5.92 g, 148.12 mmol), THF (170 ml), water (85 ml) were added to Sub 1-II-6 (21.05 g, 49.37 mmol) obtained in the above synthesis, and then 14.06 g (yield: 62%) of the product was obtained by using the same manner as described above for the synthesis of Sub 1-3.

3. Synthesis Example of Sub 1-10

<Reaction Scheme 5>

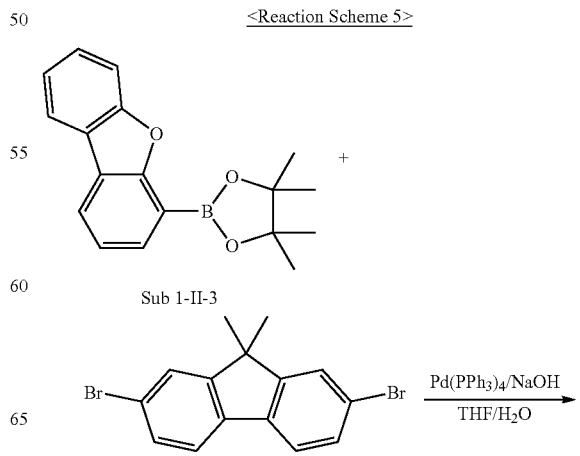

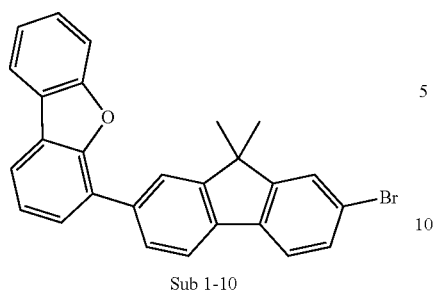

Sub 1-10

2,7-dibromo-9,9-dimethyl-9H-fluorene (17.73 g, 50.37 mmol), Pd(PPh₃)₄ (1.59 g, 1.37 mmol), NaOH (5.50 g, 137.38 mmol), THF (160 ml), water (80 ml) were added to Sub 1-II-3 (13.47 g, 45.79 mmol) obtained in the above synthesis, and then 14.69 g (yield: 73%) of the product was obtained by using the same manner as described above for the synthesis of Sub 1-3.

4. Synthesis Example of Sub 1-22

<Reaction Scheme 6>

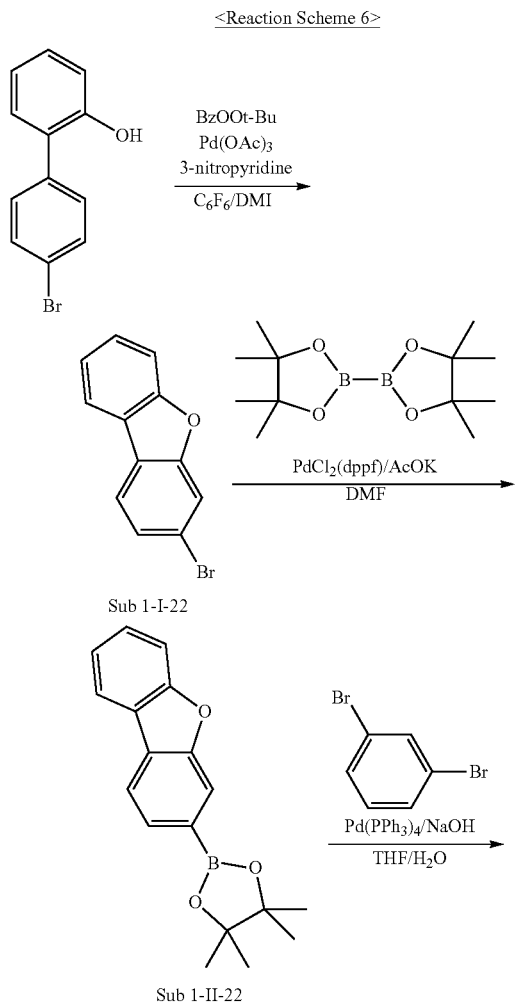

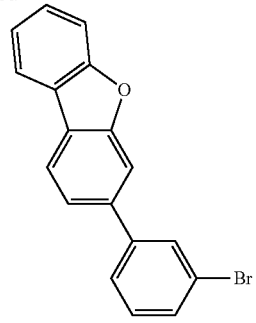

Sub 1-22

(1) Synthesis of Sub 1-I-22 합성

Pd(OAc)₂ (5.84 g, 26.02 mmol), 3-nitropyridine (3.23 g, 26.02 mmol), tert-butyl peroxybenzoate (101.07 g, 520.35 mmol), C₆F₆ (390 ml), DMI (260 ml) were added to the starting material 4'-bromo-[1,1'-biphenyl]-2-ol (64.81 g, 260.18 mmol), and then 30.21 g (yield: 47%) of the product was obtained by using the same manner as described above for the synthesis of Sub 1-I-3.

(2) Synthesis of Sub 1-II-22

Bis(pinacolato)diboron (34.15 g, 134.49 mmol), Pd(dppf)Cl₂ (3.00 g, 3.67 mmol), KOAc (36.00 g, 366.79 mmol), DMF (610 ml) were added to Sub 1-I-22 (30.21 g, 122.26 mmol) obtained in the above synthesis, and then 30.57 g (yield: 85%) of the product was obtained by using the same manner as described above for the synthesis of Sub 1-II-3.

(3) Synthesis of Sub 1-22

1,3-dibromobenzene (11.09 g, 47.01 mmol), Pd(PPh₃)₄ (1.48 g, 1.28 mmol), NaOH (5.13 g, 128.20 mmol), THF (150 ml), water (75 ml) were added to Sub 1-II-22 (12.57 g, 42.73 mmol) obtained in the above synthesis, and then 10.77 g (yield: 78%) of the product was obtained by using the same manner as described above for the synthesis of Sub 1-3.

5. Synthesis Example of Sub 1-24

<Reaction Scheme 7>

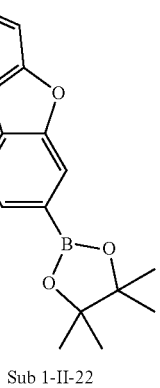

Sub 1-II-22

7. Synthesis Example of Sub 1-27

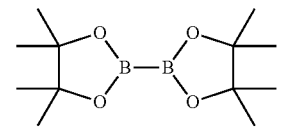

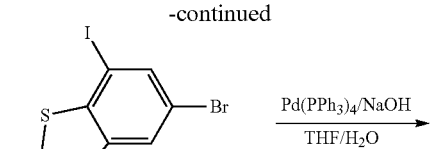

<Reaction Scheme 9>

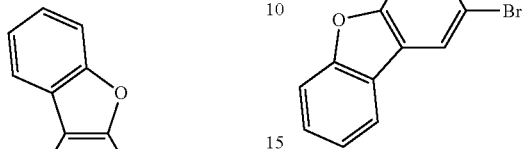

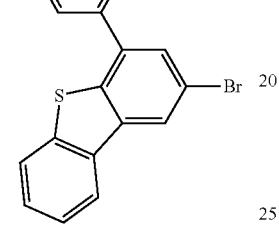

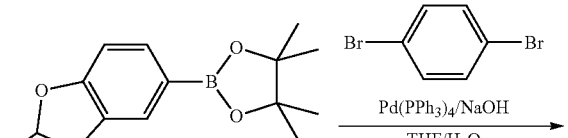

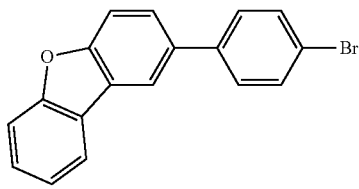

2-bromo-4-iododibenzo[b,d]thiophene (22.00 g, 56.54 mmol), Pd(PPh3)4 (1.78 g, 1.54 mmol), NaOH (6.17 g, 154.21 mmol), THF (180 ml), water (90 ml) were added to Sub 1-II-22 (15.12 g, 51.40 mmol) obtained in the above synthesis, and then 15.45 g (yield: 70%) of the product was obtained by using the same manner as described above for the synthesis of Sub 1-3.

6. Synthesis Example of Sub 1-26

<Reaction Scheme 8>

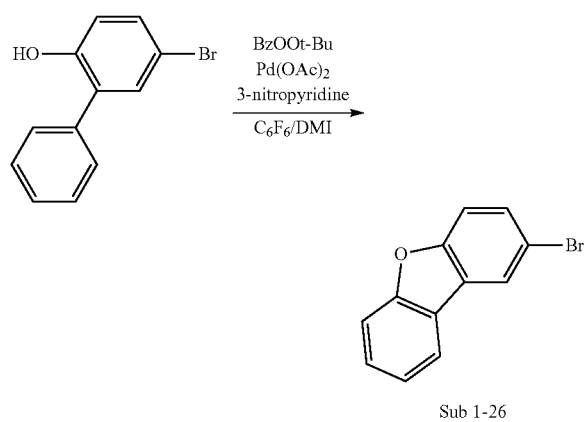

Pd(OAc)$_2$ (6.75 g, 30.04 mmol), 3-nitropyridine (3.73 g, 30.04 mmol), tert-butyl peroxybenzoate (116.71 g, 600.88 mmol), C$_6$F$_6$ (450 ml), DMI (300 ml) were added to the starting material 5-bromo-[1,1'-biphenyl]-2-ol (74.84 g, 300.44 mmol), and then 37.86 g (yield: 51%) of the product was obtained by using the same manner as described above for the synthesis of Sub 1-I-3.

(1) Synthesis of Sub 1-II-27
Bis(pinacolato)diboron (31.29 g, 123.23 mmol), Pd(dppf)Cl$_2$ (2.74 g, 3.36 mmol), KOAc (32.98 g, 336.07 mmol), DMF (560 ml) were added to Sub 1-26 (27.68 g, 112.02 mmol) obtained in the above synthesis, and then 28.34 g (yield: 86%) of the product was obtained by using the same manner as described above for the synthesis of Sub 1-II-3.

(2) Synthesis of Sub 1-27
1,4-dibromobenzene (11.93 g, 50.56 mmol), Pd(PPh$_3$)$_4$ (1.59 g, 1.38 mmol), NaOH (5.52 g, 137.89 mmol), THF (160 ml), water (80 ml) were added to Sub 1-II-27 (13.52 g, 45.96 mmol) obtained in the above synthesis, and then 12.33 g (yield: 83%) of the product was obtained by using the same manner as described above for the synthesis of Sub 1-3.

8. Synthesis Example of Sub 1-31

<Reaction Scheme 10>

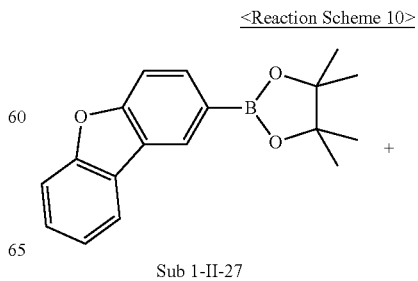

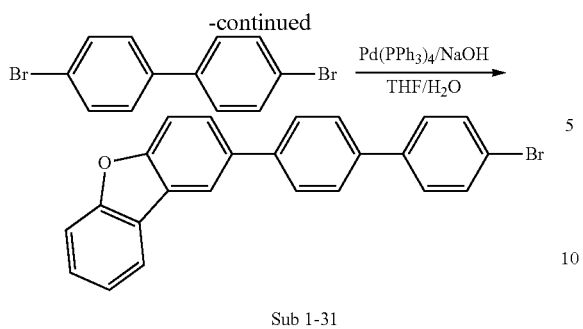

Sub 1-31

4,4'-dibromo-1,1'-biphenyl (14.76 g, 47.31 mmol), Pd(PPh₃)₄ (1.49 g, 1.29 mmol), NaOH (5.16 g, 129.02 mmol), THF (150 ml), water (75 ml) were added to Sub 1-II-27 (12.65 g, 43.01 mmol) obtained in the above synthesis, and then 13.57 g (yield: 79%) of the product was obtained by using the same manner as described above for the synthesis of Sub 1-3.

9. Synthesis Example of Sub 1-49

<Reaction Scheme 11>

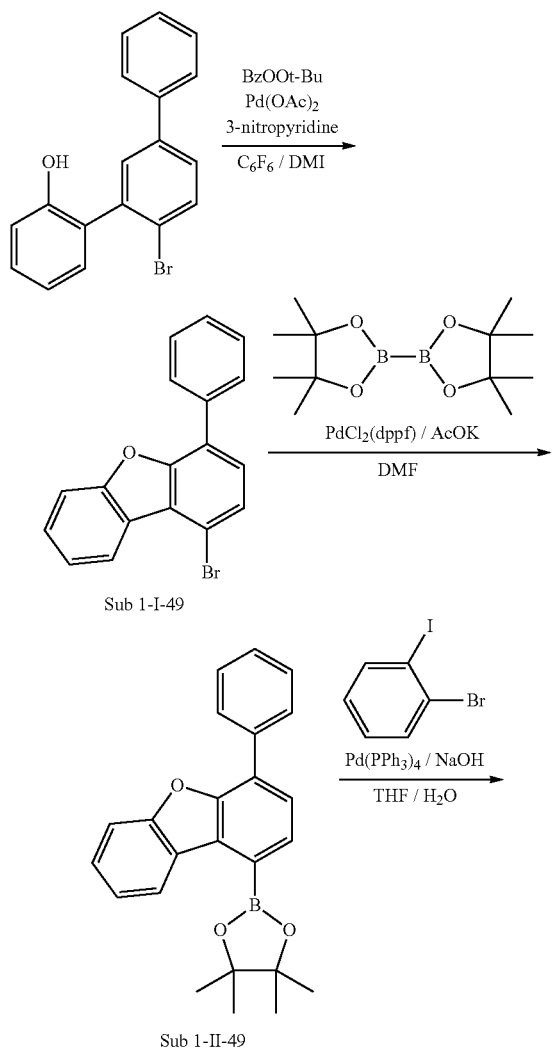

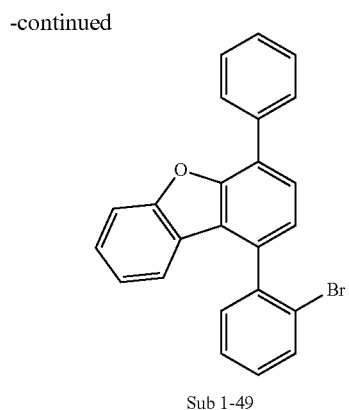

Sub 1-49

(1) Synthesis of Sub 1-I-49

Pd(OAc)₂ (3.59 g, 15.99 mmol), 3-nitropyridine (1.98 g, 15.99 mmol), tert-butyl peroxybenzoate (62.10 g, 319.74 mmol), C₆F₆ (240 ml), DMI (160 ml) were added to the starting material 6'-bromo-[1,1':3',1''-terphenyl]-2-ol (51.99 g, 159.87 mmol), and then 23.25 g (yield: 45%) of the product was obtained by using the same manner as described above for the synthesis of Sub 1-I-3.

(2) Synthesis of Sub 1-II-49

Bis(pinacolato)diboron (20.10 g, 79.14 mmol), Pd(dppf)Cl₂ (1.76 g, 2.16 mmol), KOAc (21.18 g, 215.82 mmol), DMF (360 ml) were added to Sub 1-I-49 (23.25 g, 71.94 mmol) obtained in the above synthesis, and then 21.31 g (yield: 80%) of the product was obtained by using the same manner as described above for the synthesis of Sub 1-II-3.

(3) Synthesis of Sub 1-49

1-bromo-2-iodobenzene (17.43 g, 61.62 mmol), Pd(PPh₃)4 (1.94 g, 1.68 mmol), NaOH (6.72 g, 168.05 mmol), THF (200 ml), water (100 ml) were added to Sub 1-II-49 (20.74 g, 56.02 mmol) obtained in the above synthesis, and then 15.21 g (yield: 68%) of the product was obtained by using the same manner as described above for the synthesis of Sub 1-3.

The compound belonging to Sub 1 may be, but not limited to, the following compounds, and Table 1 shows FD-MS (Field Desorption-Mass Spectrometry) values of compounds belonging to Sub 1.

Sub 1-2
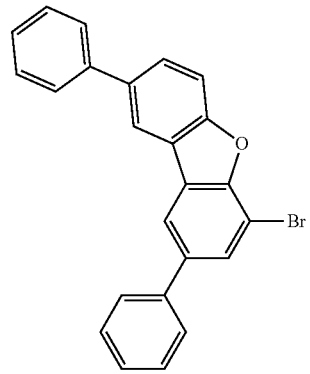
Sub 1-7
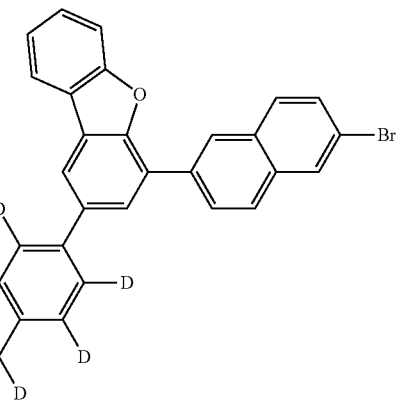
Sub 1-3
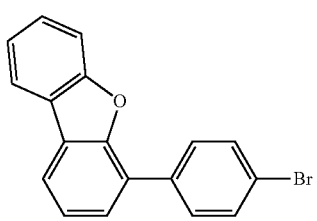
Sub 1-8
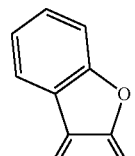
Sub 1-4
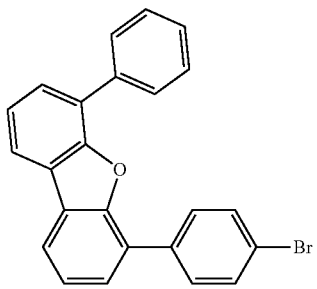
Sub 1-9
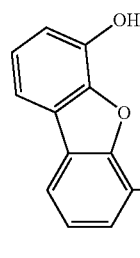
Sub 1-5
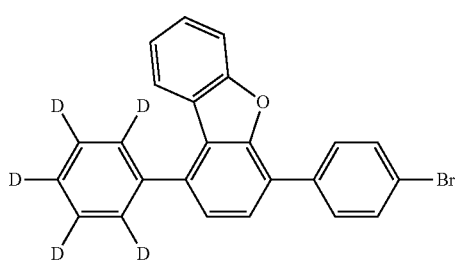
Sub 1-10
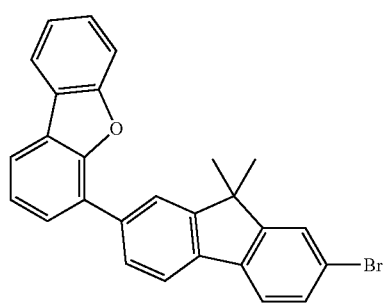
Sub 1-6
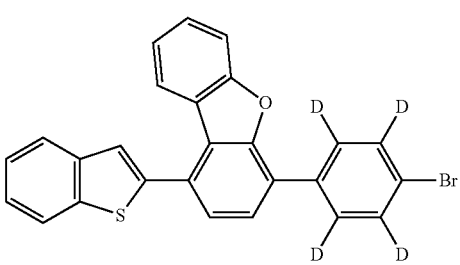

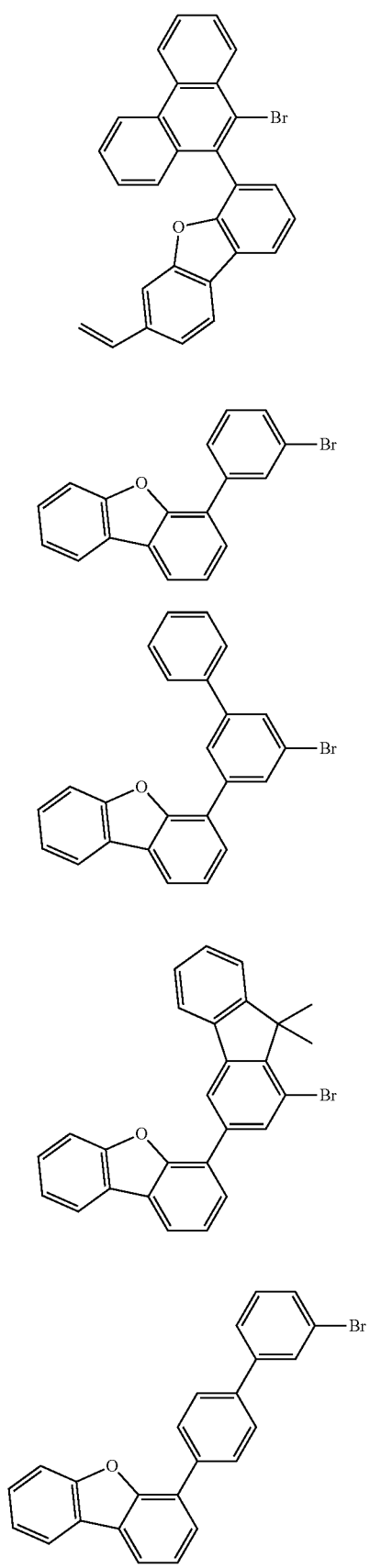
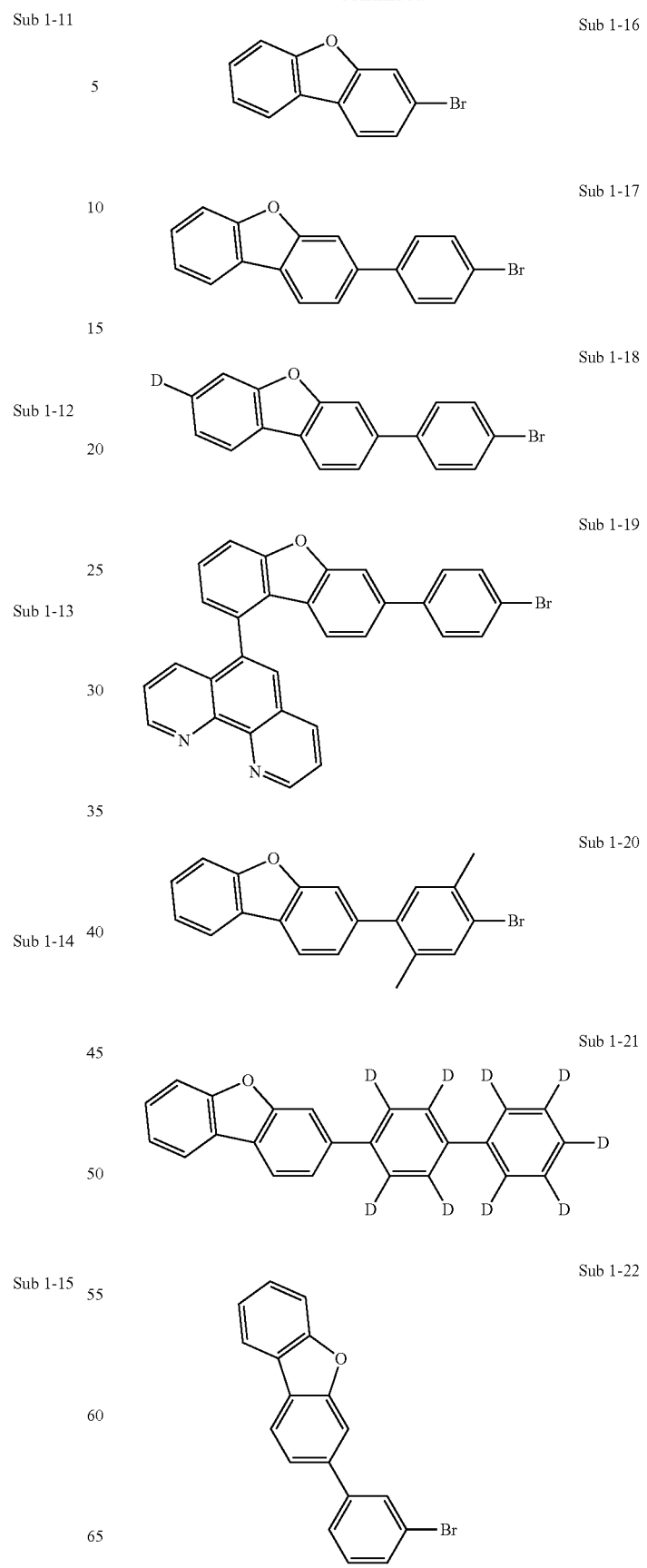

Sub 1-23
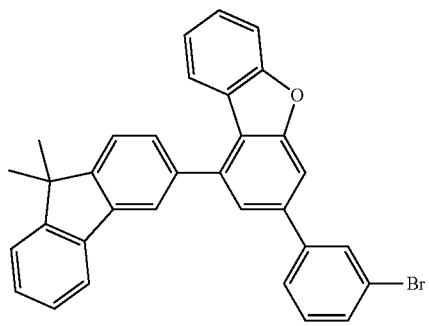
Sub 1-24
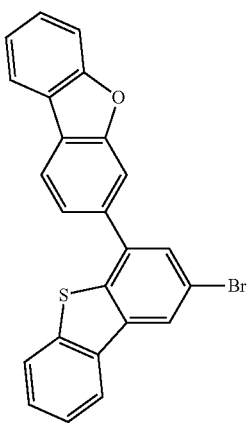
Sub 1-25
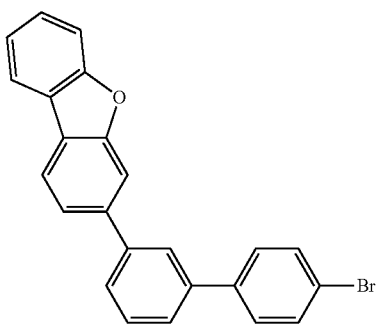
Sub 1-26
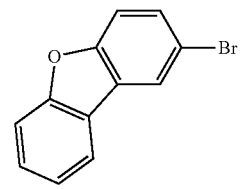
Sub 1-27
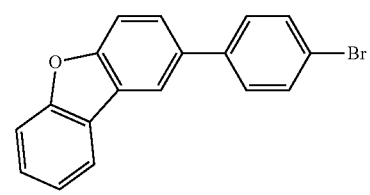
Sub 1-28
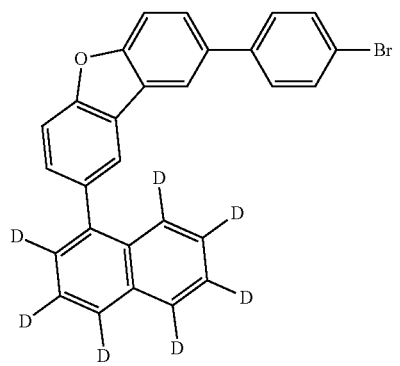
Sub 1-29
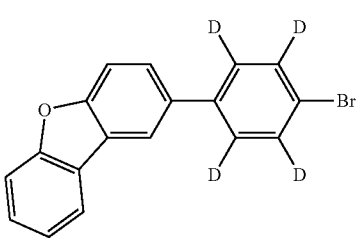
Sub 1-30
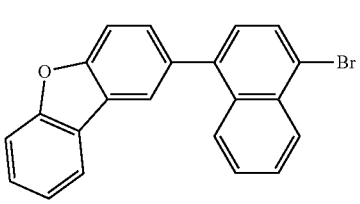
Sub 1-31
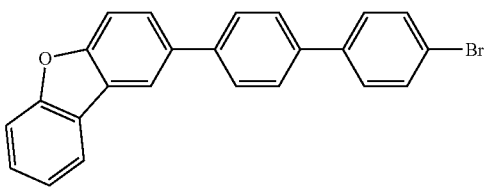
Sub 1-32
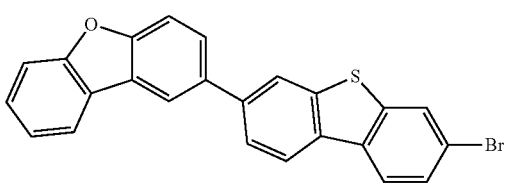
Sub 1-33
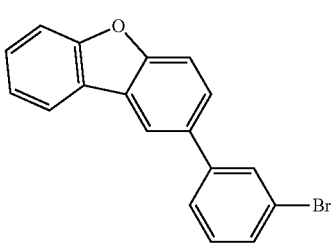

Sub1-34
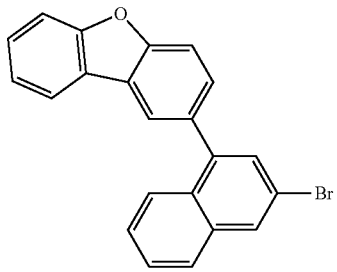
Sub 1-35
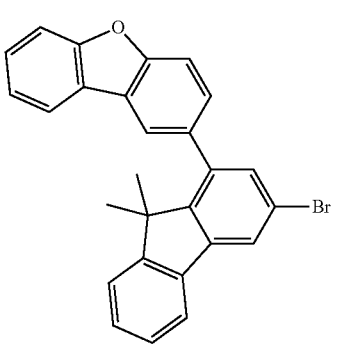
Sub 1-36
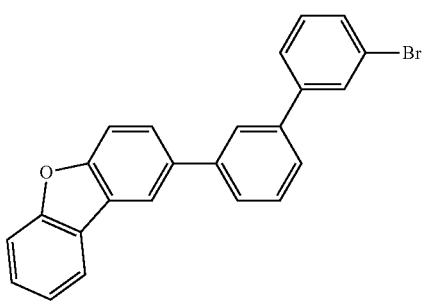
Sub-1-37
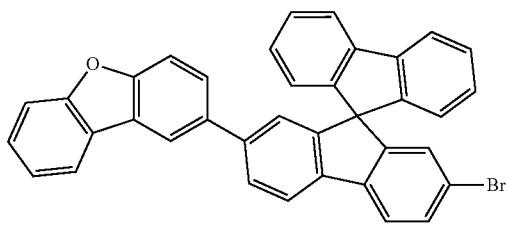
Sub 1-38
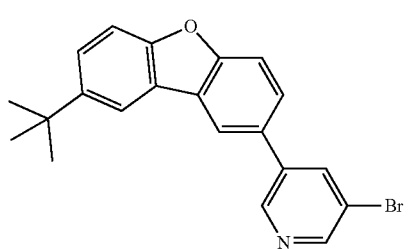
Sub 1-39
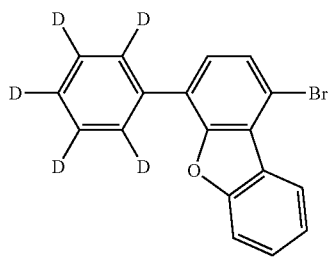
Sub 1-40
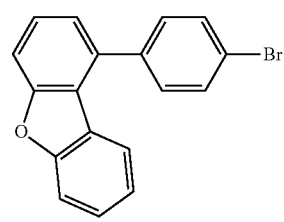
Sub 1-41
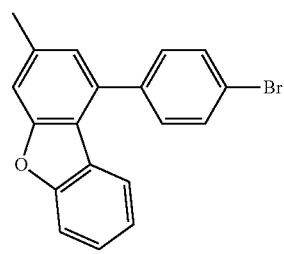
Sub 1-42
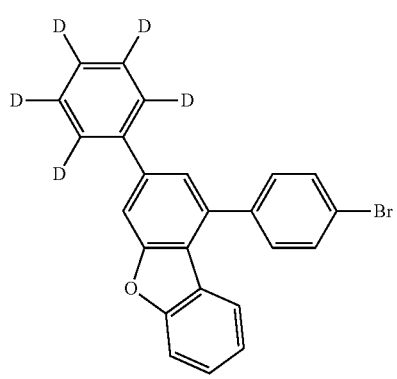
Sub 1-43
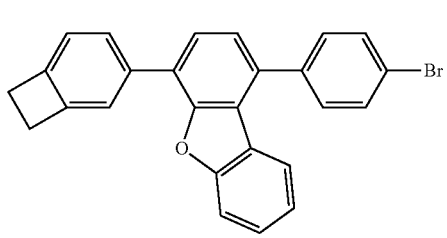

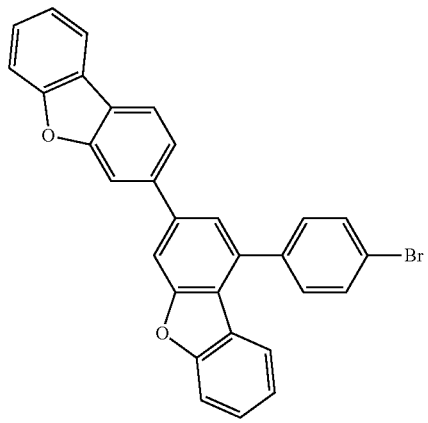

Sub 1-44

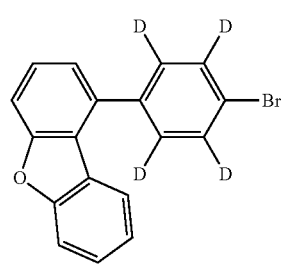

Sub 1-45

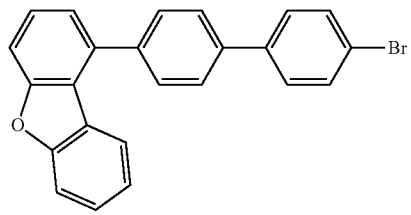

Sub 1-46

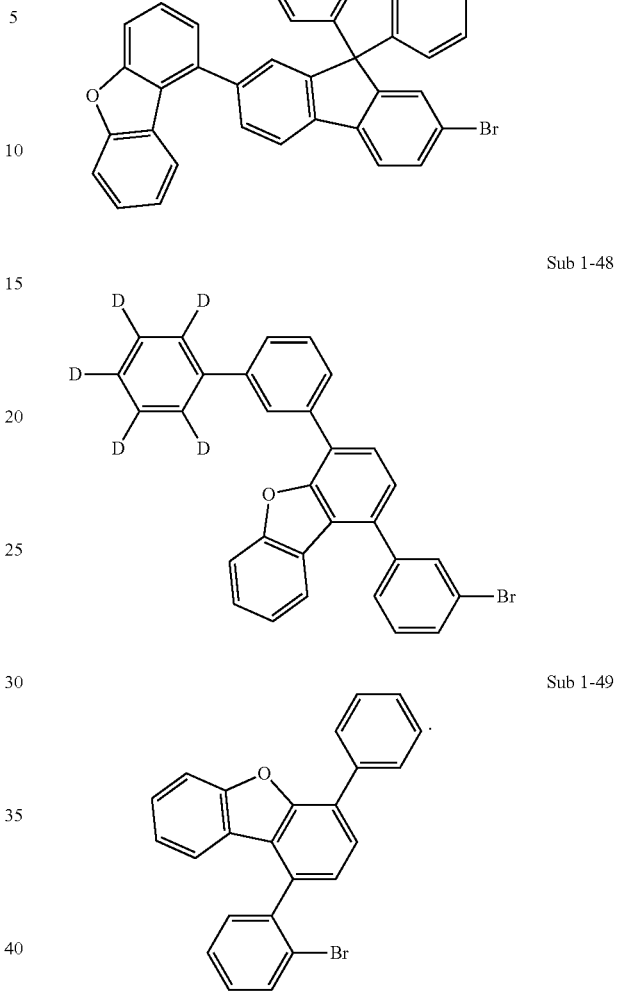

Sub 1-47

Sub 1-48

Sub 1-49

TABLE 1

| compound | FD-MS | compound | FD-MS |
| --- | --- | --- | --- |
| Sub1-1 | m/z = 245.97($C_{12}H_7BrO$ = 247.09) | Sub1-2 | m/z = 398.03($C_{24}H_{15}BrO$ = 399.28) |
| Sub1-3 | m/z = 322.00($C_{18}H_{11}BrO$ = 323.18) | Sub1-4 | m/z = 398.03($C_{24}H_{15}BrO$ = 399.28) |
| Sub1-5 | m/z = 403.06($C_{24}H_{10}D_5BrO$ = 404.31) | Sub1-6 | m/z = 458.03($C_{26}H_{11}D_4BrOS$ = 459.39) |
| Sub1-7 | m/z = 505.11($C_{32}H_{12}D_7BrO$ = 506.44) | Sub1-8 | m/z = 398.03($C_{24}H_{15}BrO$ = 399.28) |
| Sub1-9 | m/z = 477.07($C_{29}H_{12}D_4BrNO$ = 478.37) | Sub1-10 | m/z = 438.06($C_{27}H_{19}BrO$ = 439.34) |
| Sub1-11 | m/z = 448.05($C_{28}H_{17}BrO$ = 449.34) | Sub1-12 | m/z = 322.00($C_{18}H_{11}BrO$ = 323.18) |
| Sub1-13 | m/z = 398.03($C_{24}H_{15}BrO$ = 399.28) | Sub1-14 | m/z = 438.06($C_{27}H_{19}BrO$ = 439.34) |
| Sub1-15 | m/z = 398.03($C_{24}H_{15}BrO$ = 399.28) | Sub1-16 | m/z = 245.97($C_{12}H_7BrO$ = 247.09) |
| Sub1-17 | m/z = 322.00($C_{18}H_{11}BrO$ = 323.18) | Sub1-18 | m/z = 323.01($C_{18}H_{10}DBrO$ = 324.19) |
| Sub1-19 | m/z = 500.05($C_{30}H_{17}BrN_2O$ = 501.37) | Sub1-20 | m/z = 350.03($C_{20}H_{15}BrO$ = 351.24) |
| Sub1-21 | m/z = 406.08($C_{24}H_7D_8BrO$ = 407.33) | Sub1-22 | m/z = 322.00($C_{18}H_{11}BrO$ = 323.18) |
| Sub1-23 | m/z = 514.09($C_{33}H_{23}BrO$ = 515.44) | Sub1-24 | m/z = 427.99($C_{24}H_{13}BrOS$ = 429.33) |
| Sub1-25 | m/z = 398.03($C_{24}H_{15}BrO$ = 399.28) | Sub1-26 | m/z = 245.97($C_{12}H_7BrO$ = 247.09) |
| Sub1-27 | m/z = 322.00($C_{18}H_{11}BrO$ = 323.18) | Sub1-28 | m/z = 455.09($C_{28}H_{10}D_7BrO$ = 456.38) |
| Sub1-29 | m/z = 326.02($C_{18}H_7D_4BrO$ = 327.21) | Sub1-30 | m/z = 372.01($C_{22}H_{13}BrO$ = 373.24) |
| Sub1-31 | m/z = 398.03($C_{24}H_{15}BrO$ = 399.28) | Sub1-32 | m/z = 427.99($C_{24}H_{13}BrOS$ = 429.33) |
| Sub1-33 | m/z = 322.00($C_{18}H_{11}BrO$ = 323.18) | Sub1-34 | m/z = 372.01($C_{22}H_{13}BrO$ = 373.24) |
| Sub1-35 | m/z = 438.06($C_{27}H_{19}BrO$ = 439.34) | Sub1-36 | m/z = 398.03($C_{24}H_{15}BrO$ = 399.28) |
| Sub1-37 | m/z = 560.08($C_{37}H_{21}BrO$ = 561.47) | Sub1-38 | m/z = 379.06($C_{21}H_{18}BrNO$ = 380.28) |
| Sub1-39 | m/z = 327.03($C_{18}H_6BrO$ = 328.21) | Sub1-40 | m/z = 322.00($C_{18}H_{11}BrO$ = 323.18) |
| Sub1-41 | m/z = 336.01($C_{19}H_{13}BrO$ = 337.21) | Sub1-42 | m/z = 403.06($C_{24}H_{10}D_5BrO$ = 404.31) |
| Sub1-43 | m/z = 424.05($C_{26}H_{17}BrO$ = 425.32) | Sub1-44 | m/z = 488.04($C_{30}H_{17}BrO_2$ = 489.36) |
| Sub1-45 | m/z = 326.02($C_{18}H_7D_4BrO$ = 327.21) | Sub1-46 | m/z = 398.03($C_{24}H_{15}BrO$ = 399.28) |

TABLE 1-continued

| compound | FD-MS | compound | FD-MS |
|---|---|---|---|
| Sub1-47 | m/z = 562.09($C_{37}H_{23}BrO$ = 563.48) | Sub1-48 | m/z = 479.09($C_{30}H_{14}D_5BrO$ = 480.41) |
| Sub1-49 | m/z = 398.03($C_{24}H_{15}BrO$ = 399.28) | | |

II. Synthesis of Sub 2

Sub 2 of the Reaction Scheme 1 can be synthesized according to, but not limited to, the reaction route of the following Reaction Scheme 12.

<Reaction Scheme 12>

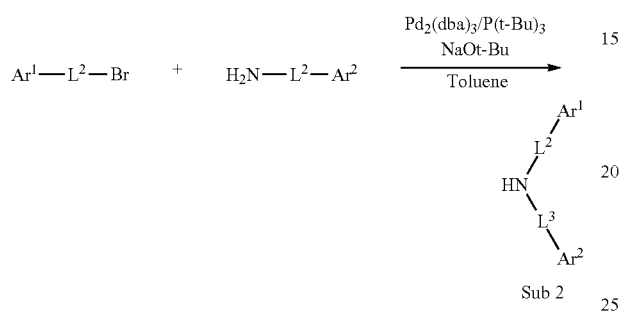

Sub 2

Synthesis Examples of compounds comprised in Sub 2 are as follows.

1. Synthesis Example of Sub 2-9

<Reaction Scheme 13>

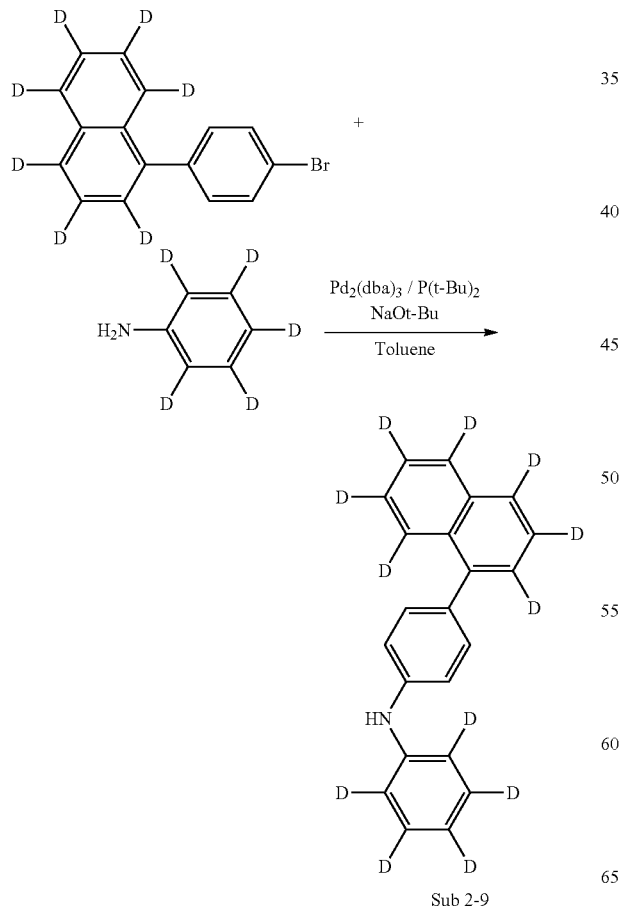

Sub 2-9

The starting material naphthalene-1,2,3,4,5,6,7-d7,8-(4-bromophenyl)-(13.67 g, 47.10 mmol) was dissolved in toluene (330 ml) in a round bottom flask, and then aniline-d5 (5.09 g, 51.81 mmol), $Pd_2(dba)_3$ (1.29 g, 1.41 mmol), 50% P(t-Bu)$_3$ (1.8 ml, 3.77 mmol), NaOt-Bu (13.58 g, 141.31 mmol) were added and stirred at 80° C. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 10.14 g (yield: 70%) of the product.

2. Synthesis Example of Sub 2-12

<Reaction Scheme 14>

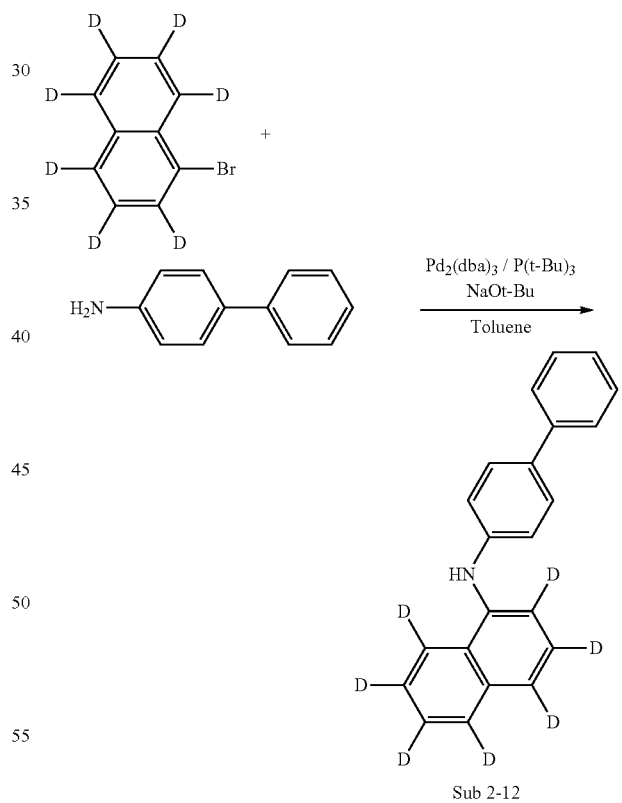

Sub 2-12

[1,1'-biphenyl]-4-amine (18.58 g, 109.79 mmol), $Pd_2(dba)_3$ (2.74 g, 2.99 mmol), 50% P(t-Bu)$_3$ (3.9 ml, 7.98 mmol), NaOt-Bu (28.78 g, 299.43 mmol), toluene (700 ml) were added to 1-bromonaphthalene-d7 (21.37 g, 99.81 mmol) obtained in the above synthesis, and then 21.43 g (yield: 71%) of the product was obtained by using the same manner as described above for the synthesis of Sub 2-9.

3. Synthesis Example of Sub 2-14

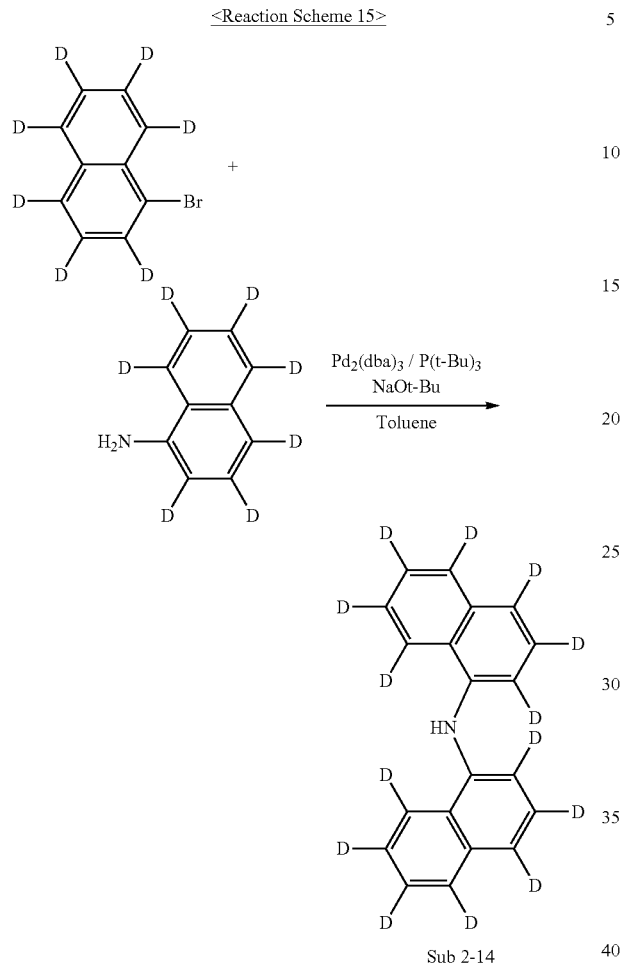

Sub 2-14

1-aminonaphthalene-d7 (9.46 g, 62.99 mmol), Pd$_2$(dba)$_3$ (1.57 g, 1.72 mmol), 50% P(t-Bu)$_3$ (2.2 ml, 4.58 mmol), NaOt-Bu (16.51 g, 171.78 mmol), toluene (400 ml) were added to 1-bromonaphthalene-d7 (12.26 g, 57.26 mmol) obtained in the above synthesis, and then 10.22 g (yield: 63%) of the product was obtained by using the same manner as described above for the synthesis of Sub 2-9.

4. Synthesis Example of Sub 2-15

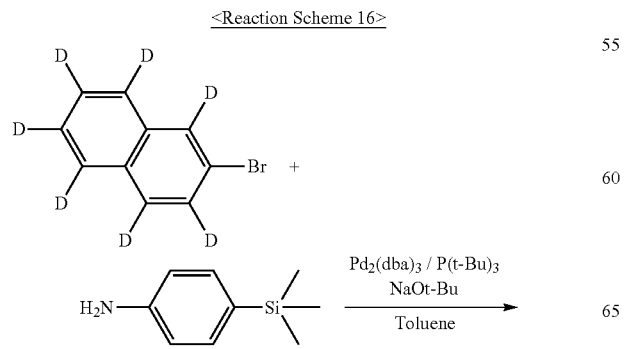

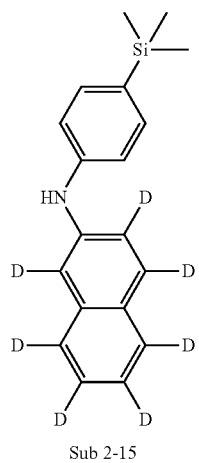

Sub 2-15

4-(trimethylsilyl)aniline (9.38 g, 56.72 mmol), Pd$_2$(dba)$_3$ (1.42 g, 1.55 mmol), 50% P(t-Bu)$_3$ (2.0 ml, 4.12 mmol), NaOt-Bu (14.87 g, 154.69 mmol), toluene (360 ml) were added to 2-bromonaphthalene-d7 (11.04 g, 51.56 mmol) obtained in the above synthesis, and then 10.47 g (yield: 68%) of the product was obtained by using the same manner as described above for the synthesis of Sub 2-9.

5. Synthesis Example of Sub 2-22

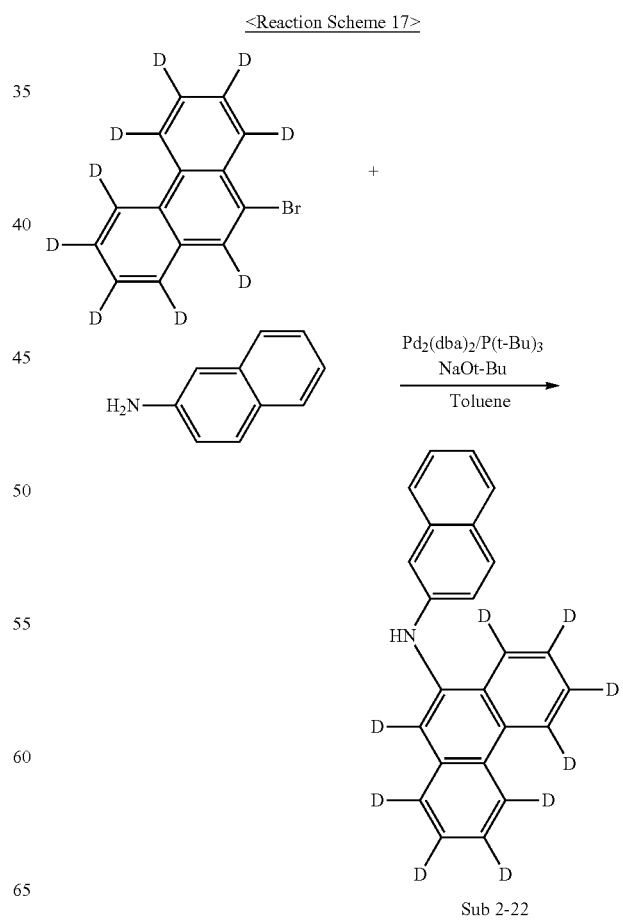

Sub 2-22

Naphthalen-2-amine (7.63 g, 53.27 mmol), Pd$_2$(dba)$_3$ (1.33 g, 1.45 mmol), 50% P(t-Bu)$_3$ (1.9 ml, 3.87 mmol), NaOt-Bu (13.96 g, 145.28 mmol), toluene (340 ml) were added to 9-bromophenanthrene-d9 (12.89 g, 48.43 mmol) obtained in the above synthesis, and then 10.34 g (yield: 65%) of the product was obtained by using the same manner as described above for the synthesis of Sub 2-9.

6. Synthesis Example of Sub 2-34

<Reaction Scheme 18>

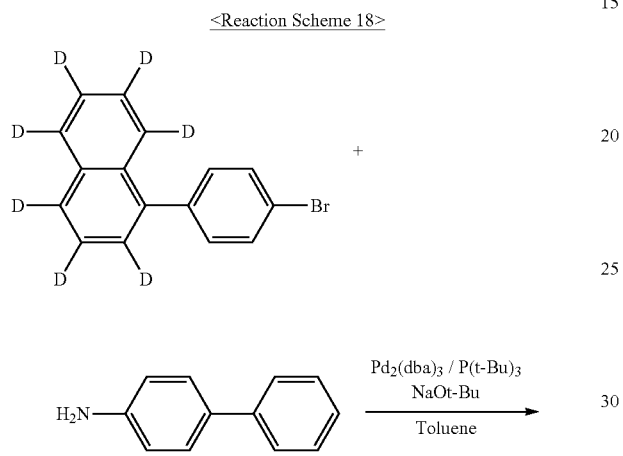

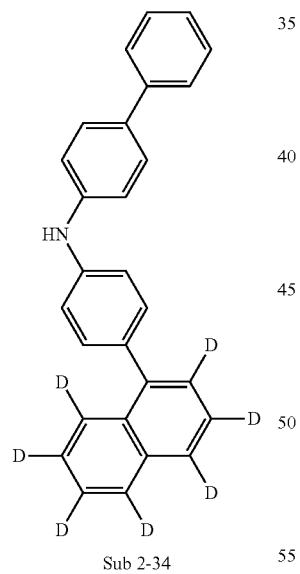

Sub 2-34

[1,1'-biphenyl]-4-amine (6.93 g, 40.97 mmol), Pd2(dba)$_3$ (1.02 g, 1.12 mmol), 50% P(t-Bu)$_3$ (1.5 ml, 2.98 mmol), NaOt-Bu (10.74 g, 111.75 mmol), toluene (260 ml) were added to naphthalene-1,2,3,4,5,6,7-d7,8-(4-bromophenyl) (10.81 g, 37.25 mmol) obtained in the above synthesis, and then 10.86 g (yield: 77%) of the product was obtained by using the same manner as described above for the synthesis of Sub 2-9.

7. Synthesis Example of Sub 2-43

<Reaction Scheme 19>

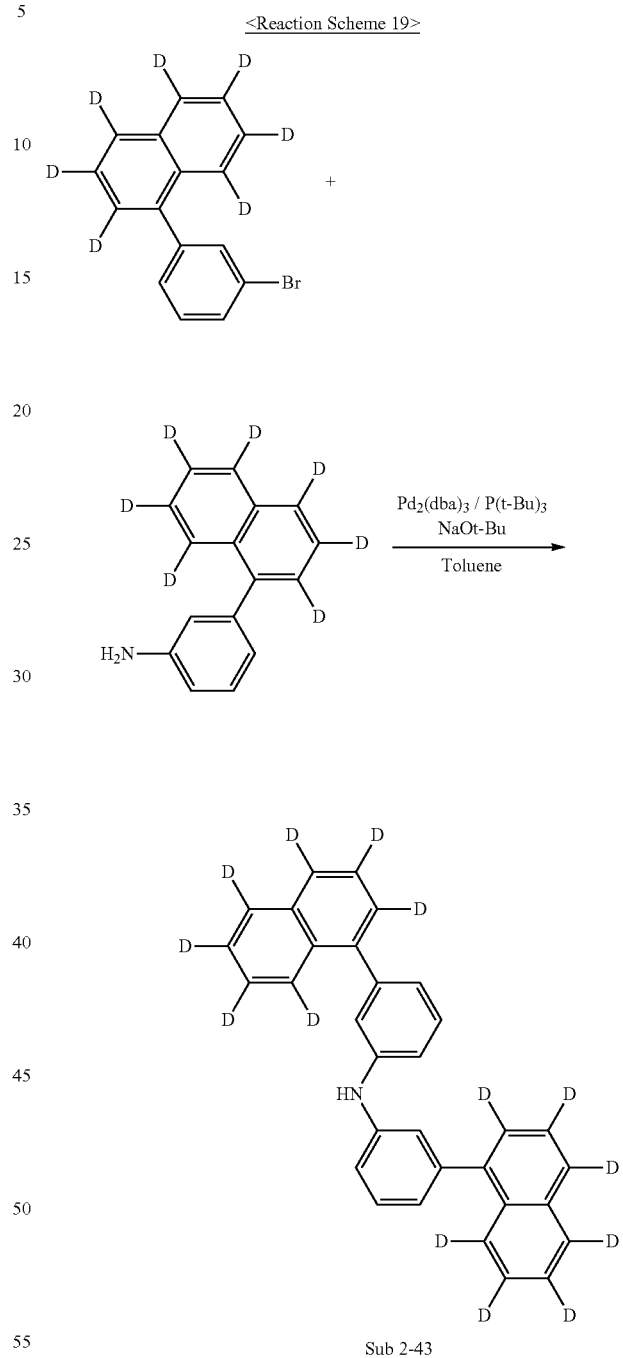

Sub 2-43

Naphthalene-1,2,3,4,5,6,7-d7,8-(3-aminophenyl) (7.95 g, 35.14 mmol), Pd$_2$(dba)$_3$ (0.88 g, 0.96 mmol), 50% P(t-Bu)$_3$ (1.2 ml, 2.56 mmol), NaOt-Bu (9.21 g, 95.83 mmol), toluene (225 ml) were added to naphthalene-1,2,3,4,5,6,7-d7,8-(3-bromophenyl) (9.27 g, 31.94 mmol) obtained in the above synthesis, and then 10.16 g (yield: 73%) of the product was obtained by using the same manner as described above for the synthesis of Sub 2-9.

8. Synthesis Example of Sub 2-48

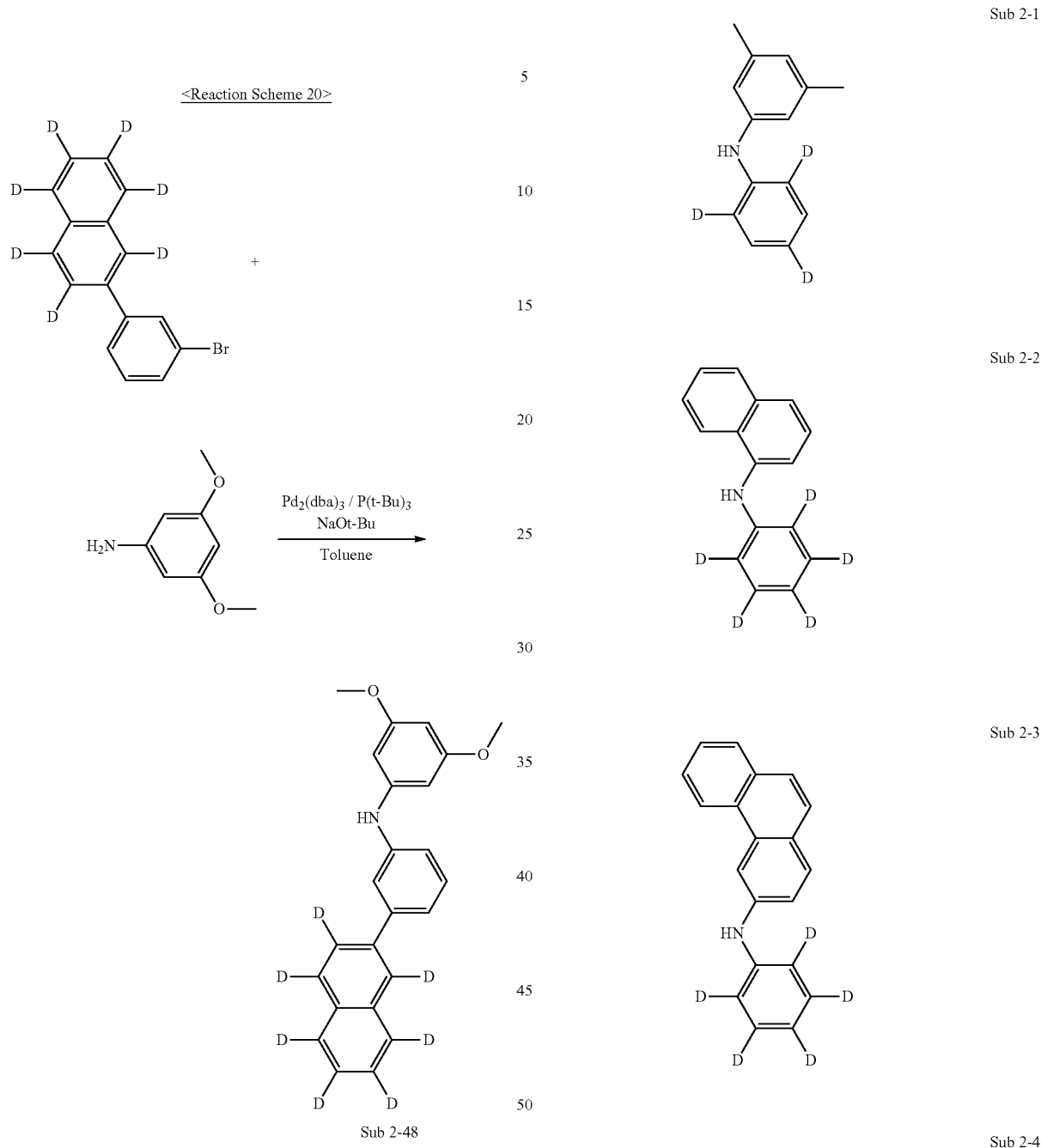

3,5-dimethoxyaniline (6.72 g, 43.89 mmol), Pd2(dba)3 (1.10 g, 1.20 mmol), 50% P(t-Bu)₃ (1.6 ml, 3.19 mmol), NaOt-Bu (11.50 g, 119.71 mmol), toluene (280 ml) were added to naphthalene-1,3,4,5,6,7,8-d7,2-(3-bromophenyl) (11.58 g, 39.90 mmol) obtained in the above synthesis, and then 9.98 g (yield: 69%) of the product was obtained by using the same manner as described above for the synthesis of Sub 2-9.

The compound belonging to Sub 2 may be, but not limited to, the following compounds, and Table 2 shows FD-MS values of compounds belonging to Sub 2.

-continued
Sub 2-5
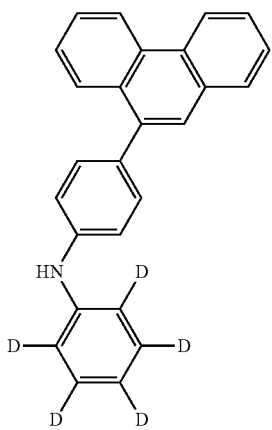
Sub 2-6
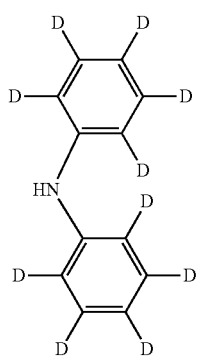
Sub 2-7
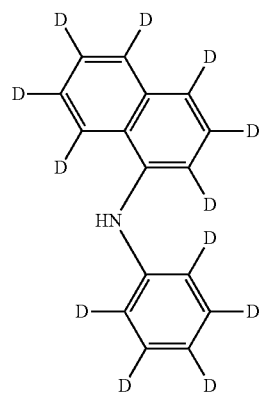
Sub 2-8
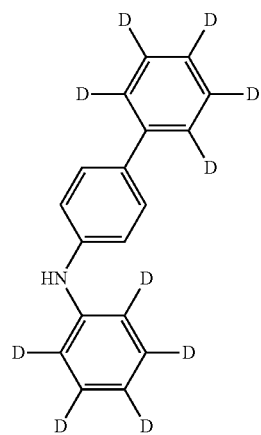
Sub 2-9
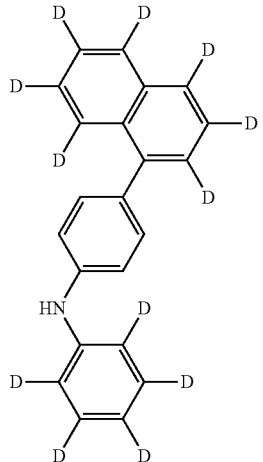
Sub 2-10
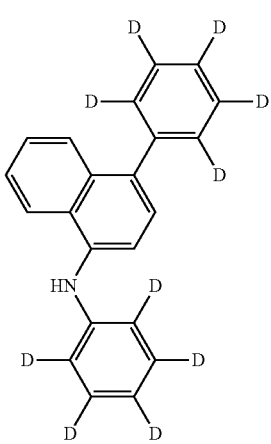
Sub 2-11
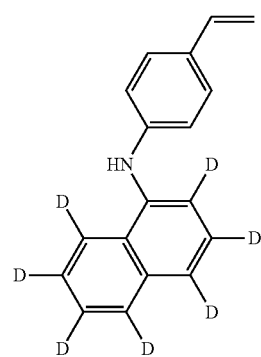

Sub 2-12
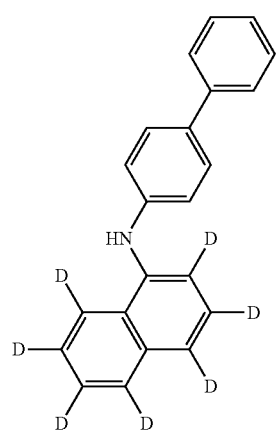
Sub 2-13
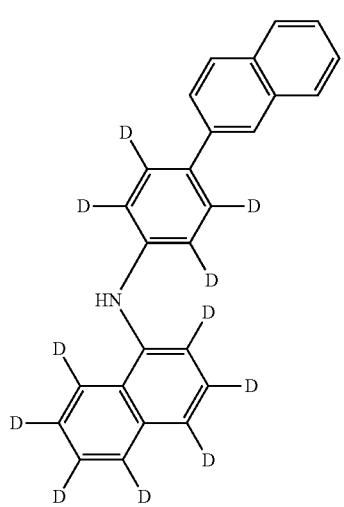
Sub 2-14
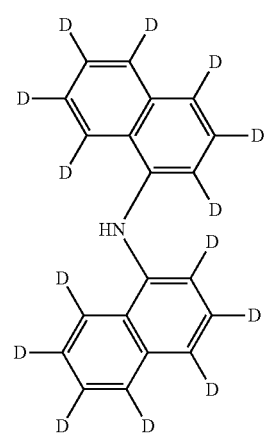
Sub 2-15
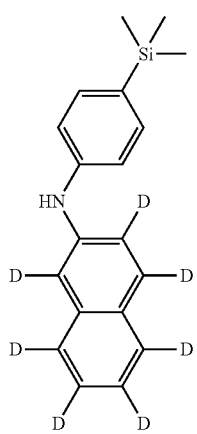
Sub 2-16
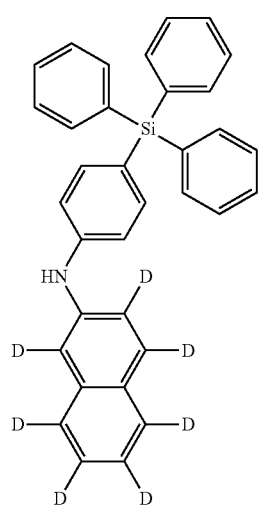
Sub 2-17
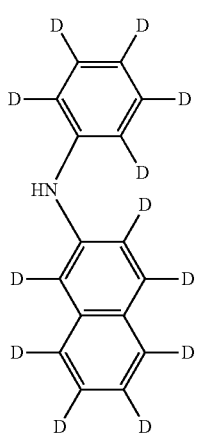

Sub 2-18
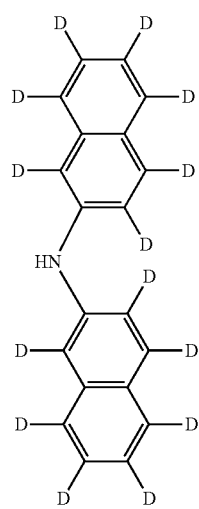
Sub 2-19
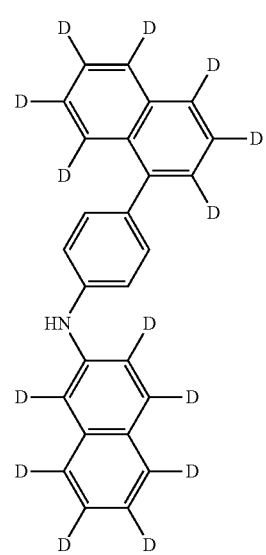
Sub 2-20
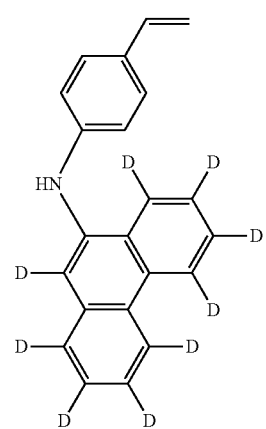
Sub 2-21
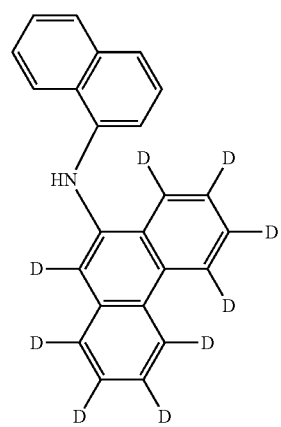
Sub 2-22
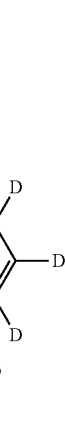
Sub 2-23
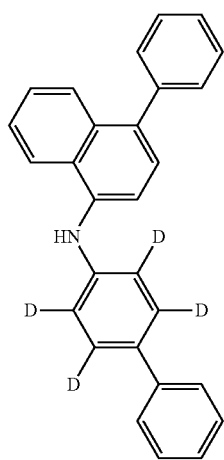

Sub 2-24
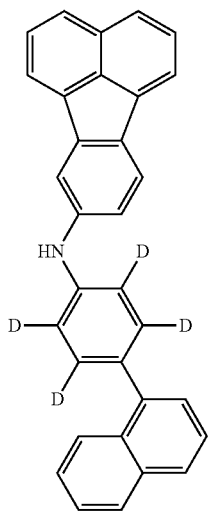
Sub 2-25
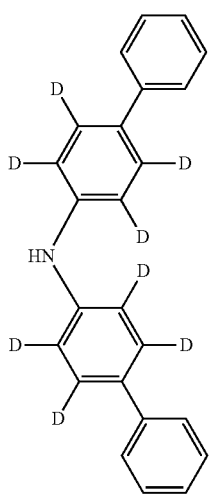
Sub 2-26
Sub 2-27
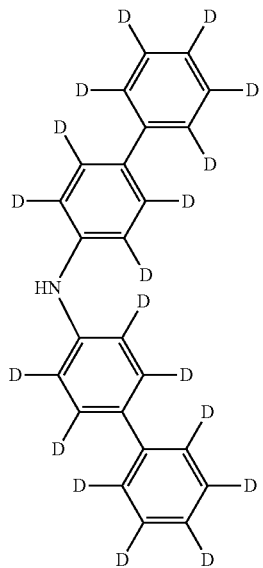
Sub 2-28
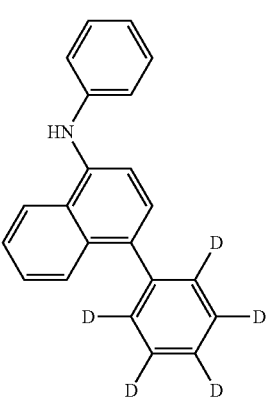
Sub 2-29
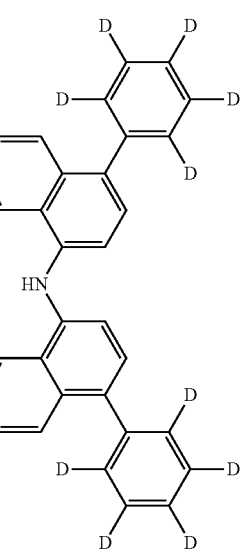

Sub 2-30
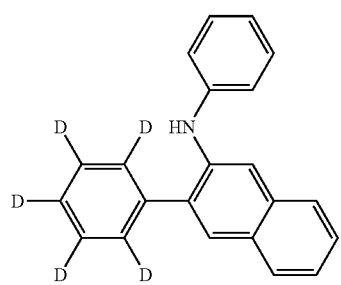
Sub 2-31
Sub 2-32
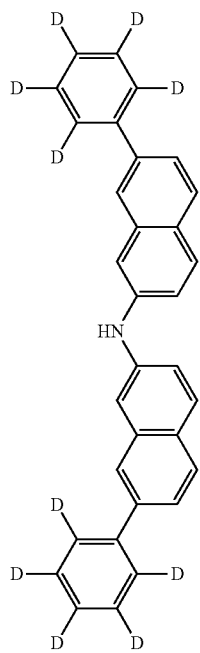
Sub 2-33
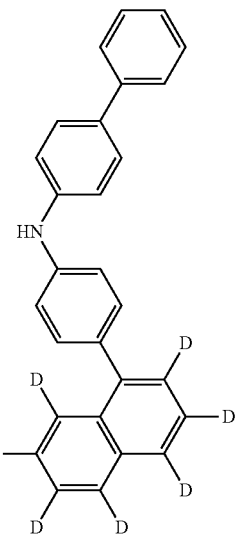
Sub 2-34
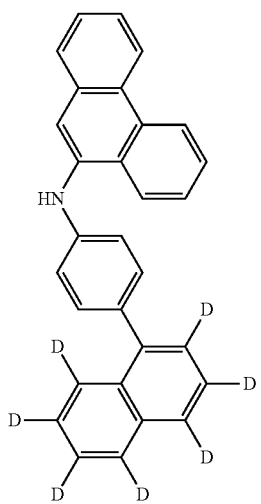
Sub 2-35

Sub 2-36
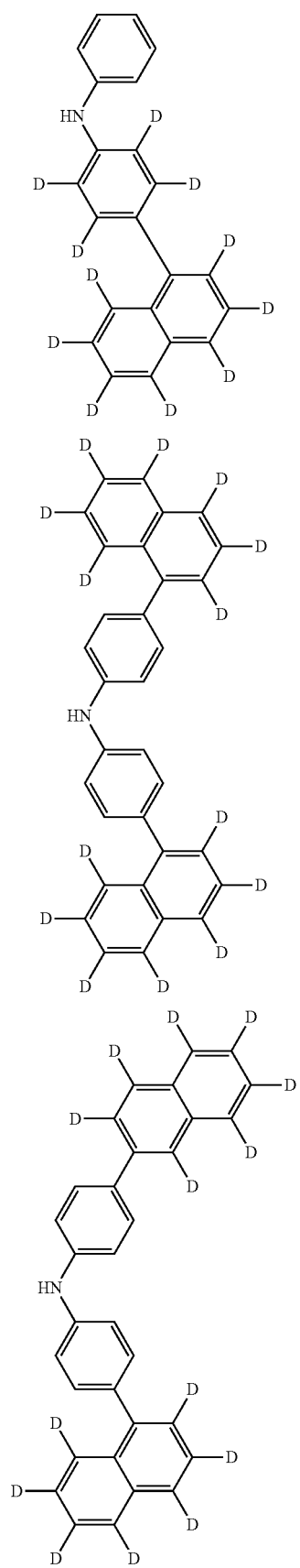
Sub 2-37
Sub 2-38
Sub 2-39
Sub 2-40

Sub 2-41
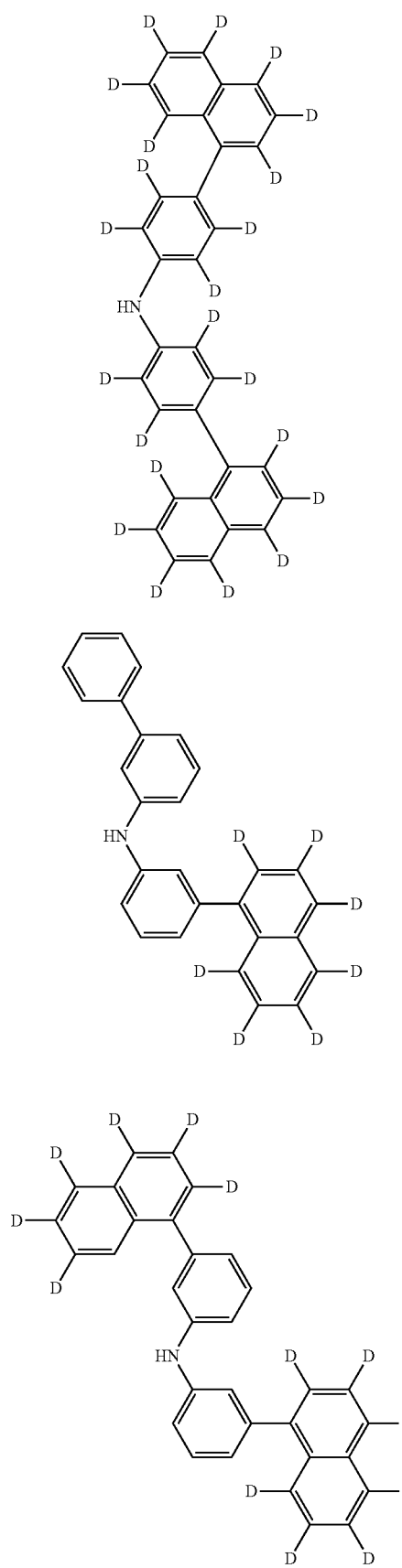
Sub 2-42
Sub 2-43
Sub 2-44
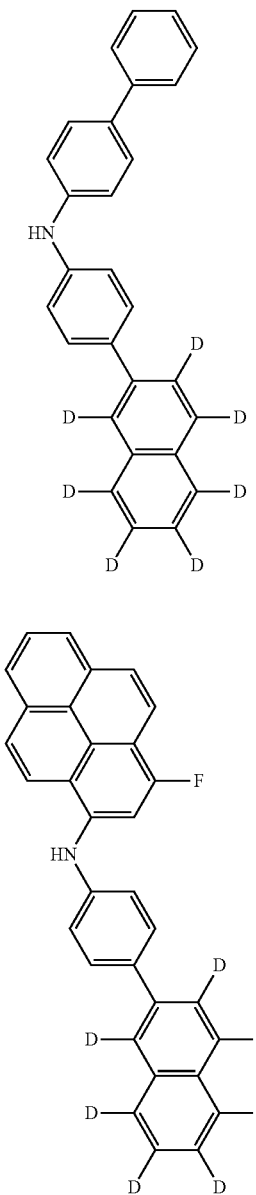
Sub 2-45
Sub 2-46

Sub 2-47

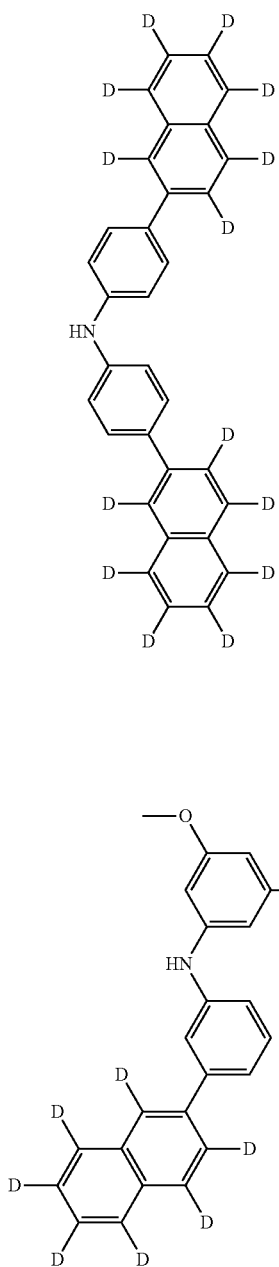

Sub 2-48

Sub 2-49

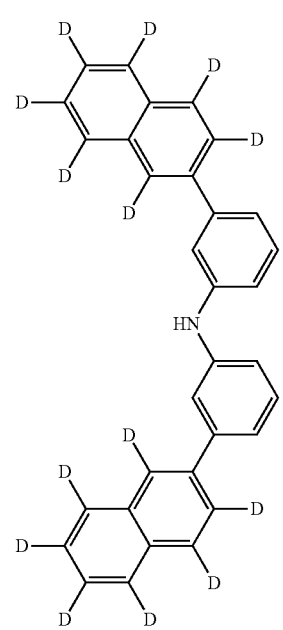

Sub 2-50

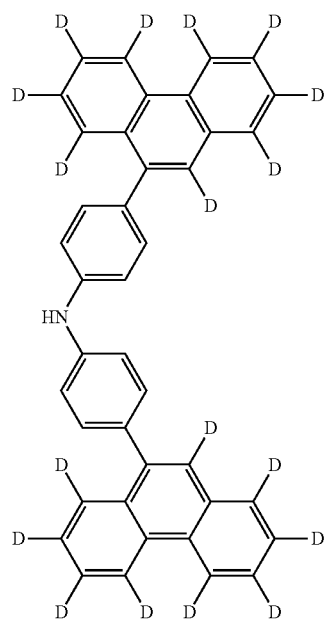

TABLE 2

| compound | FD-MS | compound | FD-MS |
| --- | --- | --- | --- |
| Sub2-1 | m/z = 200.14($C_{14}H_{12}D_3N$ = 200.29) | Sub2-2 | m/z = 224.14($C_{16}H_8D_5N$ = 224.31) |
| Sub2-3 | m/z = 274.15($C_{20}H_{10}D_5N$ = 274.37) | Sub2-4 | m/z = 250.15($C_{18}H_{10}D_5N$ = 250.35) |
| Sub2-5 | m/z = 350.18($C_{26}H_{14}D_5N$ = 350.47) | Sub2-6 | m/z = 179.15($C_{12}H_{10}N$ = 179.28) |
| Sub2-7 | m/z = 231.18($C_{16}HD_{12}N$ = 231.36) | Sub2-8 | m/z = 255.18($C_{18}H_5D_{10}N$ = 255.38) |
| Sub2-9 | m/z = 307.21($C_{22}H_5D_{12}N$ = 307.45) | Sub2-10 | m/z = 305.20($C_{22}H_7D_{10}N$ = 305.44) |
| Sub2-11 | m/z = 252.16($C_{18}H_8D_7N$ = 252.36) | Sub2-12 | m/z = 302.18($C_{22}H_{10}D_7N$ = 302.42) |
| Sub2-13 | m/z = 356.22($C_{26}H_8D_{11}N$ = 356.50) | Sub2-14 | m/z = 283.21($C_{20}HD_{14}N$ = 283.43) |
| Sub2-15 | m/z = 298.19($C_{19}H_{14}D_7NSi$ = 298.51) | Sub2-16 | m/z = 484.24($C_{34}H_{20}D_7NSi$ = 484.71) |
| Sub2-17 | m/z = 231.18($C_{16}HD_{12}N$ = 231.36) | Sub2-18 | m/z = 283.21($C_{20}HD_{14}N$ = 283.43) |
| Sub2-19 | m/z = 359.24($C_{26}H_5D_{14}N$ = 359.52) | Sub2-20 | m/z = 304.19($C_{22}H_8D_9N$ = 304.43) |
| Sub2-21 | m/z = 328.19($C_{24}H_8D_9N$ = 328.45) | Sub2-22 | m/z = 328.19($C_{24}H_8D_9N$ = 328.45) |
| Sub2-23 | m/z = 375.19($C_{28}H_{17}D_4N$ = 375.50) | Sub2-24 | m/z = 423.19($C_{32}H_{17}D_4N$ = 423.54) |
| Sub2-25 | m/z = 329.20($C_{24}H_{11}D_8N$ = 329.46) | Sub2-26 | m/z = 330.21($C_{24}H_{10}D_9N$ = 330.47) |
| Sub2-27 | m/z = 339.26($C_{24}HD_{18}N$ = 339.53) | Sub2-28 | m/z = 300.17($C_{22}H_{12}D_5N$ = 300.41) |

TABLE 2-continued

| compound | FD-MS | compound | FD-MS |
|---|---|---|---|
| Sub2-29 | m/z = 431.25($C_{32}H_{13}D_{10}N$ = 431.59) | Sub2-30 | m/z = 300.17($C_{22}H_{12}D_5N$ = 300.41) |
| Sub2-31 | m/z = 314.18($C_{23}H_{14}D_5N$ = 314.43) | Sub2-32 | m/z = 431.25($C_{32}H_{13}D_{10}N$ = 431.59) |
| Sub2-33 | m/z = 431.25($C_{32}H_{13}D_{10}N$ = 431.59) | Sub2-34 | m/z = 378.21($C_{28}H_{14}D_7N$ = 378.52) |
| Sub2-35 | m/z = 402.21($C_{30}H_{14}D_7N$ = 402.54) | Sub2-36 | m/z = 306.21($C_{22}H_6D_{11}N$ = 306.44) |
| Sub2-37 | m/z = 435.27($C_{32}H_9D_{14}N$ = 435.62) | Sub2-38 | m/z = 435.27($C_{32}H_9D_{14}N$ = 435.62) |
| Sub2-39 | m/z = 387.27($C_{28}H_5D_{16}N$ = 387.57) | Sub2-40 | m/z = 387.27($C_{28}H_5D_{16}N$ = 387.57) |
| Sub2-41 | m/z = 443.32($C_{32}HD_{22}N$ = 443.67) | Sub2-42 | m/z = 378.21($C_{28}H_{14}D_7N$ = 378.52) |
| Sub2-43 | m/z = 435.27($C_{32}H_9D_{14}N$ = 435.62) | Sub2-44 | m/z = 378.21($C_{28}H_{14}D_7N$ = 378.52) |
| Sub2-45 | m/z = 444.20($C_{32}H_{13}D_7FN$ = 444.55) | Sub2-46 | m/z = 352.20($C_{26}H_{12}D_7N$ = 352.48) |
| Sub2-47 | m/z = 435.27($C_{32}H_9D_{14}N$ = 435.62) | Sub2-48 | m/z = 362.20($C_{24}H_{14}D_7NO_2$ = 362.47) |
| Sub2-49 | m/z = 435.27($C_{32}H_9D_{14}N$ = 435.62) | Sub2-50 | m/z = 539.33($C_{40}H_9D_{18}N$ = 539.76) |

III. Synthesis of Final Products

Sub 1 (1 eq.) was dissolved in toluene in a round bottom flask, and Sub 2 (1 eq.), $Pd_2(dba)_3$ (0.03 eq.), $P(t\text{-}Bu)_h$ (0.08 eq.) and NaOt-Bu (3 eq.) were added, then, stirring at 100☐ was followed. When the reaction was completed, the reaction product was extracted with $CH_2Cl_2$ and water, and then the organic layer was dried with $MgSO_4$ and concentrated. Then, the concentrate was passed through silica gel column and recrystallized to obtain final product.

1. Synthesis Example of P-3

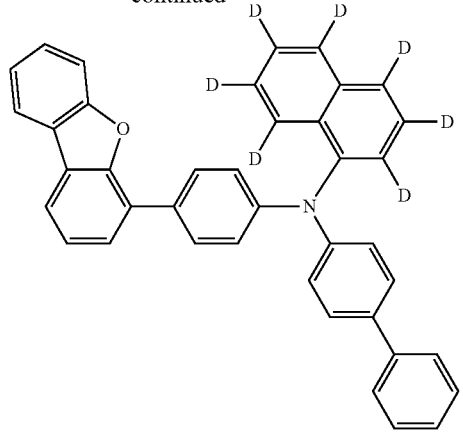

P-3

Sub 1-3 (5.42 g, 16.77 mmol) obtained in the above synthesis was dissolved in toluene (170 ml) in a round bottom flask, and Sub 2-12 (5.07 g, 16.77 mmol), $Pd_2(dba)_3$ (0.46 g, 0.50 mmol), 50% $P(t\text{-}Bu)_3$ (0.7 ml, 1.34 mmol), NaOt-Bu (4.84 g, 50.31 mmol) were added, then, stirring at 100° C. was followed. When the reaction was completed, the reaction product was extracted with $CH_2Cl_2$ and water, and then the organic layer was dried with $MgSO_4$ and concentrated. Then, the concentrate was passed through silica gel column and recrystallized to obtain 7.67 g (yield: 84%) of product.

2. Synthesis Example of P-7

<Reaction Scheme 22>

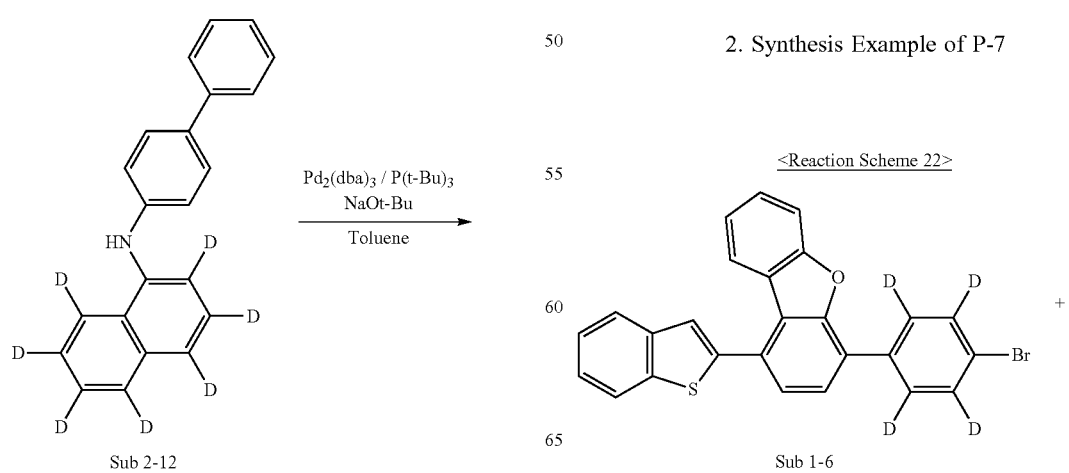

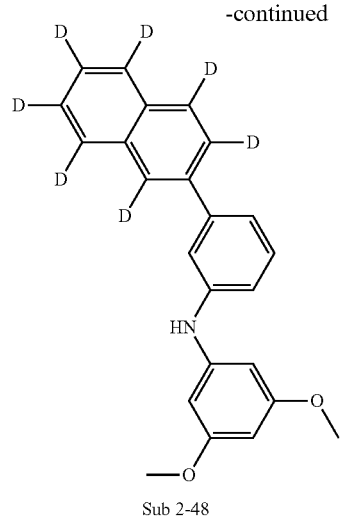

Sub 2-48

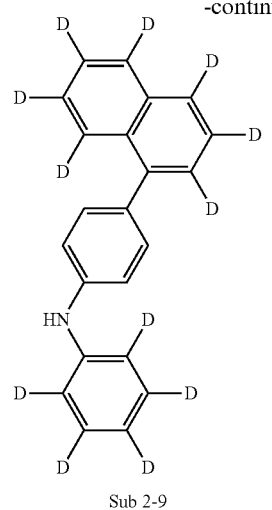

Sub 2-9

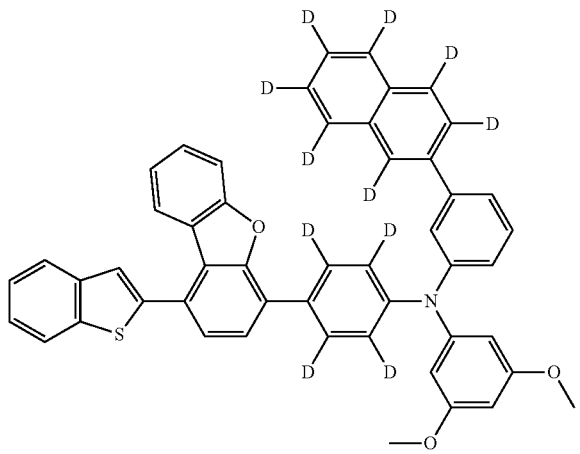

P-7

P-11

Sub 2-48 (5.14 g, 14.17 mmol), Pd$_2$(dba)$_3$ (0.39 g, 0.43 mmol), 50% P(t-Bu)$_3$ (0.6 ml, 1.13 mmol), NaOt-Bu (4.09 g, 42.51 mmol), toluene (140 ml) were added to Sub 1-6 (6.51 g, 14.17 mmol) obtained in the above synthesis, and then 7.03 g (yield: 67%) of the product was obtained by using the same manner as described above for the synthesis of the compound P-3.

3. Synthesis Example of P-11

Sub 2-9 (4.60 g, 14.98 mmol), Pd$_2$(dba)$_3$ (0.41 g, 0.45 mmol), 50% P(t-Bu)$_3$ (0.6 ml, 1.20 mmol), NaOt-Bu (4.32 g, 44.93 mmol), toluene (150 ml) were added to Sub 1-10 (6.58 g, 14.98 mmol) obtained in the above synthesis, and then 7.48 g (yield: 75%) of the product was obtained by using the same manner as described above for the synthesis of the compound P-3.

4. Synthesis Example of P-25

<Reaction Scheme 23>

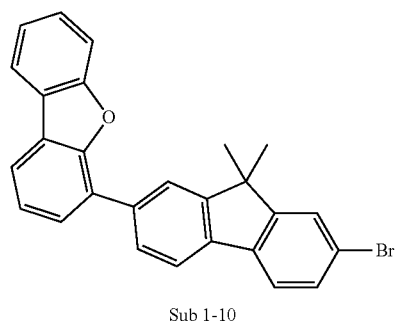

Sub 1-10

<Reaction Scheme 24>

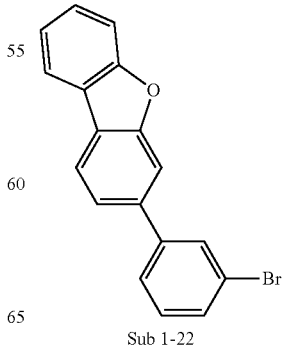

Sub 1-22

+

+

81
-continued

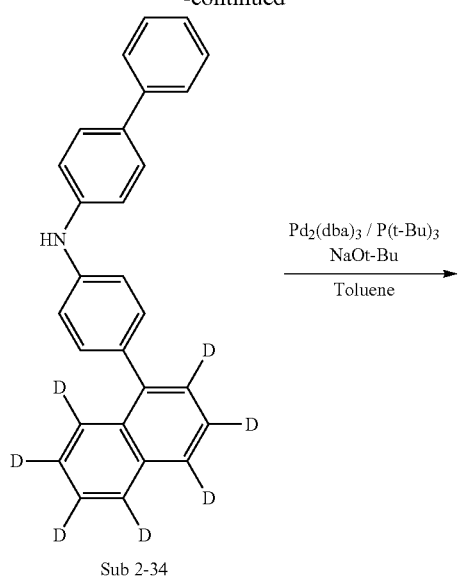

Sub 2-34

82
5. Synthesis Example of P-27

<Reaction Scheme 25>

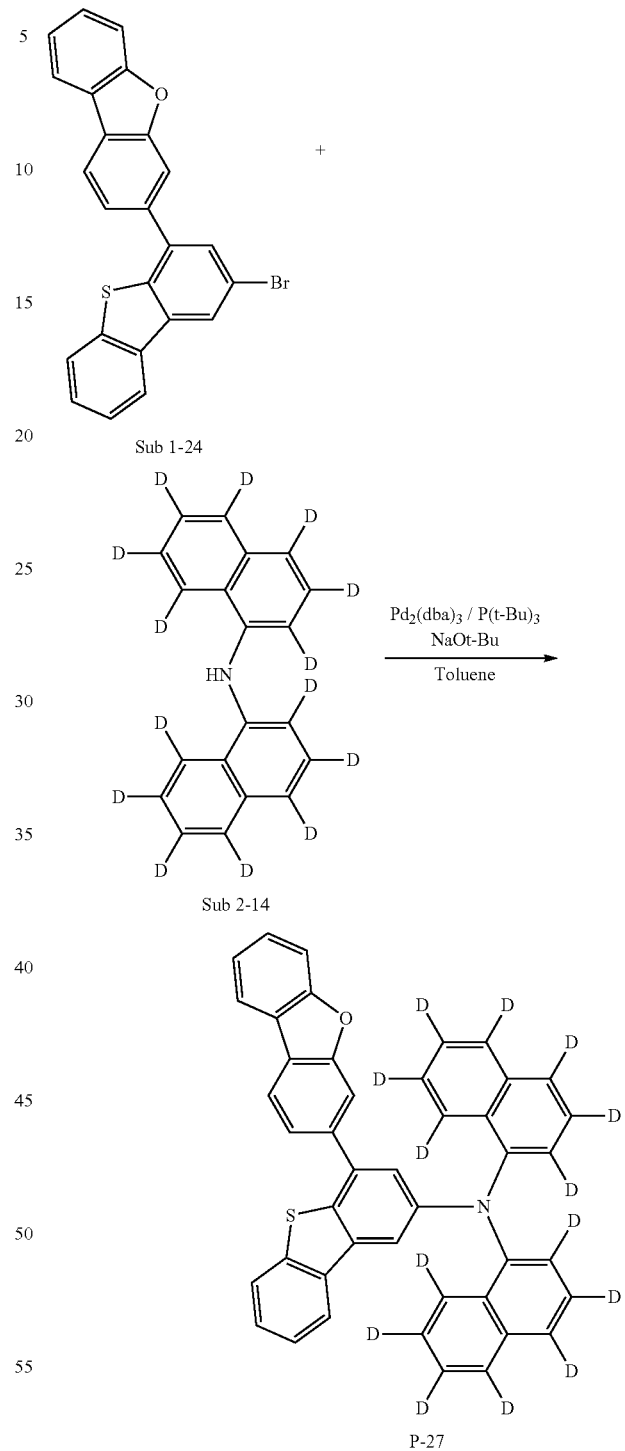

Sub 2-34 (5.69 g, 15.04 mmol), Pd₂(dba)₃ (0.41 g, 0.45 mmol), 50% P(t-Bu)₃ (0.6 ml, 1.20 mmol), NaOt-Bu (4.34 g, 45.11 mmol), toluene (150 ml) were added to Sub 1-22 (4.86 g, 15.04 mmol) obtained in the above synthesis, and then 7.66 g (yield: 82%) of the product was obtained by using the same manner as described above for the synthesis of the compound P-3.

Sub 2-14 (4.57 g, 16.14 mmol), Pd₂(dba)₃ (0.44 g, 0.48 mmol), 50% P(t-Bu)₃ (0.6 ml, 1.29 mmol), NaOt-Bu (4.65 g, 48.42 mmol), toluene (160 ml) were added to Sub 1-24 (6.93 g, 16.14 mmol) obtained in the above synthesis, and then 7.24 g (yield: 71%) of the product was obtained by using the same manner as described above for the synthesis of the compound P-3.

6. Synthesis Example of P-30

7. Synthesis Example of P-34

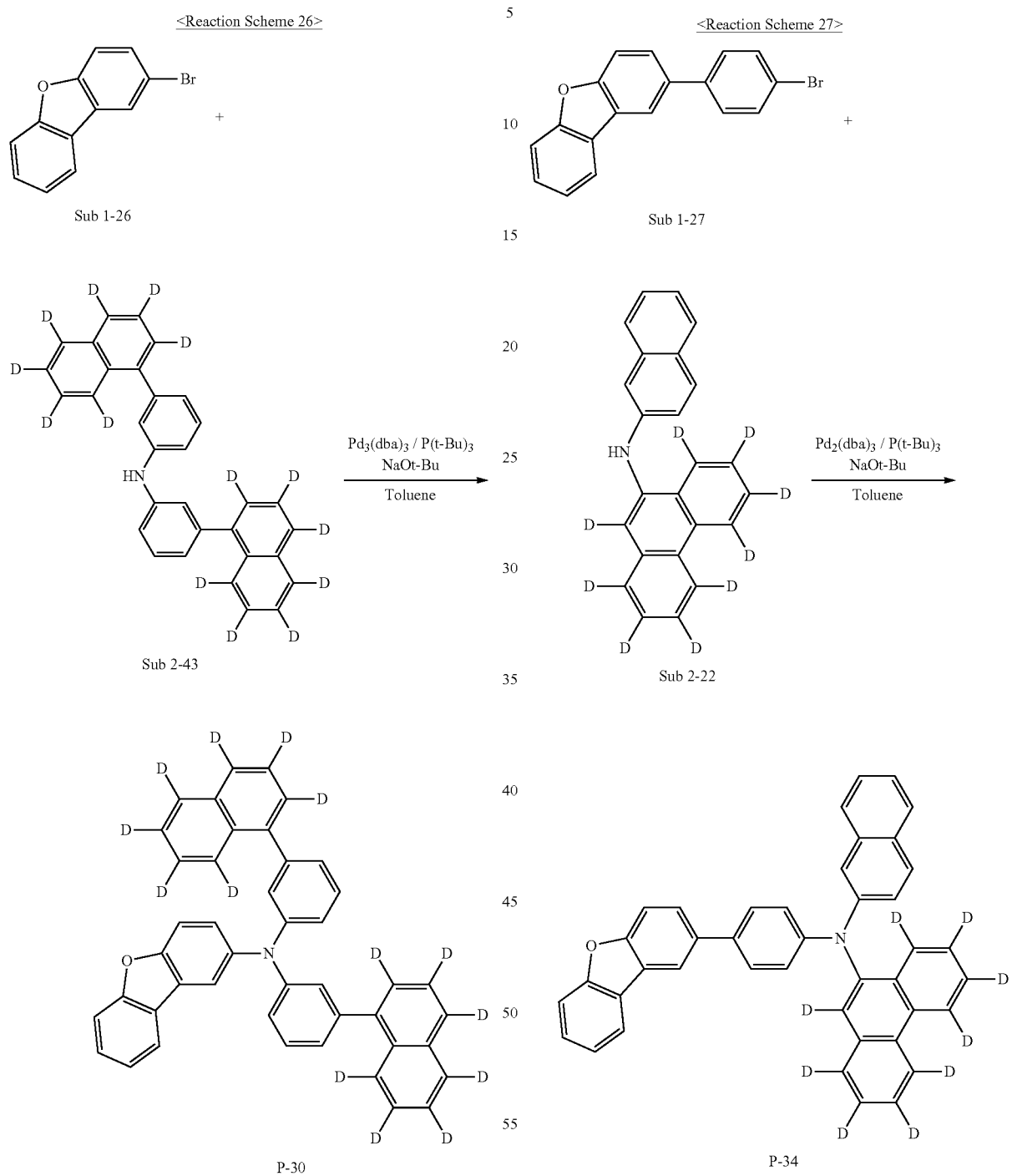

Sub 2-43 (7.40 g, 17.00 mmol), Pd$_2$(dba)$_3$ (0.47 g, 0.51 mmol), 50% P(t-Bu)$_3$ (0.7 ml, 1.36 mmol), NaOt-Bu (4.90 g, 50.99 mmol), toluene (170 ml) were added to Sub 1-26 (4.20 g, 17.00 mmol) obtained in the above synthesis, and then 7.67 g (yield: 75%) of the product was obtained by using the same manner as described above for the synthesis of the compound P-3.

Sub 2-22 (5.78 g, 17.61 mmol), Pd$_2$(dba)$_3$ (0.48 g, 0.53 mmol), 50% P(t-Bu)$_3$ (0.7 ml, 1.41 mmol), NaOt-Bu (5.08 g, 52.82 mmol), toluene (175 ml) were added to Sub 1-27 (5.69 g, 17.61 mmol) obtained in the above synthesis, and then 7.74 g (yield: 77%) of the product was obtained by using the same manner as described above for the synthesis of the compound P-3.

8. Synthesis Example of P-41

9. Synthesis Example of P-58

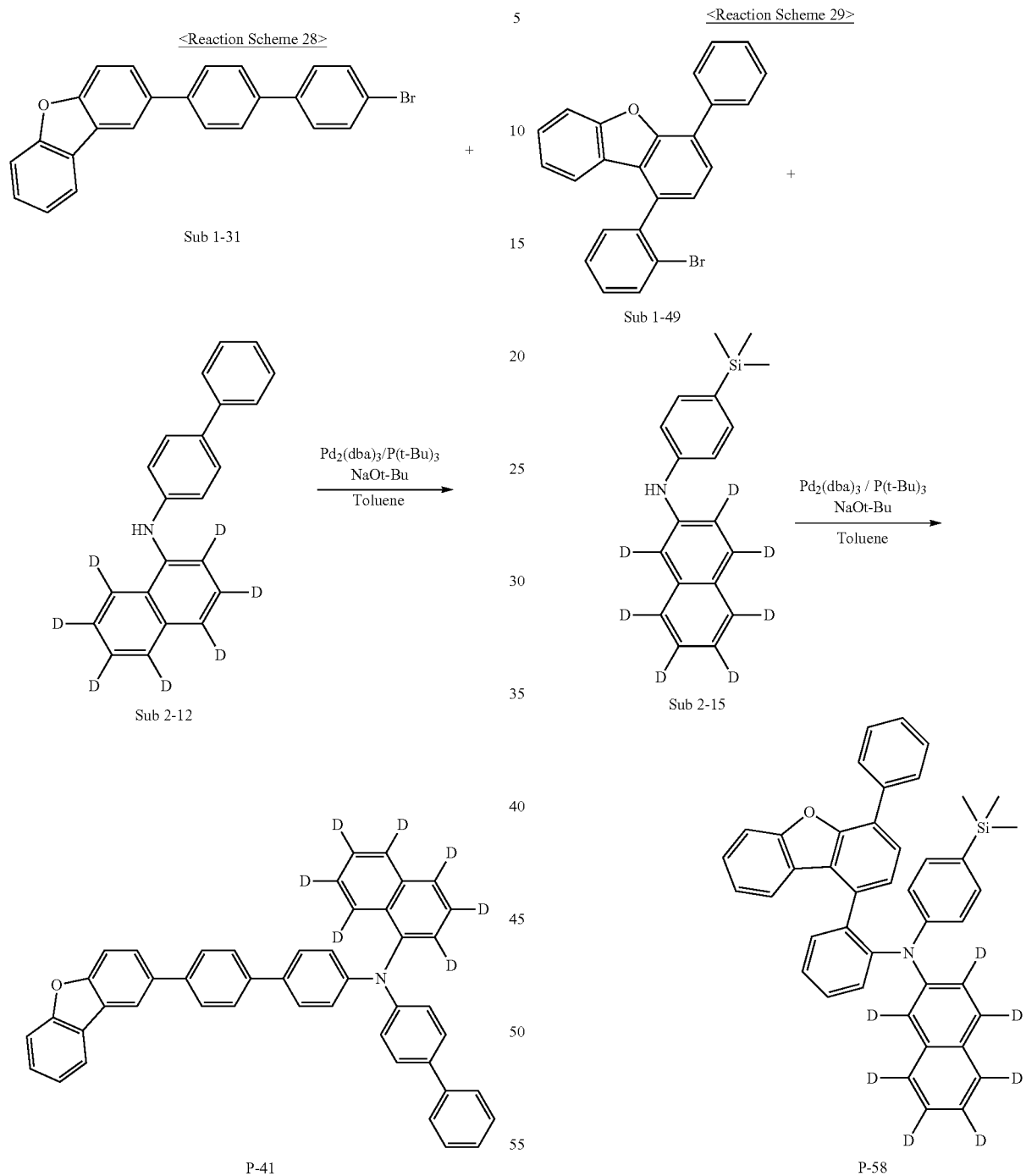

Sub 2-12 (4.79 g, 15.85 mmol), Pd2(dba)₃ (0.44 g, 0.48 mmol), 50% P(t-Bu)₃ (0.6 ml, 1.27 mmol), NaOt-Bu (4.57 g, 47.56 mmol), toluene (160 ml) were added to Sub 1-31 (6.33 g, 15.85 mmol) obtained in the above synthesis, and then 7.87 g (yield: 80%) of the product was obtained by using the same manner as described above for the synthesis of the compound P-3.

Sub 2-15 (5.66 g, 18.96 mmol), Pd₂(dba)₃ (0.52 g, 0.57 mmol), 50% P(t-Bu)₃ (0.7 ml, 1.52 mmol), NaOt-Bu (5.47 g, 56.88 mmol), toluene (190 ml) were added to Sub 1-49 (7.57 g, 18.96 mmol) obtained in the above synthesis, and then 7.60 g (yield: 65%) of the product was obtained by using the same manner as described above for the synthesis of the compound P-3.

The FD-MS values of compounds P-1 to P-60 of the present invention prepared according to the above synthesis examples are shown in Table 3 below.

TABLE 3

| compound | FD-MS | compound | FD-MS |
|---|---|---|---|
| P-1 | m/z = 568.26($C_{42}H_{24}D_5NO$ = 568.72) | P-2 | m/z = 597.29($C_{44}H_{19}D_{10}NO$ = 597.77) |
| P-3 | m/z = 544.25($C_{40}H_{20}D_7NO$ = 544.69) | P-4 | m/z = 620.28($C_{46}H_{24}D_7NO$ = 620.79) |
| P-5 | m/z = 657.37($C_{48}H_{15}D_{18}NO$ = 657.89) | P-6 | m/z = 630.35($C_{46}H_{14}D_{17}NO$ = 630.85) |
| P-7 | m/z = 740.30($C_{50}H_{24}D_{11}NO_3S$ = 740.95) | P-8 | m/z = 708.39($C_{52}H_{12}D_{21}NO$ = 708.95) |
| P-9 | m/z = 647.31($C_{48}H_{25}D_8NO$ = 647.83) | P-10 | m/z = 697.31($C_{51}H_{23}D_9N_2O$ = 697.87) |
| P-11 | m/z = 665.35($C_{49}H_{23}D_{12}NO$ = 665.88) | P-12 | m/z = 620.28($C_{46}H_{24}D_7NO$ = 620.79) |
| P-13 | m/z = 601.31($C_{44}H_{15}D_{14}NO$ = 601.79) | P-14 | m/z = 693.30($C_{52}H_{31}D_4NO$ = 693.87) |
| P-15 | m/z = 793.41($C_{59}H_{27}D_{14}NO$ = 794.05) | P-16 | m/z = 646.30($C_{48}H_{22}D_9NO$ = 646.82) |
| P-17 | m/z = 541.23($C_{40}H_{23}D_4NO$ = 541.67) | P-18 | m/z = 610.24($C_{44}H_{19}D_7FNO$ = 610.72) |
| P-19 | m/z = 644.28($C_{48}H_{24}D_7NO$ = 644.81) | P-20 | m/z = 629.34($C_{46}H_{15}D_{16}NO$ = 629.84) |
| P-21 | m/z = 666.27($C_{50}H_{26}D_5NO$ = 666.82) | P-22 | m/z = 754.34($C_{54}H_{34}D_7NOSi$ = 755.04) |
| P-23 | m/z = 620.27($C_{44}H_{28}D_3N_3O$ = 620.75) | P-24 | m/z = 505.31($C_{36}H_7D_{18}NO$ = 505.70) |
| P-25 | m/z = 620.28($C_{46}H_{24}D_7NO$ = 620.79) | P-26 | m/z = 734.33($C_{55}H_{34}D_5NO$ = 734.94) |
| P-27 | m/z = 631.27($C_{44}H_{13}D_{14}NOS$ = 631.84) | P-28 | m/z = 753.38($C_{56}H_{23}D_{14}NO$ = 753.99) |
| P-29 | m/z = 472.25($C_{34}H_{12}D_{11}NO$ = 472.62) | P-30 | m/z = 601.31($C_{44}H_{15}D_{14}NO$ = 601.79) |
| P-31 | m/z = 705.37$C_{52}H_{15}D_{18}NO$ = 705.94) | P-32 | m/z = 624.31($C_{46}H_{20}D_{11}NO$ = 624.81) |
| P-33 | m/z = 473.25($C_{34}H_{11}D_{12}NO$ = 473.63) | P-34 | m/z = 570.27($C_{42}H_{18}D_9NO$ = 570.73) |
| P-35 | m/z = 620.28($C_{46}H_{24}D_7NO$ = 620.79) | P-36 | m/z = 677.34($C_{50}H_{19}D_{14}NO$ = 677.89) |
| P-37 | m/z = 753.38($C_{56}H_{23}D_{14}NO$ = 753.99) | P-38 | m/z = 685.39($C_{50}H_{11}D_{22}NO$ = 685.94) |
| P-39 | m/z = 673.32($C_{50}H_{23}D_{10}NO$ = 673.86) | P-40 | m/z = 644.28($C_{48}H_{24}D_7NO$ = 644.81) |
| P-41 | m/z = 620.28($C_{46}H_{24}D_7NO$ = 620.79) | P-42 | m/z = 572.20($C_{40}H_{20}D_5NOS$ = 572.73) |
| P-43 | m/z = 677.34($C_{50}H_{19}D_{14}NO$ = 677.89) | P-44 | m/z = 723.33($C_{54}H_{25}D_{10}NO$ = 723.92) |
| P-45 | m/z = 696.32($C_{52}H_{28}D_7NO$ = 696.88) | P-46 | m/z = 793.41($C_{59}H_{27}D_{14}NO$ = 794.05) |
| P-47 | m/z = 785.35($C_{59}H_{27}D_{10}NO$ = 785.99) | P-48 | m/z = 573.28($C_{41}H_{27}D_5N_2O$ = 573.74) |
| P-49 | m/z = 577.31($C_{42}H_{15}D_{14}NO$ = 577.77) | P-50 | m/z = 677.34($C_{50}H_{19}D_{14}NO$ = 677.89) |
| P-51 | m/z = 629.34($C_{46}H_{15}D_{16}NO$ = 629.84) | P-52 | m/z = 596.28($C_{44}H_{20}D_9NO$ = 596.76) |
| P-53 | m/z = 578.32($C_{42}H_{14}D_{15}NO$ = 578.78) | P-54 | m/z = 632.25($C_{46}H_{24}D_5NO_2$ = 632.76) |
| P-55 | m/z = 570.27($C_{42}H_{26}D_5NO$ = 570.73) | P-56 | m/z = 648.31($C_{48}H_{24}D_9NO$ = 648.84) |
| P-57 | m/z = 755.39($C_{56}H_{21}D_{16}NO$ = 756.00) | P-58 | m/z = 616.29($C_{43}H_{28}D_7NOSi$ = 616.87) |
| P-59 | m/z = 713.35($C_{53}H_{23}D_{12}NO$ = 713.93) | P-60 | m/z = 705.37($C_{52}H_{19}D_{16}NO$ = 705.94) |

In the above, even though an exemplary synthesis example of the present invention represented by the Formula 1 are described, all of them are based on Buchwald-Hartwig cross coupling reaction, Pd(II)-catalyzed oxidative cyclization reaction (Org. Lett. 2011, 13, 5504), Miyaura boration reaction and Suzuki cross-coupling reaction. It will be understood by those skilled in the art that the above reaction proceeds even when other substituents (substituents of $R^1$, $R^2$, $L^1$ to $L^3$, $Ar^1$, $Ar^2$, m and n and the like) defined in Formula 1 are bonded, in addition to the substituents described in the specific synthesis example.

For example, the reaction of Sub 1 and Sub 2→Final Product in Reaction Scheme 1, and the reaction of the starting material→Sub 2 in Reaction Scheme 12 are based on Buchwald-Hartwig cross coupling reaction, the reaction of the starting material→Sub 1-I/Sub1 ($L^1$=single bond) in Reaction Scheme 2 is based on Pd(II)-catalyzed oxidative cyclization reaction, and the reaction of Sub 1-I→Sub 1-II in Reaction Scheme 2 is based on Miyaura boration reaction. Further, the reaction of Sub 1-II→Sub 1 in Reaction Scheme 2 is based on Suzuki cross-coupling reaction. The above reactions will proceed even if a substituent not specifically mentioned is attached.

Fabrication and Evaluation of Organic Electronic Element

Example I-1 Green OLED (A Hole Transport Layer)

Organic light emitting diodes (OLEDs) were fabricated according to a conventional method by using a compound of the present invention as a hole transport layer material.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm. Subsequently, compound P-1 of the present invention was vacuum-deposited with a thickness of 60 nm on the hole injection layer to form a hole transport layer. Subsequently, a light emitting layer with a thickness of 30 nm was formed on the hole transport layer by using 4,4'-N,N'-dicarbazole-biphenyl (hereinafter, "CBP") as a host material and tris(2-phenylpyridine)-iridium (hereinafter, "Ir(ppy)$_3$") as a dopant material in a weight ratio of 90:10.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq$_3$") was formed with a thickness of 40 nm to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

Example I-2 to Example I-43 Green OLED (A Hole Transport Layer)

The OLEDs were fabricated in the same manner as described in Example I-1 except that the compounds P-2 to P-60 of the present invention described in Table 4 instead of the compound P-1 of the present invention were used as the hole transport layer material.

Comparative Example I-1 to Comparative Example 1-5

The OLEDs were fabricated in the same manner as described in Example I-1 except that the following Comparative Compounds 1 to 5 instead of the compound P-1 of the present invention were each used as the hole transport layer material.

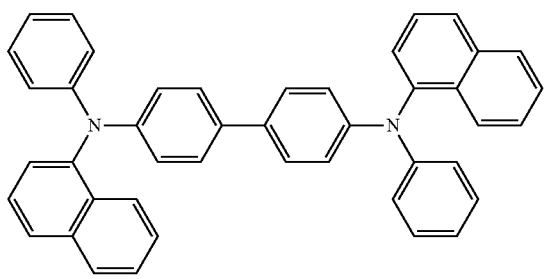

<Comp. compd 1>

<Comp. compd 2>

<Comp. compd 3>

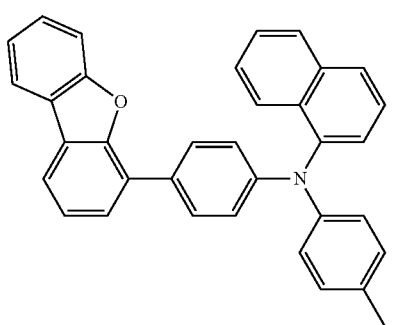

<Comp. compd 4>

<Comp. compd 5>

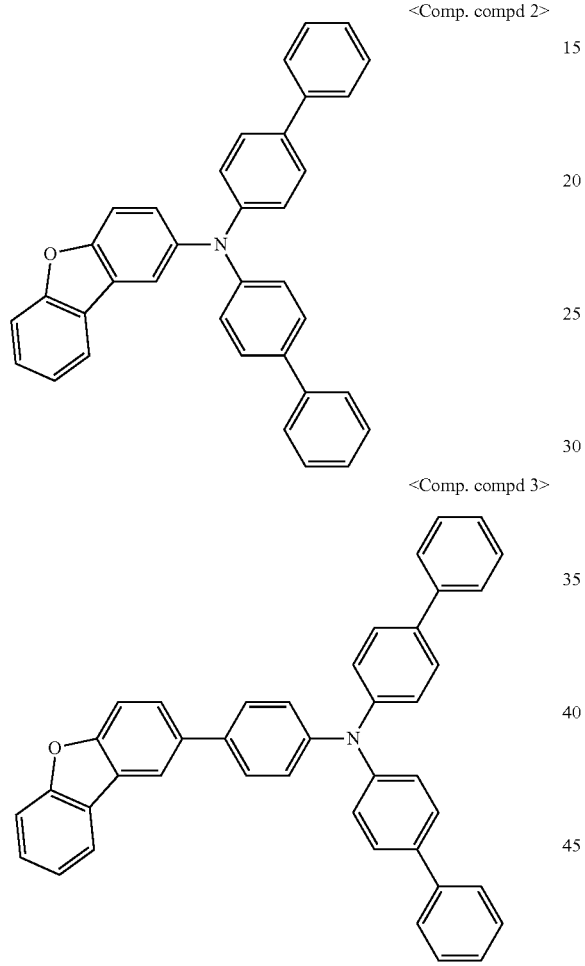

Electroluminescence (EL) characteristics were measured with a PR-650 (Photoresearch) by applying a forward bias DC voltage to the OLEDs prepared in Examples I-1 to I-43 of the present invention and Comparative Examples I-1 to I-5. And, the T95 life time was measured using a life time measuring apparatus manufactured by Macscience Inc. at reference brightness of 5000 cd/m$^2$. The measurement results are shown in Table 4 below.

TABLE 4

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(I-1) | comp. Com1 | 6.0 | 21.5 | 5000 | 23.3 | 57.2 | 0.32 | 0.61 |
| comp. Ex(I-2) | comp. Com2 | 5.9 | 18.4 | 5000 | 27.2 | 73.2 | 0.32 | 0.62 |
| comp. Ex(I-3) | comp. Com3 | 5.8 | 17.8 | 5000 | 28.1 | 76.8 | 0.33 | 0.62 |
| comp. Ex(I-4) | comp. Com4 | 5.8 | 17.5 | 5000 | 28.5 | 80.7 | 0.33 | 0.61 |
| comp. Ex(I-5) | comp. Com5 | 5.8 | 15.7 | 5000 | 31.9 | 82.3 | 0.33 | 0.62 |
| Ex.(I-1) | Com.(P-1) | 5.5 | 13.6 | 5000 | 36.7 | 129.3 | 0.33 | 0.62 |
| Ex.(I-2) | Com.(P-2) | 5.5 | 13.9 | 5000 | 36.1 | 134.1 | 0.33 | 0.62 |
| Ex.(I-3) | Com.(P-3) | 5.4 | 13.3 | 5000 | 37.7 | 140.3 | 0.33 | 0.61 |
| Ex.(I-4) | Com.(P-4) | 5.5 | 13.0 | 5000 | 38.5 | 140.7 | 0.33 | 0.62 |
| Ex.(I-5) | Com.(P-5) | 5.4 | 13.6 | 5000 | 36.9 | 128.0 | 0.33 | 0.61 |
| Ex.(I-6) | Com.(P-6) | 5.5 | 13.3 | 5000 | 37.7 | 136.4 | 0.33 | 0.61 |

TABLE 4-continued

| compound | Voltage (V) | Current Density (mA/cm²) | Brightness (cd/m²) | Efficiency (cd/A) | Lifetime T(95) | CIE x | CIE y |
|---|---|---|---|---|---|---|---|
| Ex.(I-7)  Com.(P-9)  | 5.5 | 13.6 | 5000 | 36.8 | 130.0 | 0.33 | 0.61 |
| Ex.(I-8)  Com.(P-11) | 5.4 | 13.2 | 5000 | 37.9 | 139.4 | 0.33 | 0.61 |
| Ex.(I-9)  Com.(P-13) | 5.5 | 13.2 | 5000 | 37.8 | 136.3 | 0.33 | 0.61 |
| Ex.(I-10) Com.(P-14) | 5.5 | 13.4 | 5000 | 37.2 | 133.4 | 0.33 | 0.62 |
| Ex.(I-11) Com.(P-15) | 5.5 | 13.1 | 5000 | 38.1 | 137.5 | 0.33 | 0.61 |
| Ex.(I-12) Com.(P-16) | 5.5 | 13.6 | 5000 | 36.8 | 135.4 | 0.33 | 0.61 |
| Ex.(I-13) Com.(P-17) | 5.5 | 14.5 | 5000 | 34.5 | 128.5 | 0.33 | 0.61 |
| Ex.(I-14) Com.(P-19) | 5.6 | 14.1 | 5000 | 35.4 | 132.7 | 0.33 | 0.61 |
| Ex.(I-15) Com.(P-20) | 5.5 | 13.4 | 5000 | 37.2 | 136.0 | 0.33 | 0.61 |
| Ex.(I-16) Com.(P-21) | 5.5 | 14.5 | 5000 | 34.5 | 132.3 | 0.33 | 0.61 |
| Ex.(I-17) Com.(P-24) | 5.6 | 14.0 | 5000 | 35.8 | 125.7 | 0.33 | 0.62 |
| Ex.(I-18) Com.(P-25) | 5.5 | 13.8 | 5000 | 36.1 | 132.6 | 0.33 | 0.62 |
| Ex.(I-19) Com.(P-27) | 5.5 | 14.1 | 5000 | 35.3 | 130.5 | 0.33 | 0.62 |
| Ex.(I-20) Com.(P-28) | 5.5 | 14.0 | 5000 | 35.8 | 130.7 | 0.33 | 0.62 |
| Ex.(I-21) Com.(P-29) | 5.4 | 13.2 | 5000 | 37.8 | 137.9 | 0.33 | 0.62 |
| Ex.(I-22) Com.(P-30) | 5.4 | 13.2 | 5000 | 37.9 | 140.5 | 0.33 | 0.61 |
| Ex.(I-23) Com.(P-31) | 5.4 | 13.0 | 5000 | 38.5 | 142.5 | 0.33 | 0.62 |
| Ex.(I-24) Com.(P-32) | 5.4 | 12.6 | 5000 | 39.7 | 147.2 | 0.33 | 0.62 |
| Ex.(I-25) Com.(P-33) | 5.5 | 13.0 | 5000 | 38.5 | 142.3 | 0.33 | 0.61 |
| Ex.(I-26) Com.(P-34) | 5.4 | 13.0 | 5000 | 38.6 | 141.0 | 0.33 | 0.61 |
| Ex.(I-27) Com.(P-35) | 5.4 | 12.5 | 5000 | 39.9 | 148.9 | 0.33 | 0.62 |
| Ex.(I-28) Com.(P-36) | 5.5 | 12.8 | 5000 | 39.1 | 144.0 | 0.33 | 0.62 |
| Ex.(I-29) Com.(P-37) | 5.5 | 13.0 | 5000 | 38.4 | 140.5 | 0.33 | 0.61 |
| Ex.(I-30) Com.(P-38) | 5.4 | 12.7 | 5000 | 39.3 | 144.2 | 0.33 | 0.62 |
| Ex.(I-31) Com.(P-39) | 5.4 | 13.1 | 5000 | 38.2 | 142.2 | 0.33 | 0.62 |
| Ex.(I-32) Com.(P-41) | 5.5 | 13.0 | 5000 | 38.4 | 141.4 | 0.33 | 0.62 |
| Ex.(I-33) Com.(P-42) | 5.4 | 12.9 | 5000 | 38.6 | 140.3 | 0.33 | 0.62 |
| Ex.(I-34) Com.(P-43) | 5.4 | 13.0 | 5000 | 38.5 | 141.1 | 0.33 | 0.61 |
| Ex.(I-35) Com.(P-45) | 5.4 | 13.0 | 5000 | 38.4 | 140.5 | 0.33 | 0.62 |
| Ex.(I-36) Com.(P-46) | 5.5 | 13.0 | 5000 | 38.4 | 142.3 | 0.33 | 0.62 |
| Ex.(I-37) Com.(P-49) | 5.6 | 14.8 | 5000 | 33.7 | 124.9 | 0.33 | 0.61 |
| Ex.(I-38) Com.(P-50) | 5.6 | 14.3 | 5000 | 34.9 | 129.7 | 0.33 | 0.62 |
| Ex.(I-39) Com.(P-51) | 5.6 | 14.0 | 5000 | 35.7 | 136.6 | 0.33 | 0.62 |
| Ex.(I-40) Com.(P-52) | 5.6 | 14.6 | 5000 | 34.2 | 126.4 | 0.33 | 0.62 |
| Ex.(I-41) Com.(P-53) | 5.5 | 14.7 | 5000 | 33.9 | 124.6 | 0.33 | 0.62 |
| Ex.(I-42) Com.(P-59) | 5.5 | 14.6 | 5000 | 34.2 | 127.0 | 0.33 | 0.61 |
| Ex.(I-43) Com.(P-60) | 5.6 | 14.5 | 5000 | 34.4 | 126.9 | 0.33 | 0.62 |

From the results of the above table 4, it can be confirmed that luminous efficiency and lifetime of OLED are improved when the compound of the present invention is used as material of a hole transport layer. Particularly, Comparative Example I-2 to Comparative Example I-5 using Comparative compounds 2 to 5 in which an arylamine group is bonded to dibenzofuran core via a linkage (comprising a single bond) exhibited higher luminous efficiency than Comparative Example I-1 using Comparative compound 1 that is NPB widely used. Further, Example I-1 to Example 1-43 using the compound of the present invention in which an arylamine group substituted with deuterium is bonded to dibenzofuran core via a linkage (comprising a single bond) exhibited lower driving voltage, higher luminous efficiency and improved lifetime, comparing to Comparative Example I-2 to Comparative Example I-5.

These results show that the results are different depending on whether or not an arylamine group is substituted with deuterium. When an arylamine group is substituted with deuterium, the molecular hardcore volume is reduced as the zero point energy, that is, the energy of the bottom state, is lowered and the bond length of carbon and deuterium becomes shorter than the bond length of carbon and hydrogen. As a result, the electrical polarizability can be reduced and intermolecular interaction can be weakened, thereby increasing the film volume.

This property can produce an effect of lowering the crystallinity of the thin film, that is, an amorphous state, and this amorphous state can reduce the grain boundary through isotropic and homogeneous characteristics. As a result, it is considered that the charge flow, that is, the hole mobility is increased, thereby making a very effective state in which the driving voltage of the organic electroluminescent device can be lowered and the lifetime can be improved.

Example II-1 Green OLED (An Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, Comparative compound 1 was vacuum-deposited with a thickness of 60 nm on the hole injection layer to form a hole transport layer. Subsequently, a film of the compound P-1 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 90:10.

Next, a film of BAlq was vacuum-deposited with a thickness of 10 nm on the light emitting layer to form a hole blocking layer, and a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Example II-2 to Example II-45 Green OLED (An Emission-Auxiliary Layer)

The OLEDs were fabricated in the same manner as described in Example II-1 except that the compounds P-3 to P-60 of the present invention described in Table 5, instead of the compound P-1 of the present invention, were used as an emission-auxiliary layer material.

Comparative Example II-1

The OLED was fabricated in the same manner as described in Example II-1 except that an emission-auxiliary layer was not formed.

Comparative Example II-2 to Comparative Example II-5 Green OLED (An Emission-Auxiliary Layer)

The OLEDs were fabricated in the same manner as described in Example II-1 except that the Comparative compounds 2 to 5, instead of the compound P-1 of the present invention, were used as an emission-auxiliary layer material.

Example II-46 Green OLED (An Emission-Auxiliary Layer)

The OLEDs were fabricated in the same manner as described in Example II-1 except that Comparative compound 6 described in Table 6, instead of Comparative compound 1, was used as a hole transport layer material.

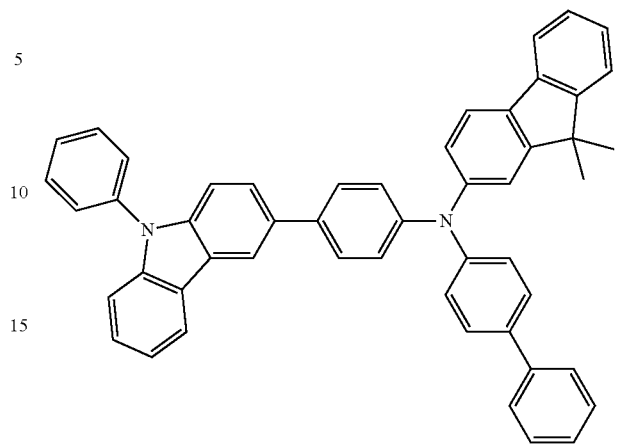

<Comp. compd 6>

Example II-47 to Example II-75 Green OLED (An Emission-Auxiliary Layer)

The OLEDs were fabricated in the same manner as described in Example II-46 except that the compounds P-3 to P-60 of the present invention described in Table 6, instead of the compound P-1 of the present invention, were used as an emission-auxiliary layer material.

Comparative Example II-6

The OLED was fabricated in the same manner as described in Example II-46 except that an emission-auxiliary layer was not formed.

Comparative Example II-7 to Comparative Example II-10 Green OLED (An Emission-Auxiliary Layer)

The OLEDs were fabricated in the same manner as described in Example II-46 except that the Comparative compounds 2 to 5 described in Table 6, instead of the compound P-1 of the present invention, were used as an emission-auxiliary layer material.

Electroluminescence (EL) characteristics were measured with a PR-650 (Photoresearch) by applying a forward bias DC voltage to the OLEDs prepared in Examples II-1 to II-75 of the present invention and Comparative Examples II-1 to II-10. And, the T95 life time was measured using a life time measuring apparatus manufactured by Macscience Inc. at reference brightness of 5000 cd/m$^2$. The measurement results are shown in Tables 5 and 6 below.

TABLE 5

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| comp. Ex(II-1) | comp. Com1 | — | 6.0 | 21.5 | 5000 | 23.3 | 57.2 |
| comp. Ex(II-2) | comp. Com1 | comp. Com2 | 6.4 | 14.3 | 5000 | 35.1 | 98.1 |
| comp. Ex(II-3) | comp. Com1 | comp. Com3 | 6.4 | 13.7 | 5000 | 36.6 | 101.4 |
| comp. Ex(II-4) | comp. Com1 | comp. Com4 | 6.4 | 13.6 | 5000 | 36.7 | 105.5 |
| comp. Ex(II-5) | comp. Com1 | comp. Com5 | 6.3 | 12.6 | 5000 | 39.8 | 116.5 |
| Ex.(II-1) | comp. Com1 | Com.(P-1) | 6.2 | 11.6 | 5000 | 43.2 | 147.0 |
| Ex.(II-2) | comp. Com1 | Com.(P-3) | 6.1 | 11.3 | 5000 | 44.3 | 150.2 |
| Ex.(II-3) | comp. Com1 | Com.(P-4) | 6.2 | 11.0 | 5000 | 45.3 | 156.6 |
| Ex.(II-4) | comp. Com1 | Com.(P-5) | 6.3 | 11.4 | 5000 | 43.8 | 142.1 |

TABLE 5-continued

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| Ex.(II-5) | comp. Com1 | Com.(P-6) | 6.2 | 11.3 | 5000 | 44.4 | 151.6 |
| Ex.(II-6) | comp. Com1 | Com.(P-9) | 6.2 | 11.3 | 5000 | 44.2 | 146.5 |
| Ex.(II-7) | comp. Com1 | Com.(P-11) | 6.1 | 11.2 | 5000 | 44.8 | 154.8 |
| Ex.(II-8) | comp. Com1 | Com.(P-13) | 6.2 | 11.3 | 5000 | 44.4 | 153.4 |
| Ex.(II-9) | comp. Com1 | Com.(P-14) | 6.3 | 11.4 | 5000 | 44.0 | 148.4 |
| Ex.(II-10) | comp. Com1 | Com.(P-15) | 6.2 | 11.2 | 5000 | 44.7 | 152.2 |
| Ex.(II-11) | comp. Com1 | Com.(P-16) | 6.3 | 11.3 | 5000 | 44.1 | 147.7 |
| Ex.(II-12) | comp. Com1 | Com.(P-17) | 6.3 | 11.7 | 5000 | 42.8 | 146.3 |
| Ex.(II-13) | comp. Com1 | Com.(P-18) | 6.3 | 11.6 | 5000 | 43.1 | 150.2 |
| Ex.(II-14) | comp. Com1 | Com.(P-19) | 6.3 | 11.3 | 5000 | 44.2 | 150.8 |
| Ex.(II-15) | comp. Com1 | Com.(P-20) | 6.2 | 11.0 | 5000 | 45.5 | 157.8 |
| Ex.(II-16) | comp. Com1 | Com.(P-25) | 6.1 | 11.3 | 5000 | 44.3 | 153.6 |
| Ex.(II-17) | comp. Com1 | Com.(P-27) | 6.3 | 11.4 | 5000 | 43.8 | 148.4 |
| Ex.(II-18) | comp. Com1 | Com.(P-28) | 6.2 | 11.4 | 5000 | 43.8 | 148.9 |
| Ex.(II-19) | comp. Com1 | Com.(P-29) | 6.2 | 11.3 | 5000 | 44.4 | 153.9 |
| Ex.(II-20) | comp. Com1 | Com.(P-30) | 6.2 | 11.2 | 5000 | 44.8 | 154.9 |
| Ex.(II-21) | comp. Com1 | Com.(P-31) | 6.1 | 11.1 | 5000 | 45.2 | 151.9 |
| Ex.(II-22) | comp. Com1 | Com.(P-32) | 6.1 | 10.7 | 5000 | 46.8 | 160.2 |
| Ex.(II-23) | comp. Com1 | Com.(P-33) | 6.2 | 11.1 | 5000 | 45.2 | 150.1 |
| Ex.(II-24) | comp. Com1 | Com.(P-34) | 6.2 | 10.9 | 5000 | 45.9 | 150.1 |
| Ex.(II-25) | comp. Com1 | Com.(P-35) | 6.1 | 10.6 | 5000 | 47.2 | 162.9 |
| Ex.(II-26) | comp. Com1 | Com.(P-36) | 6.1 | 10.9 | 5000 | 45.9 | 158.3 |
| Ex.(II-27) | comp. Com1 | Com.(P-37) | 6.1 | 11.0 | 5000 | 45.6 | 153.6 |
| Ex.(II-28) | comp. Com1 | Com.(P-38) | 6.1 | 10.8 | 5000 | 46.2 | 156.0 |
| Ex.(II-29) | comp. Com1 | Com.(P-39) | 6.1 | 11.0 | 5000 | 45.6 | 151.2 |
| Ex.(II 30) | comp. Com1 | Com.(P-40) | 6.2 | 11.2 | 5000 | 44.5 | 152.9 |
| Ex.(II-31) | comp. Com1 | Com.(P-41) | 6.2 | 11.1 | 5000 | 45.2 | 150.9 |
| Ex.(II-32) | comp. Com1 | Com.(P-42) | 6.1 | 11.0 | 5000 | 45.6 | 152.3 |
| Ex.(II-33) | comp. Com1 | Com.(P-43) | 6.2 | 10.9 | 5000 | 45.9 | 152.9 |
| Ex.(II-34) | comp. Com1 | Com.(P-44) | 6.1 | 11.1 | 5000 | 44.9 | 152.2 |
| Ex.(II-35) | comp. Com1 | Com.(P-45) | 6.2 | 10.9 | 5000 | 45.8 | 155.0 |
| Ex.(II-36) | comp. Com1 | Com.(P-46) | 6.1 | 11.0 | 5000 | 45.5 | 154.6 |
| Ex.(II-37) | comp. Com1 | Com.(P-47) | 6.2 | 11.2 | 5000 | 44.7 | 155.0 |
| Ex.(II-38) | comp. Com1 | Com.(P-50) | 6.3 | 11.6 | 5000 | 43.3 | 147.3 |
| Ex.(II-39) | comp. Com1 | Com.(P-51) | 6.3 | 11.4 | 5000 | 43.9 | 151.4 |
| Ex.(II-40) | comp. Com1 | Com.(P-52) | 6.3 | 11.8 | 5000 | 42.3 | 146.6 |
| Ex.(II-41) | comp. Com1 | Com.(P-54) | 6.3 | 11.8 | 5000 | 42.3 | 142.6 |
| Ex.(II-42) | comp. Com1 | Com.(P-57) | 6.3 | 11.9 | 5000 | 42.1 | 143.2 |
| Ex.(II-43) | comp. Com1 | Com.(P-58) | 6.3 | 11.9 | 5000 | 42.0 | 146.8 |
| Ex.(II-44) | comp. Com1 | Com.(P-59) | 6.3 | 11.8 | 5000 | 42.6 | 146.6 |
| Ex.(II-45) | comp. Com1 | Com.(P-60) | 6.3 | 11.7 | 5000 | 42.6 | 146.0 |

TABLE 6

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| comp. Ex(II-6) | comp. Com6 | — | 5.0 | 14.3 | 5000 | 35.0 | 97.3 |
| comp. Ex(II-7) | comp. Com6 | comp. Com2 | 5.4 | 13.4 | 5000 | 37.2 | 115.7 |
| comp. Ex(II-8) | comp. Com6 | comp. Com3 | 5.3 | 13.0 | 5000 | 38.4 | 120.1 |
| comp. Ex(II-9) | comp. Com6 | comp. Com4 | 5.3 | 12.9 | 5000 | 38.9 | 124.6 |
| comp. Ex(II-10) | comp. Com6 | comp. Com5 | 5.3 | 12.0 | 5000 | 41.7 | 131.4 |
| Ex.(II-46) | comp. Com6 | Com.(P-1) | 5.3 | 10.8 | 5000 | 46.1 | 158.0 |
| Ex.(II-47) | comp. Com6 | Com.(P-3) | 5.1 | 10.4 | 5000 | 48.0 | 167.9 |
| Ex.(II-48) | comp. Com6 | Com.(P-4) | 5.1 | 10.4 | 5000 | 48.0 | 171.0 |
| Ex.(II-49) | comp. Com6 | Com.(P-6) | 5.1 | 10.5 | 5000 | 47.5 | 167.3 |
| Ex.(II-50) | comp. Com6 | Com.(P-11) | 5.2 | 10.4 | 5000 | 48.0 | 167.0 |
| Ex.(II-51) | comp. Com6 | Com.(P-13) | 5.2 | 10.5 | 5000 | 47.5 | 165.9 |
| Ex.(II-52) | comp. Com6 | Com.(P-15) | 5.2 | 10.5 | 5000 | 47.6 | 166.2 |
| Ex.(II-53) | comp. Com6 | Com.(P-19) | 5.2 | 10.7 | 5000 | 46.9 | 160.9 |
| Ex.(II-54) | comp. Com6 | Com.(P-20) | 5.2 | 10.4 | 5000 | 48.1 | 169.2 |
| Ex.(II-55) | comp. Com6 | Com.(P-25) | 5.2 | 10.4 | 5000 | 48.0 | 167.6 |
| Ex.(II-56) | comp. Com6 | Com.(P-27) | 5.2 | 10.6 | 5000 | 47.4 | 161.0 |
| Ex.(II-57) | comp. Com6 | Com.(P-28) | 5.3 | 10.6 | 5000 | 47.2 | 164.3 |
| Ex.(II-58) | comp. Com6 | Com.(P-30) | 5.2 | 10.5 | 5000 | 47.5 | 166.4 |
| Ex.(II-59) | comp. Com6 | Com.(P-31) | 5.2 | 10.3 | 5000 | 48.7 | 164.8 |
| Ex.(II-60) | comp. Com6 | Com.(P-32) | 5.1 | 10.0 | 5000 | 50.2 | 175.4 |
| Ex.(II-61) | comp. Com6 | Com.(P-33) | 5.1 | 10.3 | 5000 | 48.4 | 164.8 |
| Ex.(II-62) | comp. Com6 | Com.(P-34) | 5.1 | 10.3 | 5000 | 48.4 | 168.2 |
| Ex.(II-63) | comp. Com6 | Com.(P-35) | 5.1 | 9.9 | 5000 | 50.5 | 176.5 |
| Ex.(II-64) | comp. Com6 | Com.(P-36) | 5.1 | 10.2 | 5000 | 49.0 | 170.5 |
| Ex.(II-65) | comp. Com6 | Com.(P-37) | 5.2 | 10.4 | 5000 | 48.3 | 167.2 |

TABLE 6-continued

|  | HTL com. | EAL com. | Voltage (V) | Current Density (mA/cm²) | Brightness (cd/m²) | Efficiency (cd/A) | Lifetime T(95) |
|---|---|---|---|---|---|---|---|
| Ex.(II-66) | comp. Com6 | Com.(P-38) | 5.1 | 10.2 | 5000 | 48.8 | 170.1 |
| Ex.(II-67) | comp. Com6 | Com.(P-39) | 5.1 | 10.3 | 5000 | 48.7 | 168.2 |
| Ex.(II-68) | comp. Com6 | Com.(P-41) | 5.2 | 10.3 | 5000 | 48.4 | 168.2 |
| Ex.(II-69) | comp. Com6 | Com.(P-42) | 5.2 | 10.3 | 5000 | 48.7 | 168.1 |
| Ex.(II-70) | comp. Com6 | Com.(P-43) | 5.2 | 10.3 | 5000 | 48.8 | 167.6 |
| Ex.(II-71) | comp. Com6 | Com.(P-45) | 5.1 | 10.3 | 5000 | 48.4 | 164.3 |
| Ex.(II-72) | comp. Com6 | Com.(P-46) | 5.2 | 10.3 | 5000 | 48.5 | 167.6 |
| Ex.(II-73) | comp. Com6 | Com.(P-50) | 5.3 | 10.8 | 5000 | 46.4 | 164.6 |
| Ex.(II-74) | comp. Com6 | Com.(P-51) | 5.3 | 10.7 | 5000 | 46.6 | 166.5 |
| Ex.(II-75) | comp. Com6 | Com.(P-60) | 5.3 | 10.9 | 5000 | 45.7 | 156.5 |

Example III-1 Blue Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, the Comparative compound 6 was vacuum-deposited with a thickness of 60 nm on the hole injection layer to form a hole transport layer. Next, the inventive compound P-4 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with 9,10-di(naphthalen-2-yl)anthracene (hereinafter abbreviated as "ADN") as a host material and BD-052X (made by Idemitsu kosan) as a dopant material in a weight ratio of 96:4. Subsequently, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

Example III-2 to Example III-12 Blue OLED (An Emission-Auxiliary Layer)

The OLEDs were fabricated in the same manner as described in Example III-1 except that the compounds P-6 to P-51 of the present invention described in Table 7, instead of the compound P-4 of the present invention, were used as an emission-auxiliary layer material.

Comparative Example III-1

The OLED was fabricated in the same manner as described in Example III-1 except that an emission-auxiliary layer was not formed.

Comparative Example IIII-2 to Comparative Example III-4 Blue OLED (An Emission-Auxiliary Layer)

The OLEDs were fabricated in the same manner as described in Example III-1 except that the Comparative compounds 3 to 5 described in Table 7, instead of the compound P-4 of the present invention, were used as an emission-auxiliary layer material.

Electroluminescence (EL) characteristics were measured with a PR-650 (Photoresearch) by applying a forward bias DC voltage to the OLEDs prepared in Examples III-1 to III-12 of the present invention and Comparative Examples III-1 to III-4. And, the T95 life time was measured using a life time measuring apparatus manufactured by Macscience Inc. at reference brightness of 500 cd/m². The measurement results are shown in Table 7 below.

TABLE 7

|  | HTL com. | EAL com. | Voltage (V) | Current Density (mA/cm2) | Brightness (cd/m2) | Efficiency (cd/A) | Lifetime T(95) |
|---|---|---|---|---|---|---|---|
| comp. Ex(III-1) | comp. Com6 | — | 4.2 | 12.2 | 500 | 4.1 | 95.8 |
| comp. Ex(III-2) | comp. Com6 | comp. Com3 | 4.4 | 7.6 | 500 | 6.6 | 109.1 |
| comp. Ex(III-3) | comp. Com6 | comp. Com4 | 4.4 | 7.5 | 500 | 6.6 | 116.0 |
| comp. Ex(III-4) | comp. Com6 | comp. Com5 | 4.3 | 7.2 | 500 | 6.9 | 120.7 |
| Ex.(III-1) | comp. Com6 | Com.(P-4) | 4.4 | 6.8 | 500 | 7.4 | 164.2 |
| Ex.(III-2) | comp. Com6 | Com.(P-6) | 4.4 | 6.7 | 500 | 7.5 | 161.9 |
| Ex.(III-3) | comp. Com6 | Com.(P-11) | 4.4 | 6.7 | 500 | 7.4 | 162.1 |
| Ex.(III-4) | comp. Com6 | Com.(P-20) | 4.4 | 6.7 | 500 | 7.4 | 164.3 |
| Ex.(III-5) | comp. Com6 | Com.(P-25) | 4.3 | 6.7 | 500 | 7.4 | 159.6 |
| Ex.(III-6) | comp. Com6 | Com.(P-32) | 4.3 | 6.6 | 500 | 7.6 | 170.2 |
| Ex.(III-7) | comp. Com6 | Com.(P-33) | 4.4 | 6.7 | 500 | 7.5 | 164.7 |
| Ex.(III-8) | comp. Com6 | Com.(P-35) | 4.3 | 6.6 | 500 | 7.6 | 172.9 |
| Ex.(III-9) | comp. Com6 | Com.(P-36) | 4.3 | 6.7 | 500 | 7.5 | 168.6 |
| Ex.(III-10) | comp. Com6 | Com.(P-38) | 4.3 | 6.6 | 500 | 7.5 | 167.7 |
| Ex.(III-11) | comp. Com6 | Com.(P-41) | 4.3 | 6.7 | 500 | 7.4 | 164.8 |
| Ex.(III-12) | comp. Com6 | Com.(P-51) | 4.4 | 6.8 | 500 | 7.3 | 156.6 |

From the results shown in Tables 5 to 7, it can be seen that the luminous efficiency and lifetime of the organic electroluminescent device are remarkably improved when compounds of the present invention were used as an emission-auxiliary layer material, compared with the organic electroluminescent device of Comparative Example II-1 to Comparative Example III-4.

From these results, it is confirmed that luminescent efficiency and lifetime of device are improved when Comparative Compounds 2 to 5 and the compound of the present invention are used as an emission-auxiliary layer material, among them, particularly the compound of the present invention, compared with device not having an emission-auxiliary layer.

It can be confirmed that the structure in which an arylamine group substituted with deuterium is bonded to dibenzofuran core via a linkage (comprising a single bond) acts as a major factor in improving the performance of the device in the light-emitting auxiliary layer (green phosphorescence, blue fluorescence) as well as in the hole transport layer. Also, it is confirmed that the compound of the present invention used as the light emitting auxiliary layer material has a deep HOMO energy level and a high T1 value, thereby maintaining the charge balance in the light emitting layer and performing an effective electronic blocking function, as a result, the light emitting efficiency and lifetime are improved.

Further, it can be confirmed that the planarity of the molecules is further increased when 1 to 2 substituents having planarity are introduced into the amine group of the compound of the present invention, and the packing density is increased, thereby reducing the Joule heat generated when the device is driven, as a result, the lifetime is remarkably increased due to the high thermal stability. It is considered that this is because the substituent having planarity is not introduced excessively and within an appropriate range, so that the rise of the driving voltage due to the trap phenomenon hardly occurs and the improvement of the heat resistance is more effective.

Accordingly, the compound of the present invention can provide an effective electron blocking ability and a hole transporting ability, and the compound of the present invention can lower the driving voltage of the device, increase the luminous efficiency, have high heat resistance, and improve the color purity and lifetime.

In addition, in the evaluation results of the device fabrication described above, even though the characteristics of devise have been described when the compound of the present invention is used as material of only one layer of the hole transport layer and an emission-auxiliary layer, the compound of the present invention can be used as material of both the hole transport layer and an emission-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

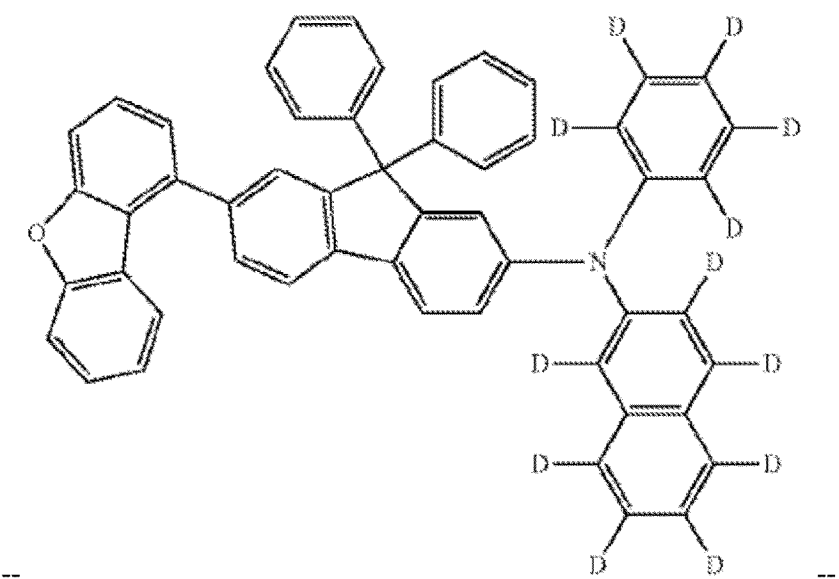

The invention claimed is:
1. A compound of Formula 2 or 3:

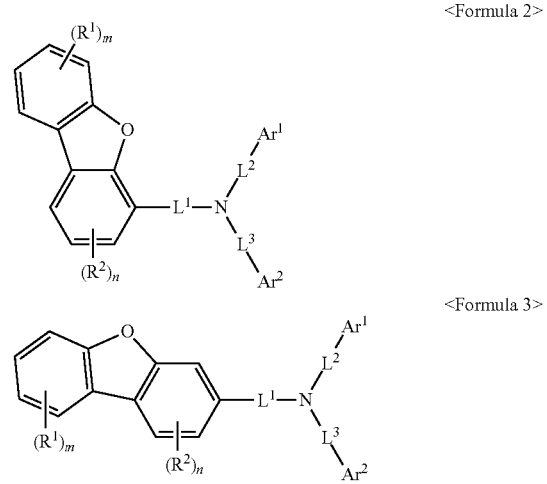

wherein:
$R^1$ and $R^2$ are each independently selected from the group consisting of deuterium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, wherein the aryl, fluorenyl, heterocyclic, fused ring, alkyl, alkenyl, alkynyl, alkoxy or aryloxy group may be each optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, m is an integer of 0 to 4, and when m is an integer of 2 or more, $R^1$s may be the same or different from each other, n is an integer of 0 to 3, and when n is an integer of 2 or more, $R^2$s may be the same or different from each other, $Ar^1$ and $Ar^2$ are each independently a $C_6$-$C_{60}$ aryl group, with the proviso that at least one of $Ar^1$ and $Ar^2$ is a pyrenyl, phenanthrenyl, or fluoranthenyl group, $L^1$ is selected from the group consisting of a single bond; a $C_6$-$C_{60}$ arylene group; a divalent $C_2$-$C_{60}$ heterocyclic group containing at least one heteroatom selected from the group consisting of O, N, S, Si, and P; a fluorenylene group; and a divalent fused ring formed by a $C_3$-$C_{60}$ aliphatic ring and a $C_6$-$C_{60}$ aromatic ring wherein the arylene, heterocyclic, fluorenylene, or fused ring may be optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and $L^2$ and $L^3$ are each independently selected from the group consisting of a single bond; and a $C_6$-$C_{60}$ arylene group, with the proviso that:

i. both $L^2$ and $L^3$ are not a single bond at the same time,
ii. where $L^2$ or $L^3$ is a $C_6$-$C_{60}$ arylene group, the arylene group is substituted with one or more substituents selected from the group consisting of deuterium, halogen, a silane group substituted or unsubstituted with a $C_1$-$C_{20}$ alkyl group or a $C_6$-$C_{20}$ aryl group, a $C_1$-$C_{20}$ alkyl group, and a $C_2$-$C_{20}$ alkenyl group,
iii. $Ar^1$ and $Ar^2$ may be each optionally substituted with one or more substituents selected from the group consisting of deuterium, halogen, a silane group substituted or unsubstituted with a $C_1$-$C_{20}$ alkyl group or a $C_6$-$C_{20}$ aryl group, a $C_1$-$C_{20}$ alkyl group and a $C_2$-$C_{20}$ alkenyl group, and
iv. at least one of $L^1$, $L^2$, $Ar^1$ and $Ar^2$ is substituted with at least one deuterium.

2. An organic electric element comprising a first electrode, a second electrode, and an organic material layer formed between the first electrode and the second electrode, wherein the organic material layer comprises the compound of claim 1.

3. The organic electric element of claim 2, wherein the organic material layer comprises at least one layer of a hole injection layer, a hole transport layer, an emission-auxiliary layer and an light emitting layer.

4. The organic electric element of claim 2, wherein the organic material layer is formed by any one of the processes of spin coating, nozzle printing, inkjet printing, slot coating, dip coating or roll-to-roll.

5. An electronic device comprising a display device and a control unit for driving the display device, wherein the display device comprises the organic electric element of claim 2.

6. The electronic device of claim 5, wherein the organic electric element is an organic light emitting diode, an organic solar cell, an organic photo conductor, an organic transistor, or an element for monochromatic or white illumination.

7. A compound selected from the group consisting of the compounds below:

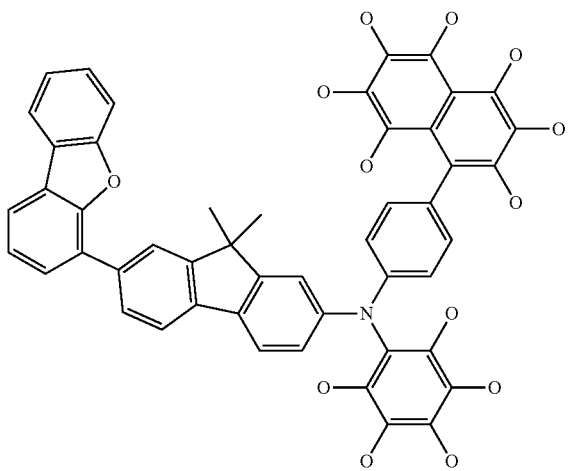

P-11

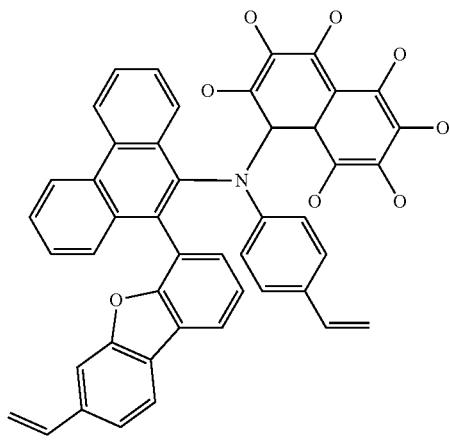

P-12

P-15
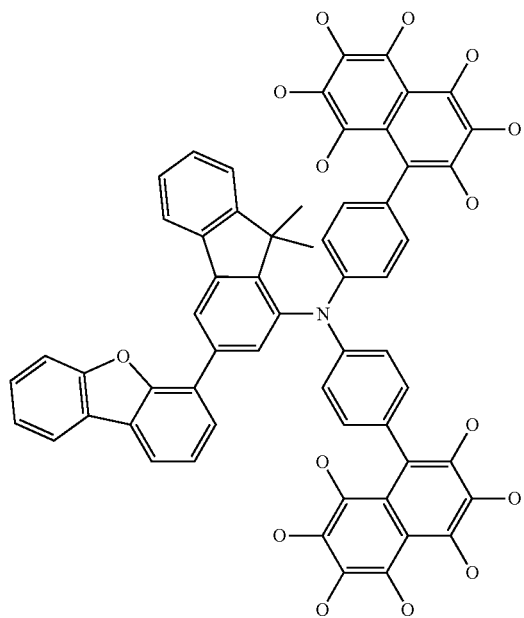
P-16
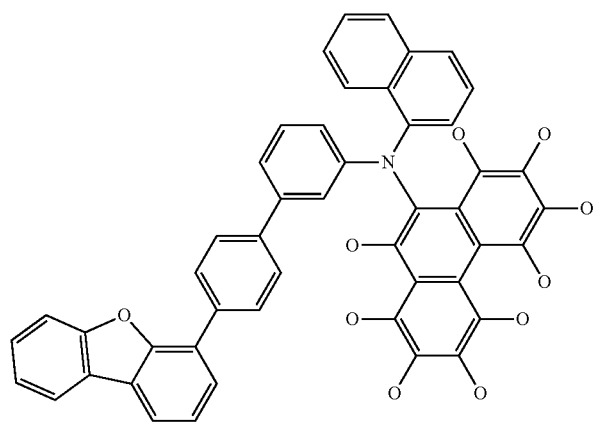
P-18
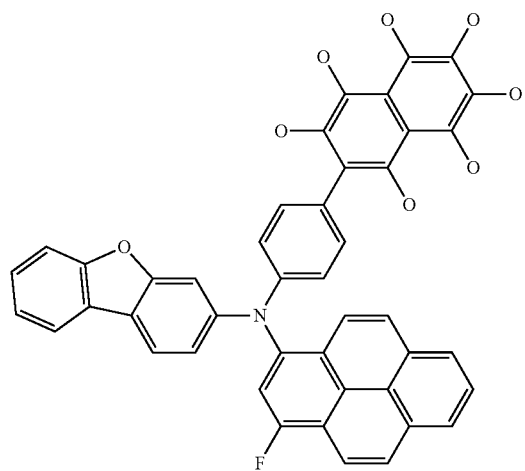

P-19
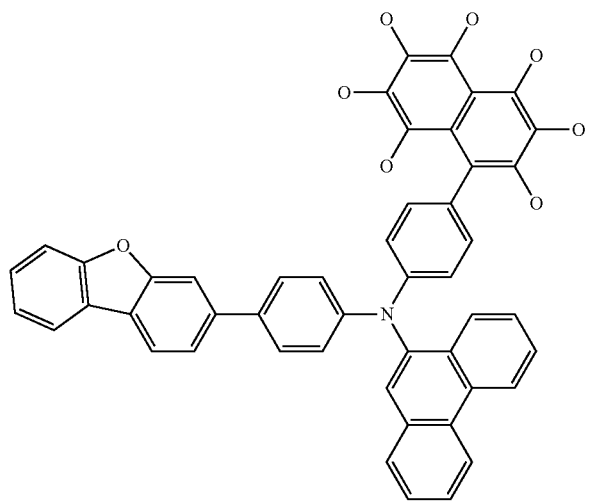
P-21
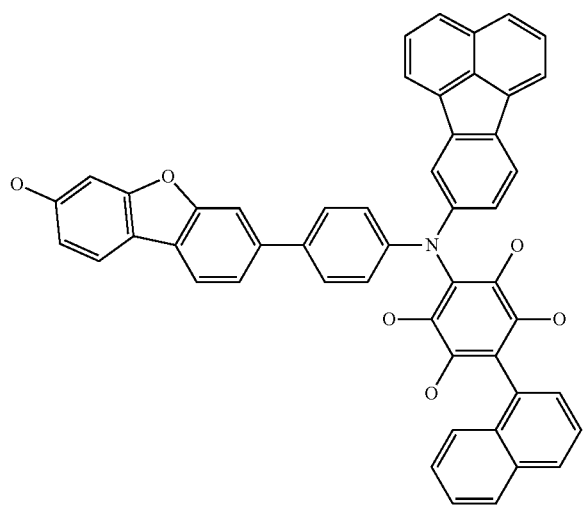
P-22
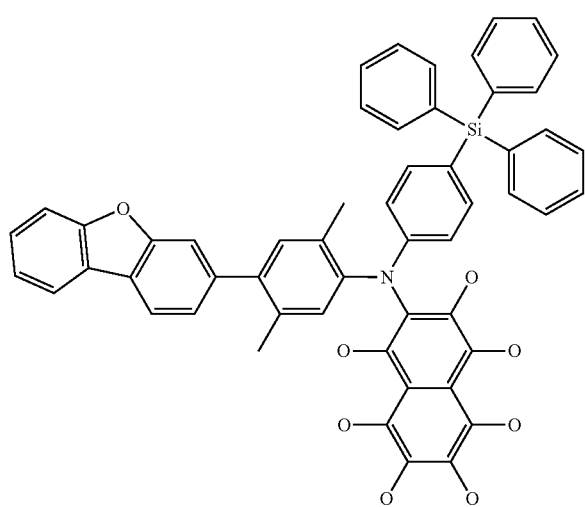

-continued
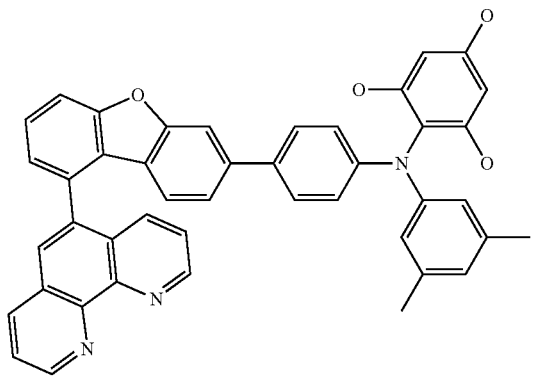
P-23
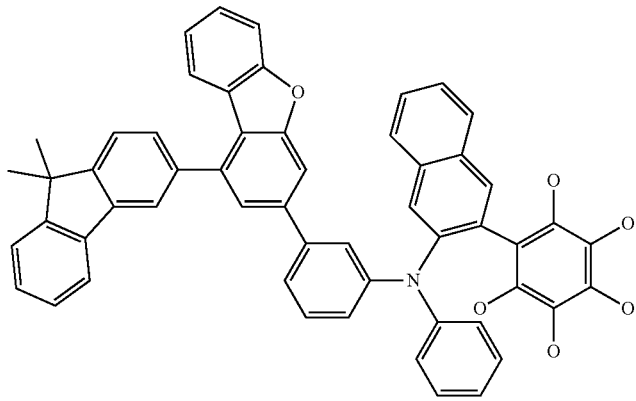
P-26
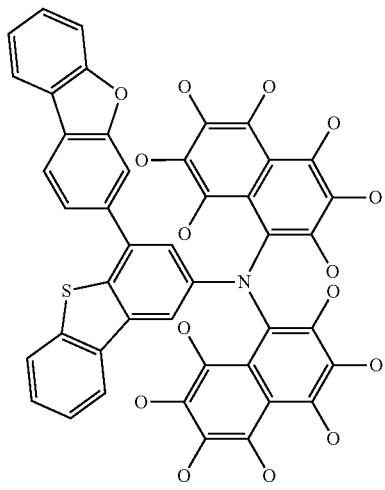
P-27
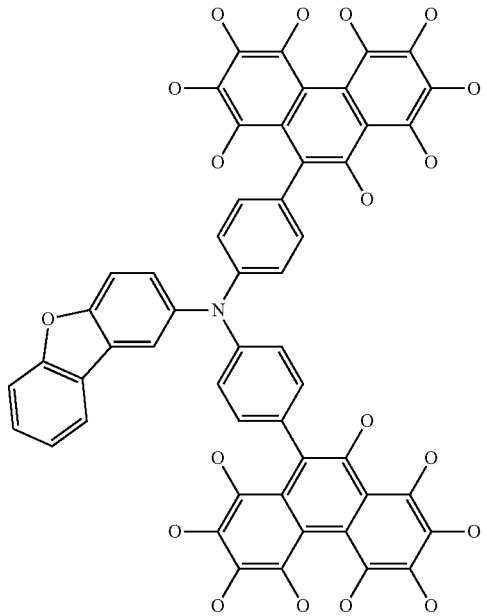
P-31

P-34
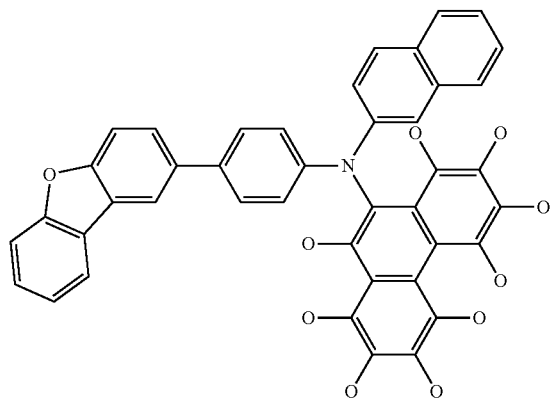
P-37
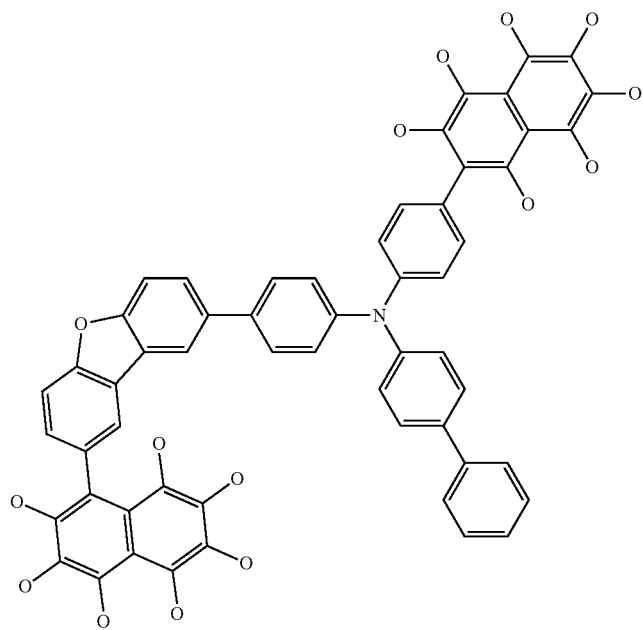
P-46
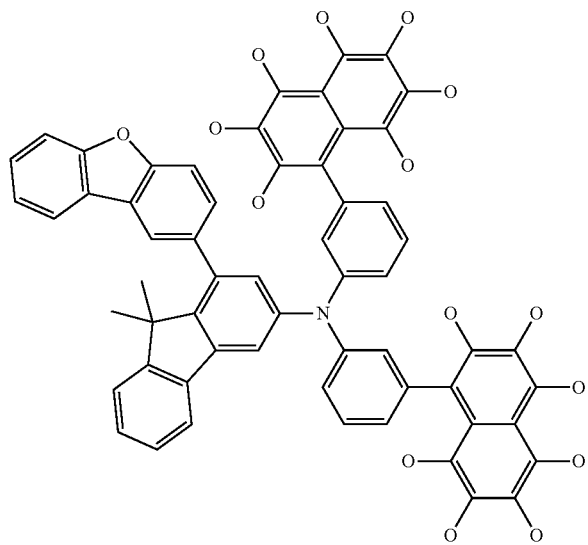

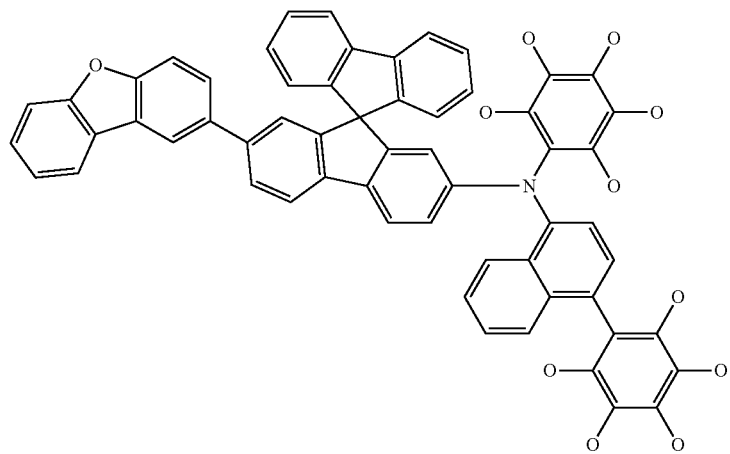
P-47
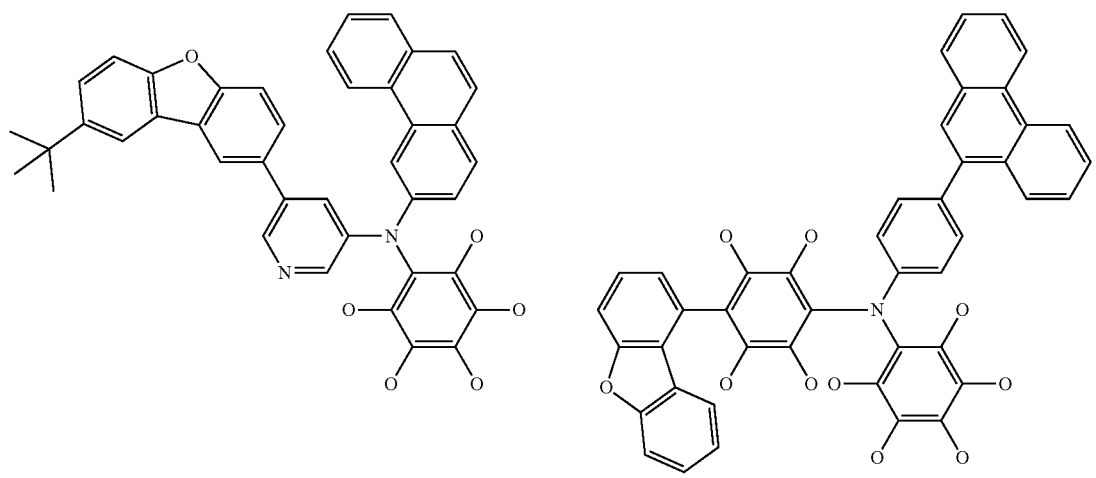
P-48
P-52
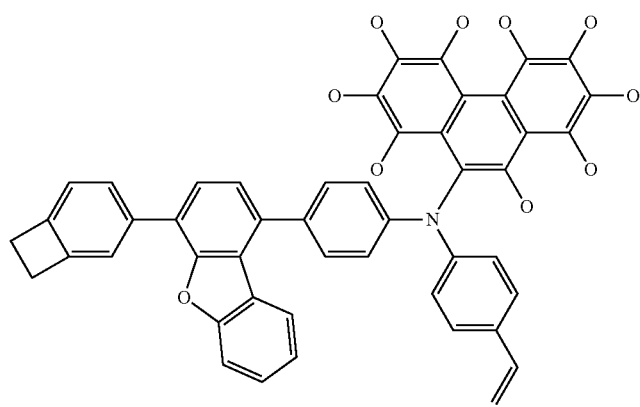
P-56

P-58

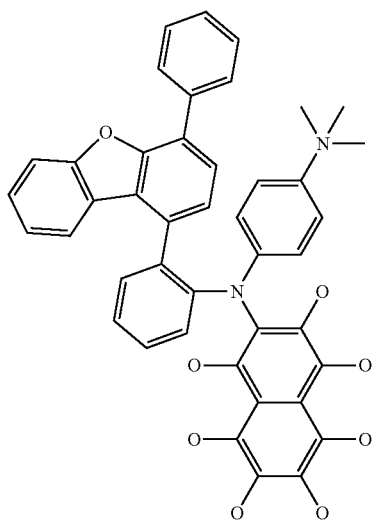

P-59

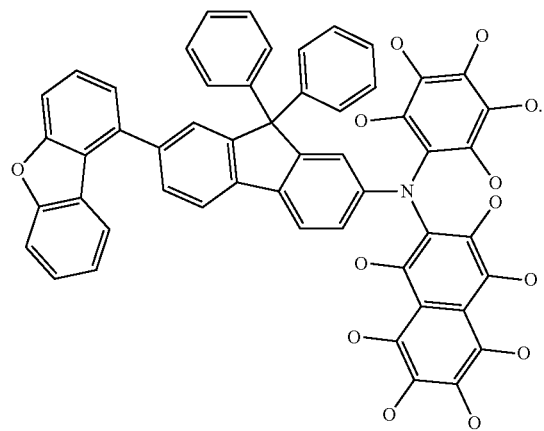

8. An organic electric element comprising a first electrode, a second electrode, and an organic material layer formed between the first electrode and the second electrode, wherein the organic material layer comprises the compound of claim 7.

9. An electronic device comprising a display device and a control unit for driving the display device, wherein the display device comprises the organic electric element of claim 8.

* * * * *

UNITED STATES PATENT AND TRADEMARK OFFICE
CERTIFICATE OF CORRECTION

PATENT NO. : 11,196,008 B2
APPLICATION NO. : 15/739611
DATED : December 7, 2021
INVENTOR(S) : Park et al.

Page 1 of 22

It is certified that error appears in the above-identified patent and that said Letters Patent is hereby corrected as shown below:

In the Claims

Column 102, Claim 7, Formula P-11:
Please delete:

"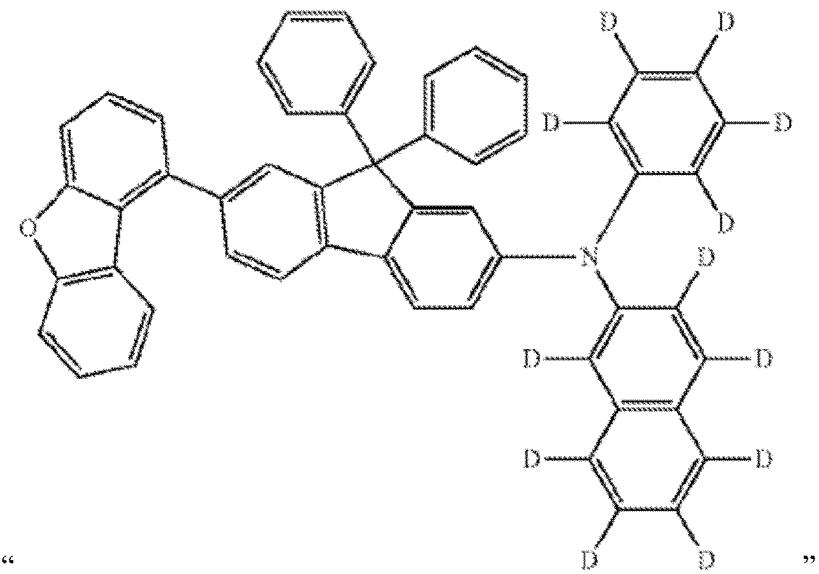"

Signed and Sealed this
Twenty-first Day of June, 2022

Katherine Kelly Vidal
*Director of the United States Patent and Trademark Office*

CERTIFICATE OF CORRECTION (continued)
U.S. Pat. No. 11,196,008 B2

Page 2 of 22

And replace with:

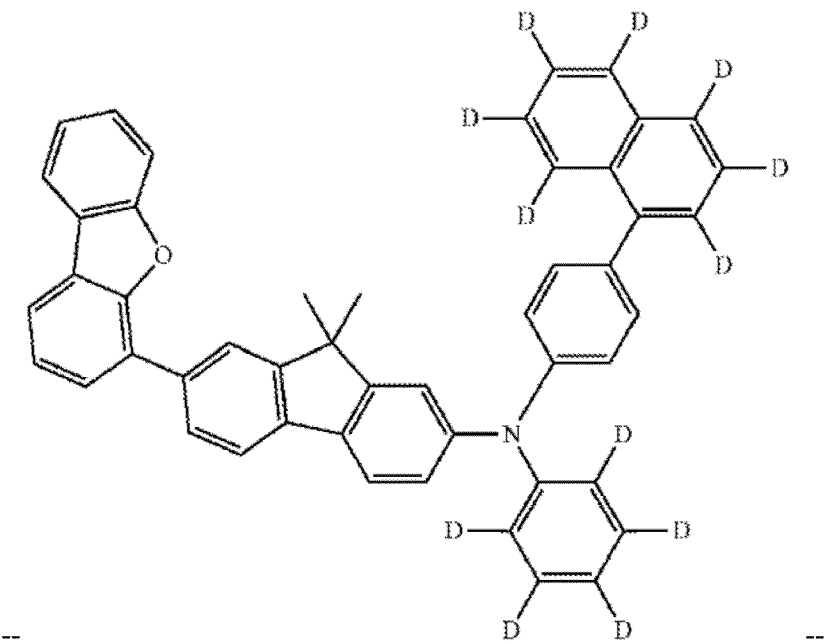

Column 102, Claim 7, Formula P-12:
Please delete:

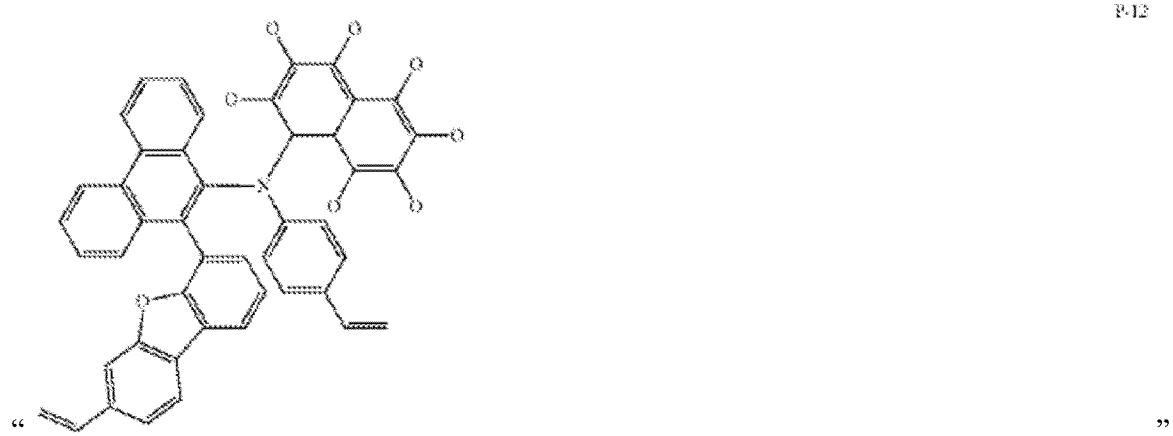

CERTIFICATE OF CORRECTION (continued)
U.S. Pat. No. 11,196,008 B2

And replace with:

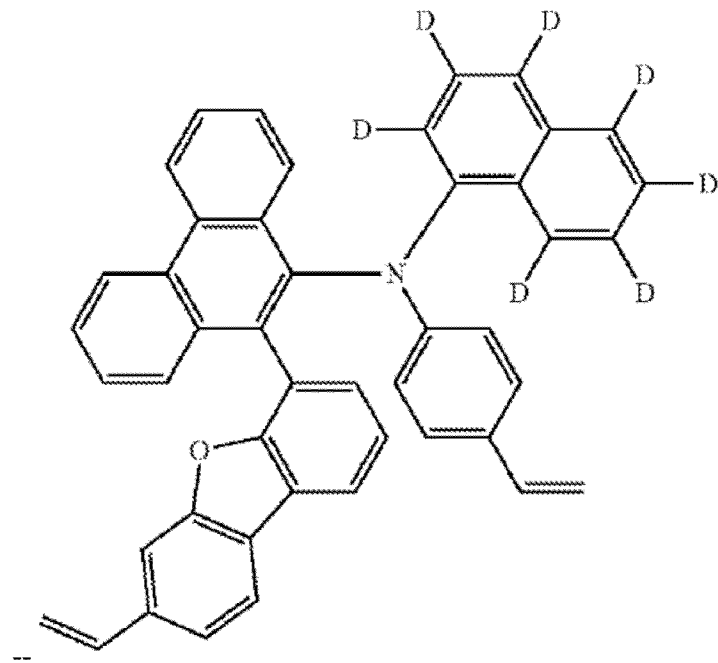

Column 103, Claim 7, Formula P-15:
Please delete:

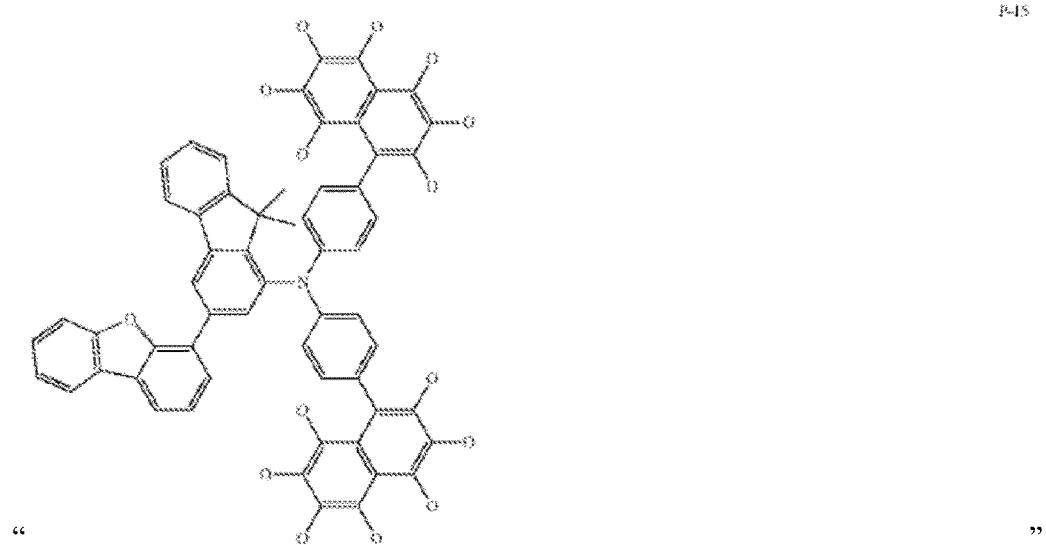

CERTIFICATE OF CORRECTION (continued)
U.S. Pat. No. 11,196,008 B2

Page 4 of 22

And replace with:

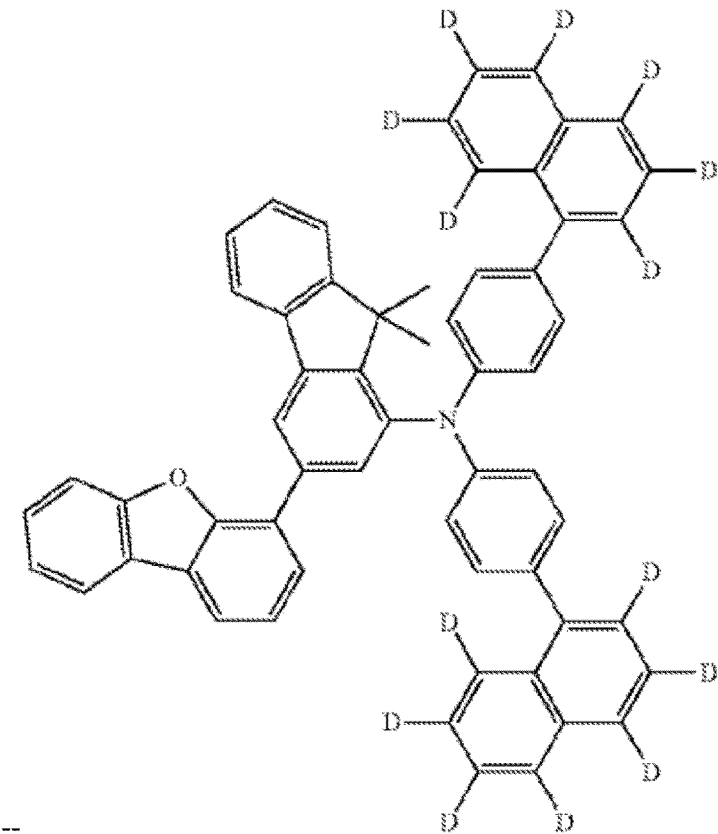

Column 103, Claim 7, Formula P-16:
Please delete:

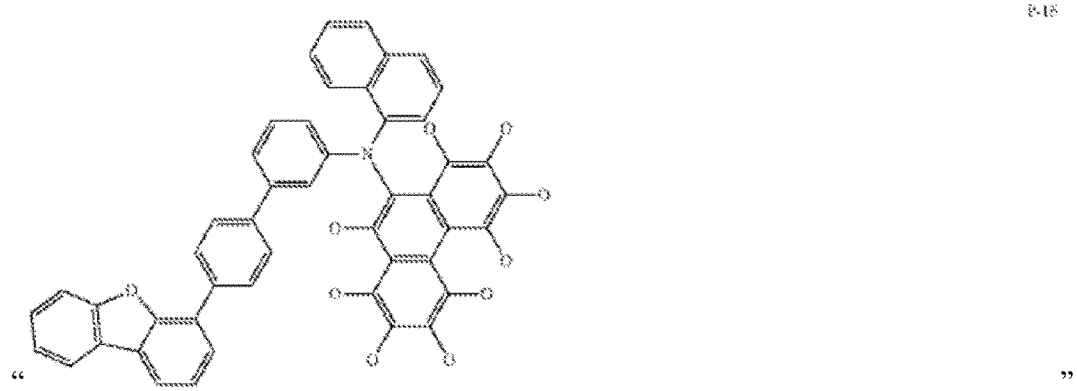

" "

And replace with:
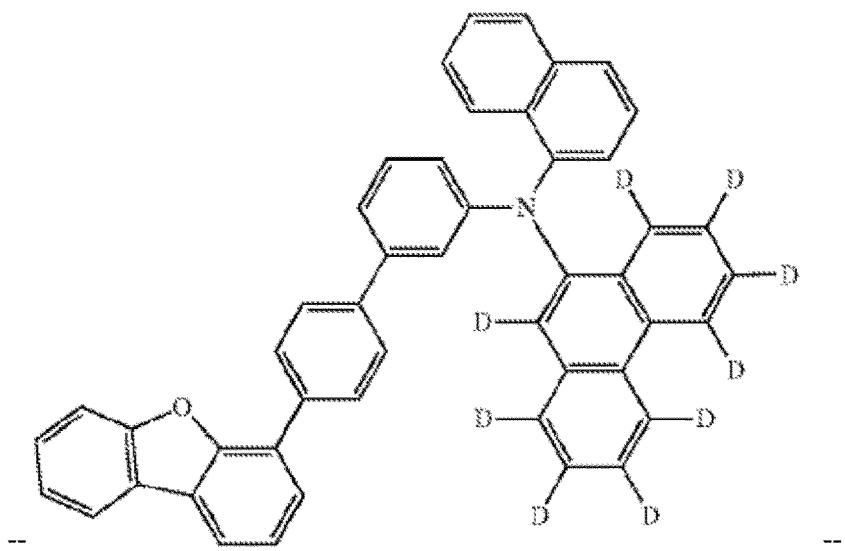
--                                                                                          --
Column 103, Claim 7, Formula P-18:
Please delete:
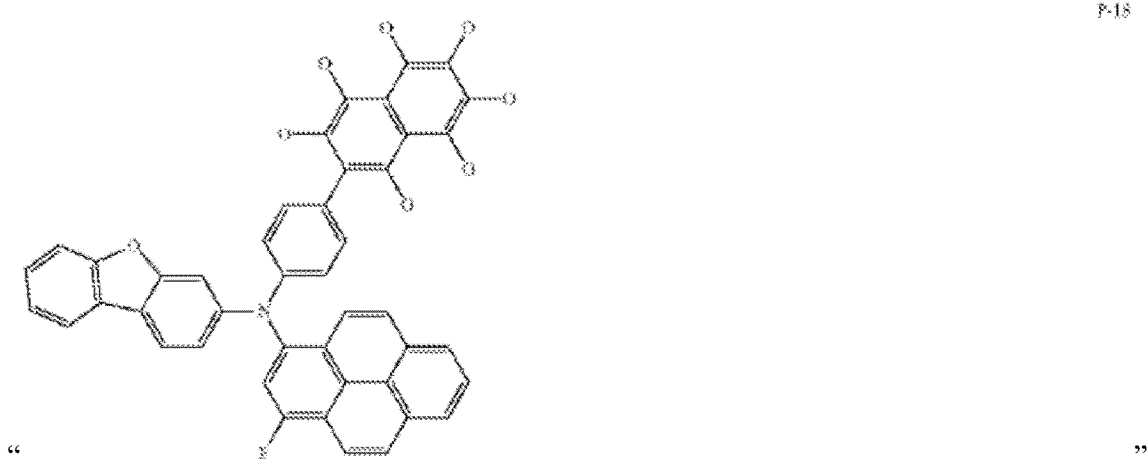
"                                                                                          "

And replace with:
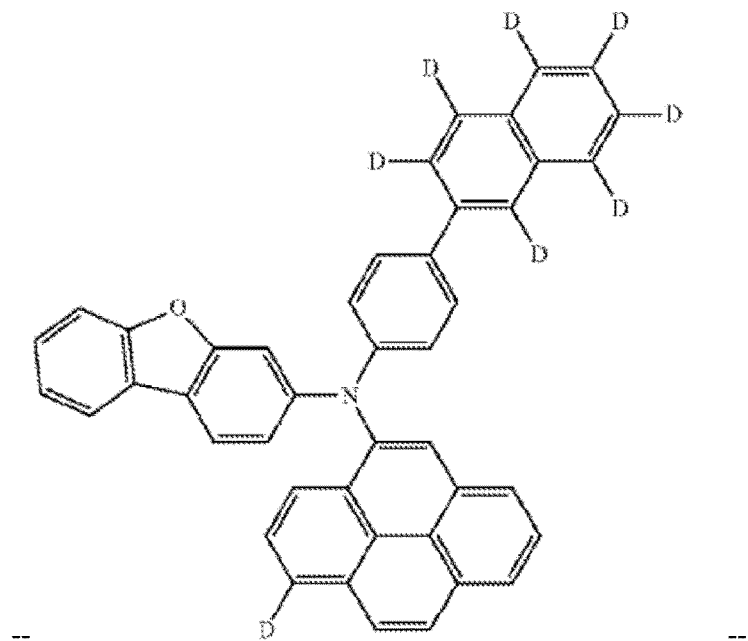
Column 105, Claim 7, Formula P-19:
Please delete:
"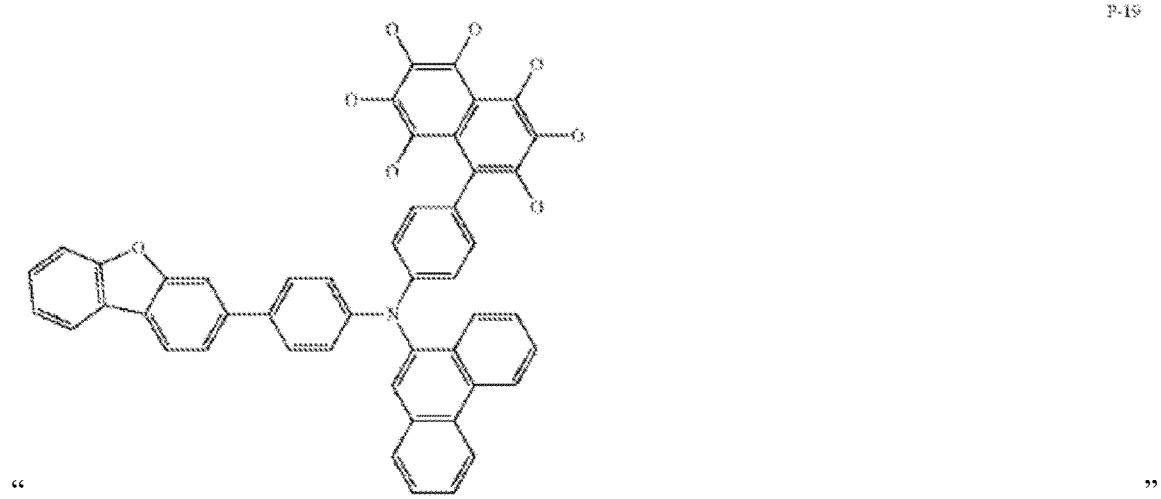"

And replace with:
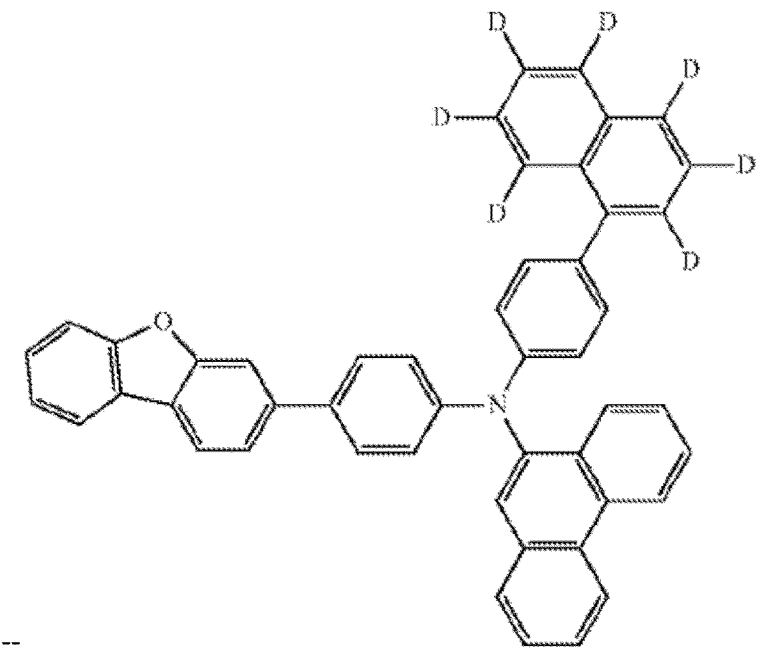
Column 105, Claim 7, Formula P-21:
Please delete:
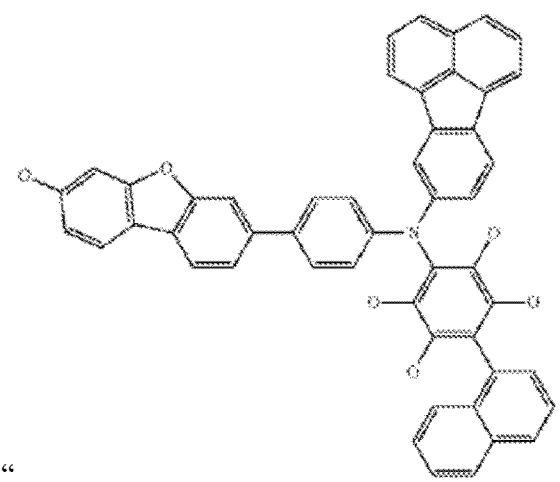
" "

CERTIFICATE OF CORRECTION (continued)
U.S. Pat. No. 11,196,008 B2

Page 8 of 22

And replace with:

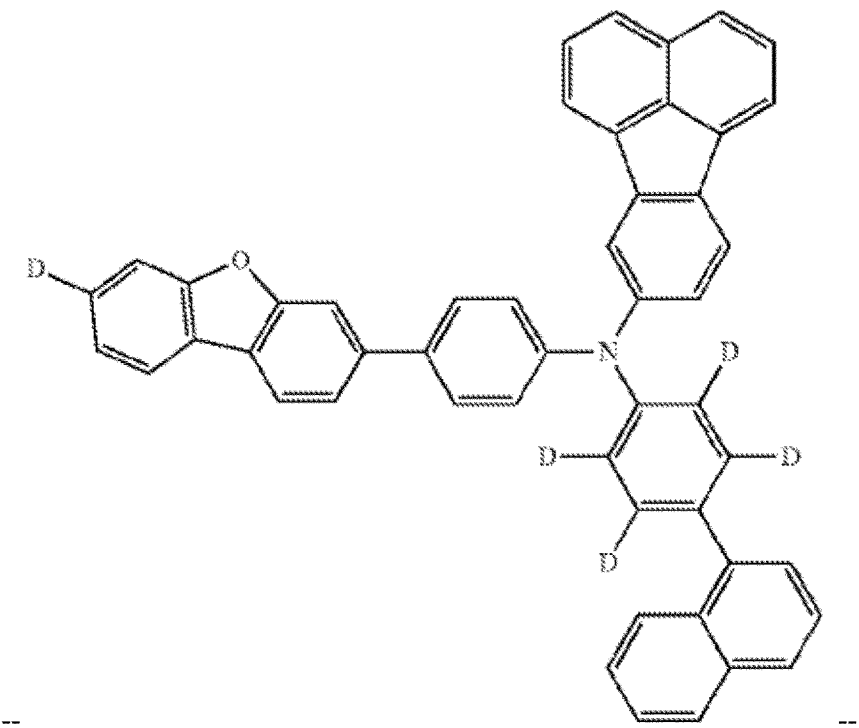

--                                                                    --

Column 105, Claim 7, Formula P-22:
Please delete:

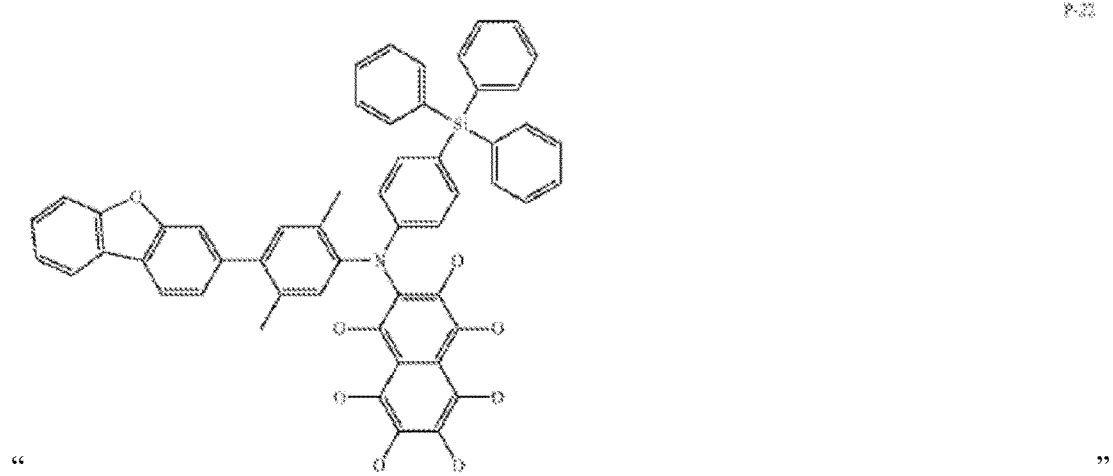

"                                                                     "

CERTIFICATE OF CORRECTION (continued)
U.S. Pat. No. 11,196,008 B2

And replace with:

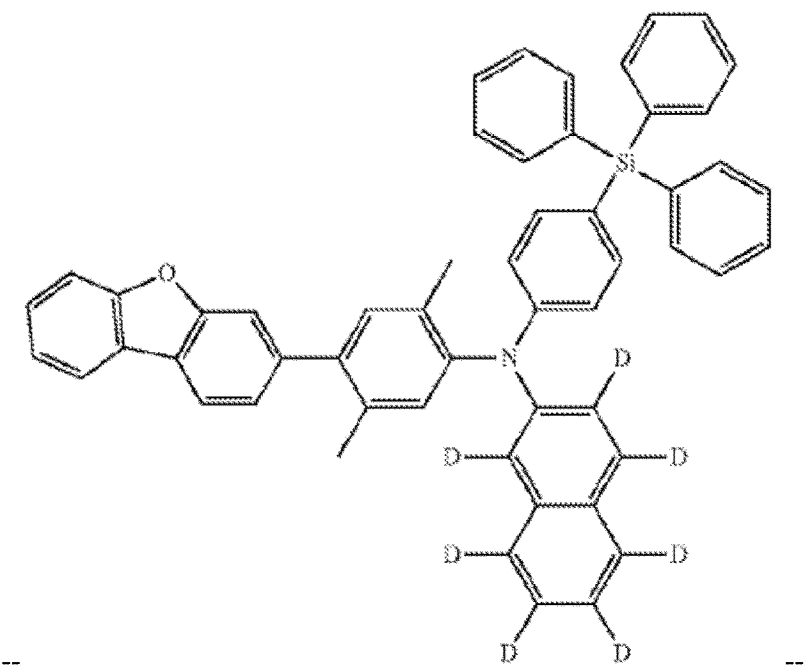

Column 107, Claim 7, Formula P-23:
Please delete:

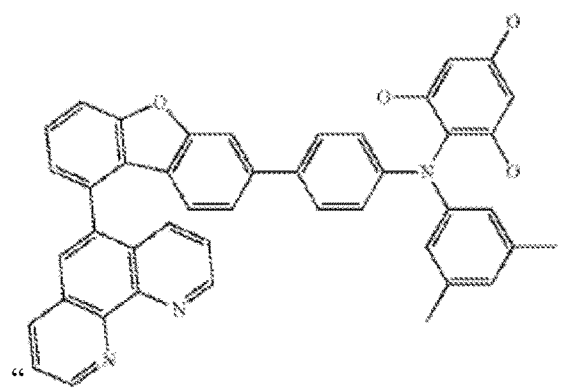

CERTIFICATE OF CORRECTION (continued)
U.S. Pat. No. 11,196,008 B2

And replace with:

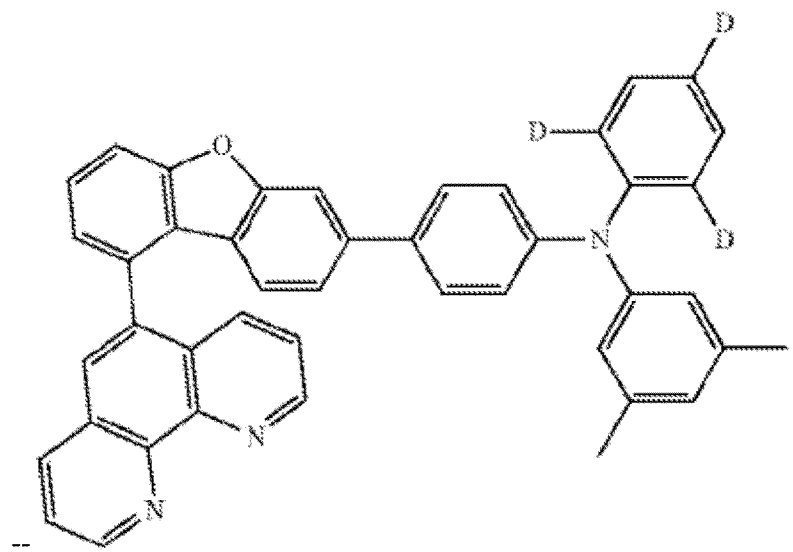

Column 107, Claim 7, Formula P-26:
Please delete:

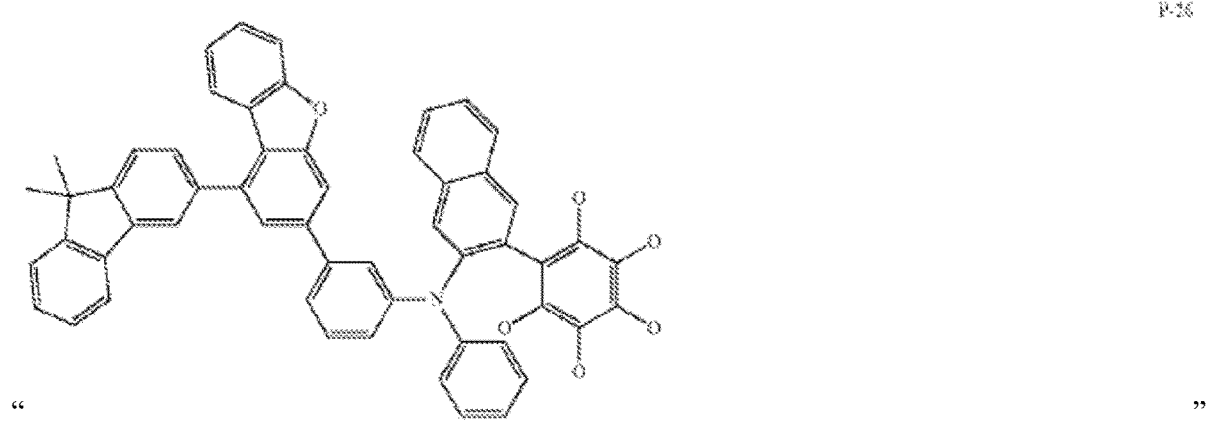

And replace with:
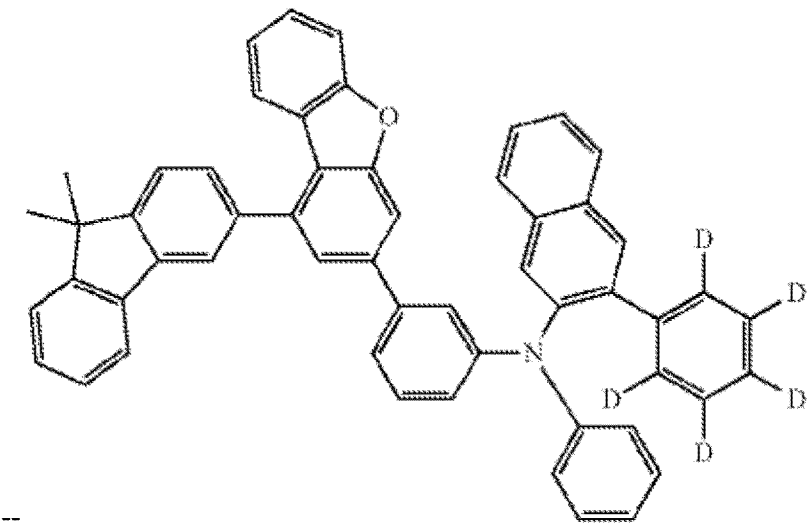
--  --
Column 107, Claim 7, Formula P-27:
Please delete:
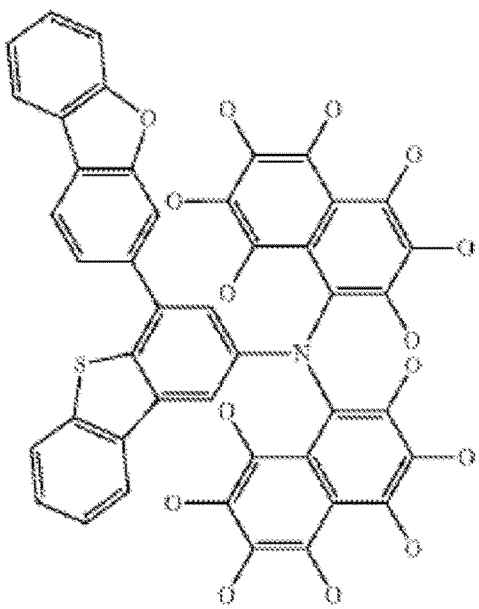
"  "

And replace with:
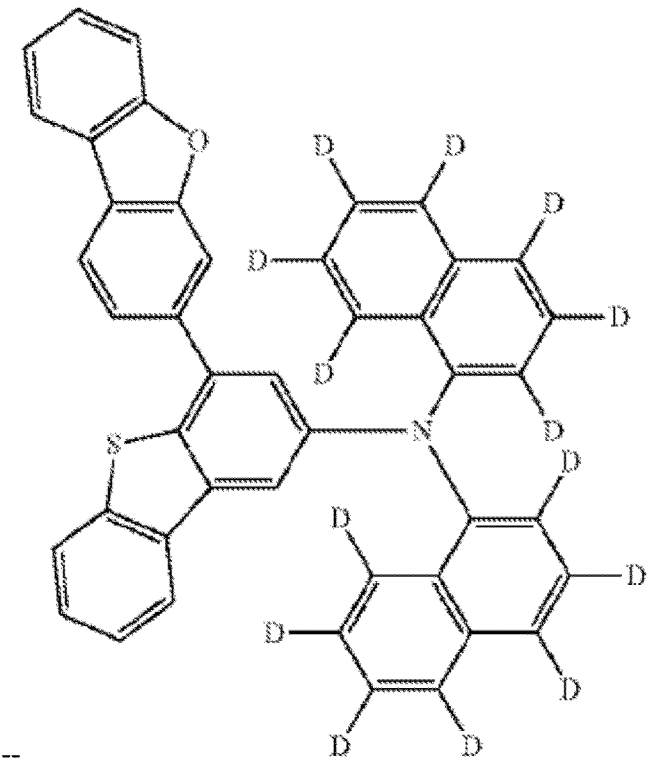
Column 108, Claim 7, Formula P-31:
Please delete:
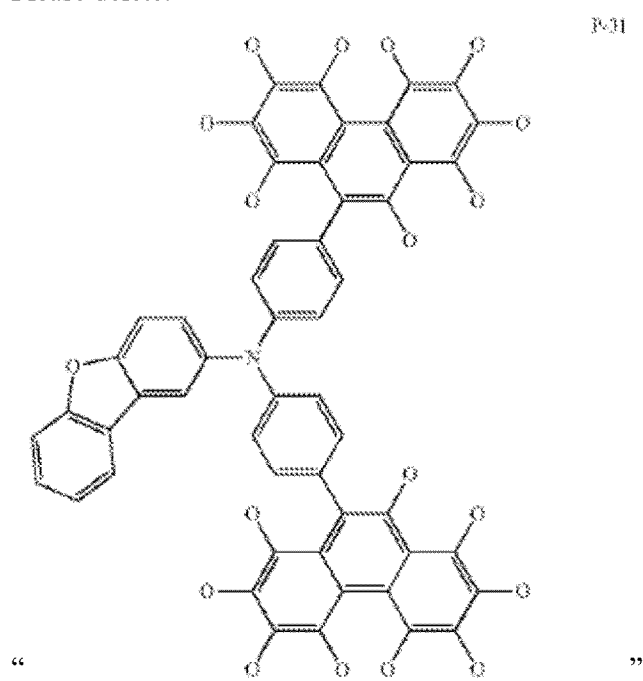

CERTIFICATE OF CORRECTION (continued)
U.S. Pat. No. 11,196,008 B2

Page 13 of 22

And replace with:

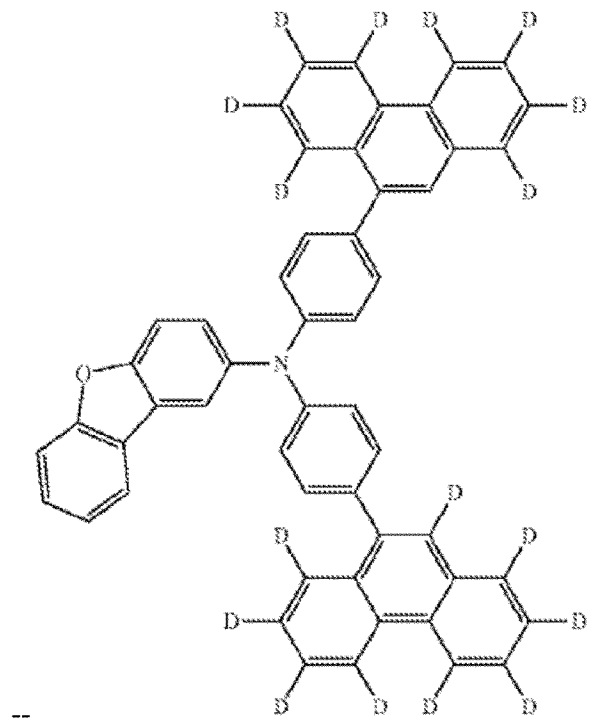

--                                                                              --

Column 109, Claim 7, Formula P-34:
Please delete:

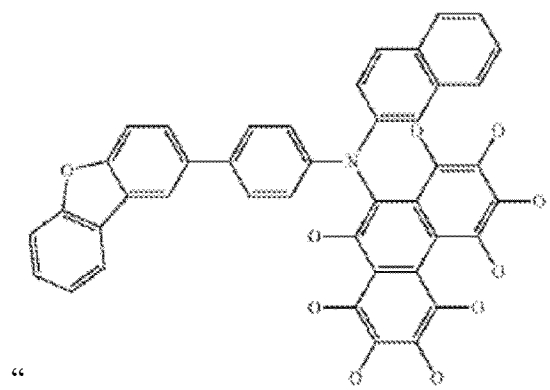

"                                                                              "

And replace with:
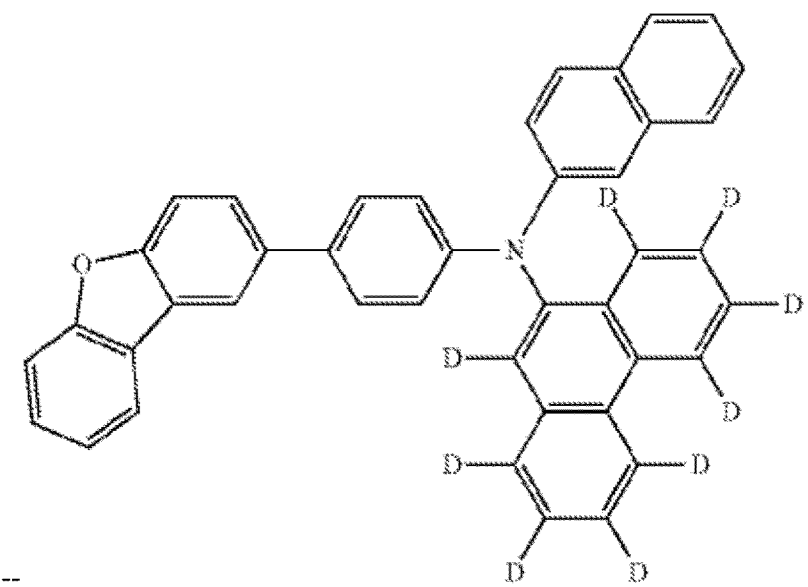
--        --
Column 109, Claim 7, Formula P-37:
Please delete:
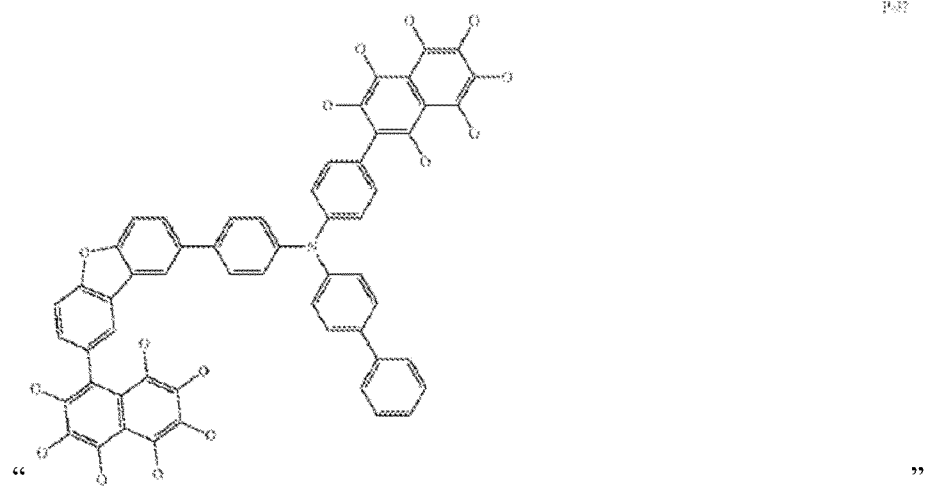
"        "

And replace with:
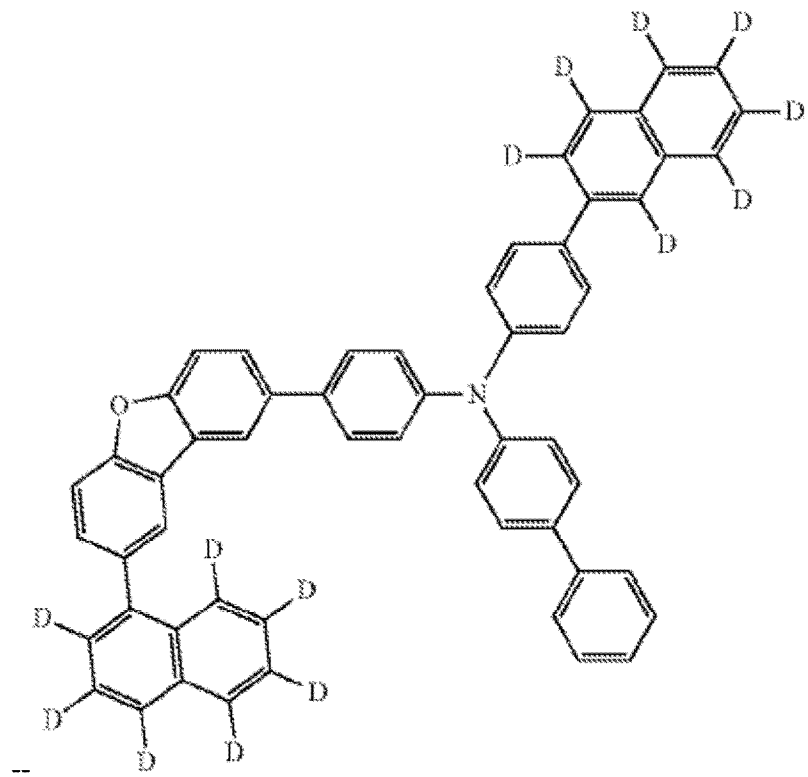
-- --
Column 109, Claim 7, Formula P-46:
Please delete:
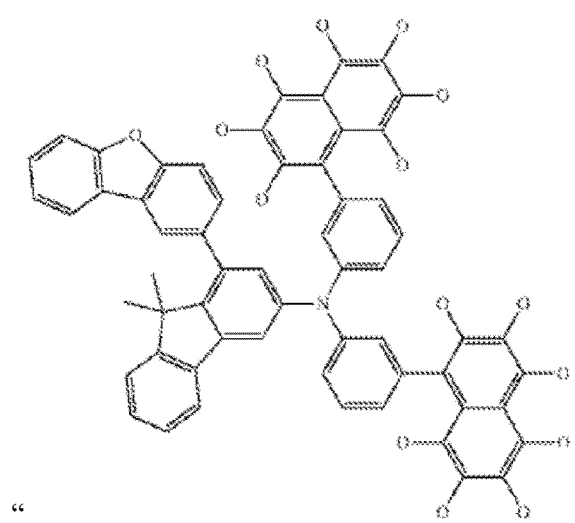
" "

And replace with:
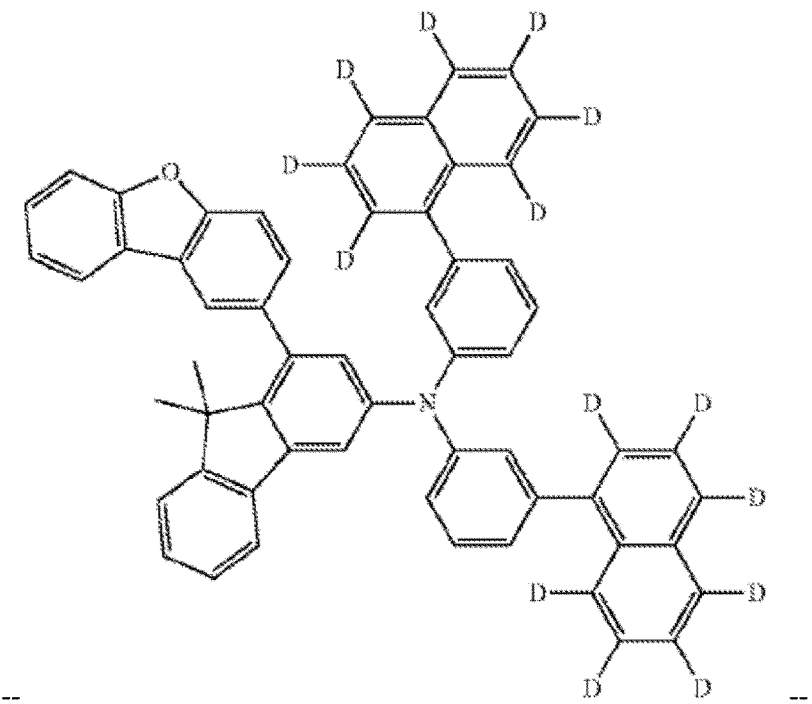
--                                                                    --
Column 111, Claim 7, Formula P-47:
Please delete:
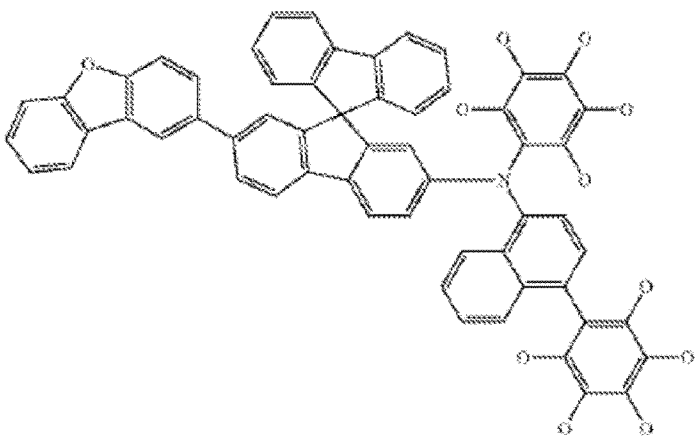
"                                                                    "

CERTIFICATE OF CORRECTION (continued)
U.S. Pat. No. 11,196,008 B2

And replace with:

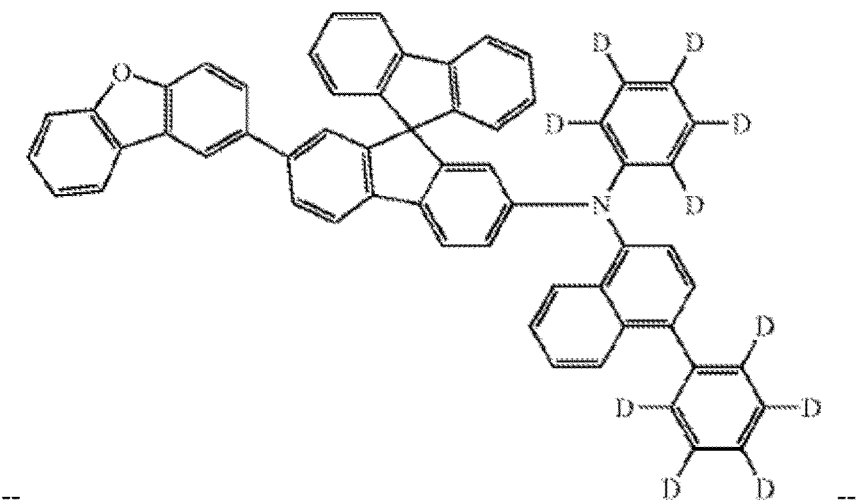

--

Column 111, Claim 7, Formula P-48:
Please delete:

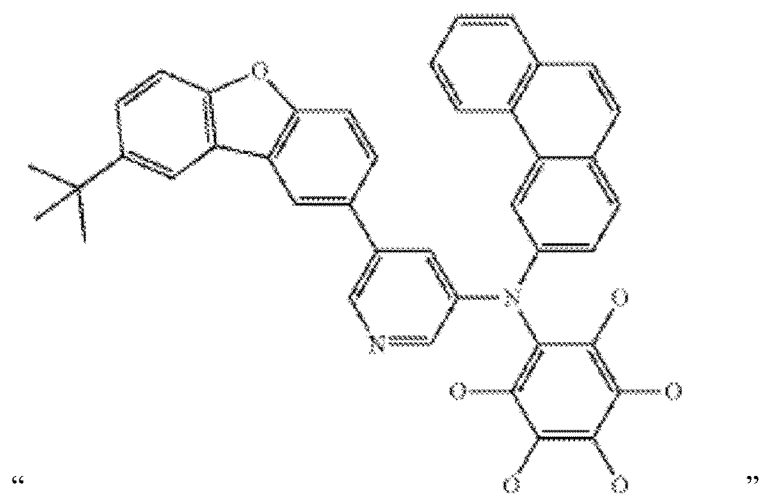

" "

And replace with:
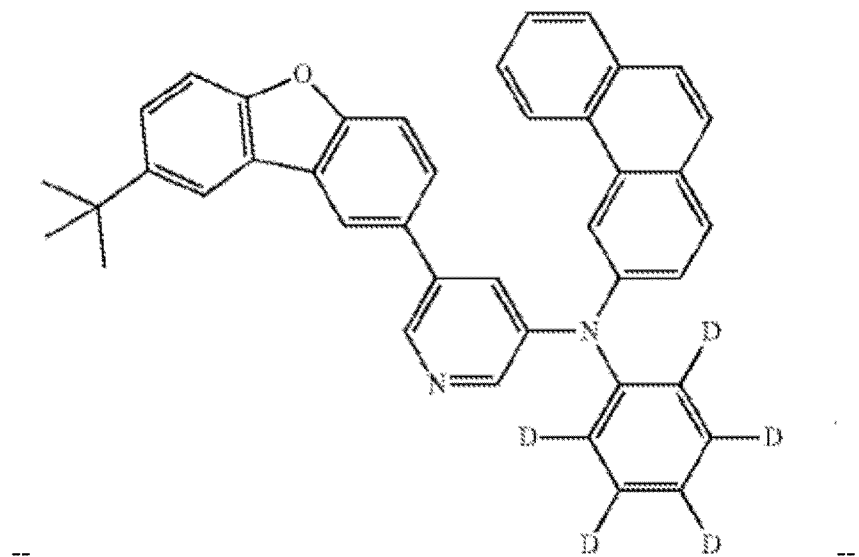
--
Column 112, Claim 7, Formula P-52:
Please delete:
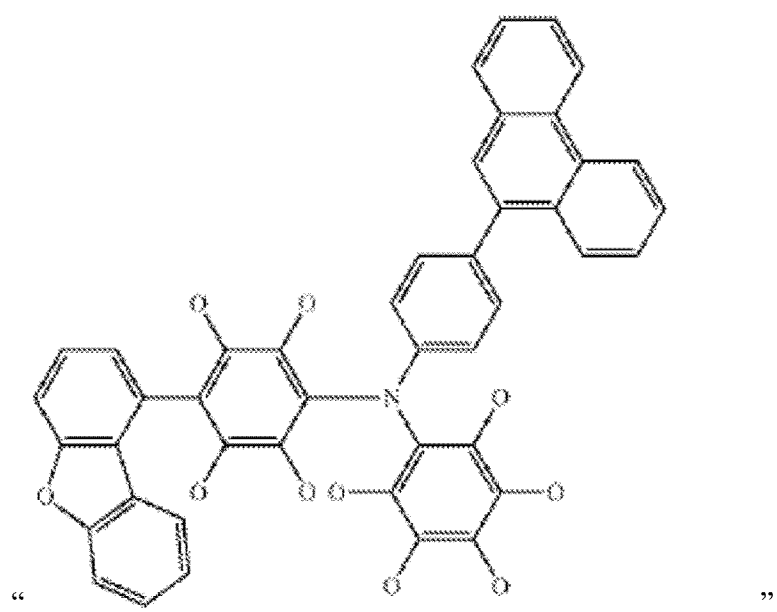
" "

CERTIFICATE OF CORRECTION (continued)
U.S. Pat. No. 11,196,008 B2

And replace with:

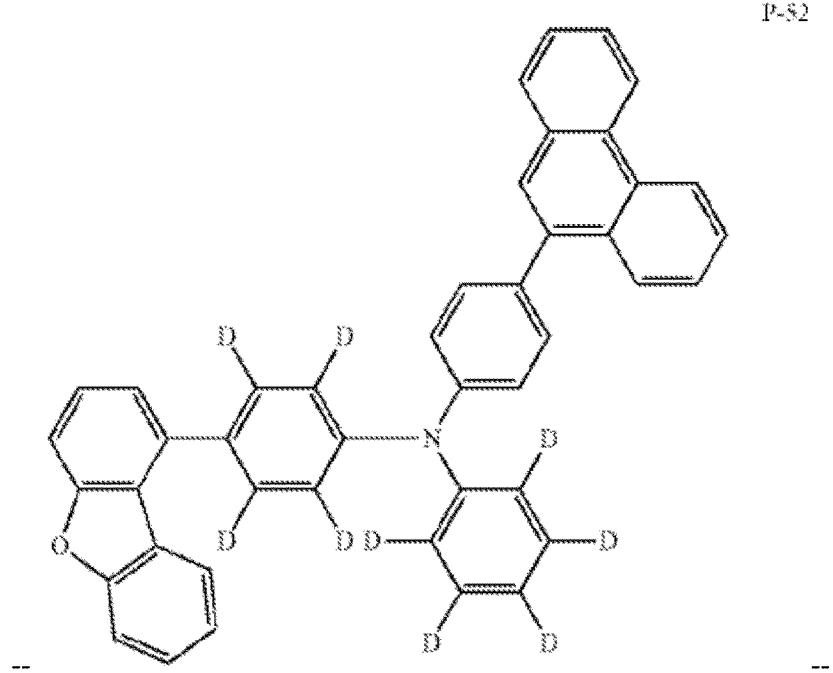

Column 112, Claim 7, Formula P-56:
Please delete:

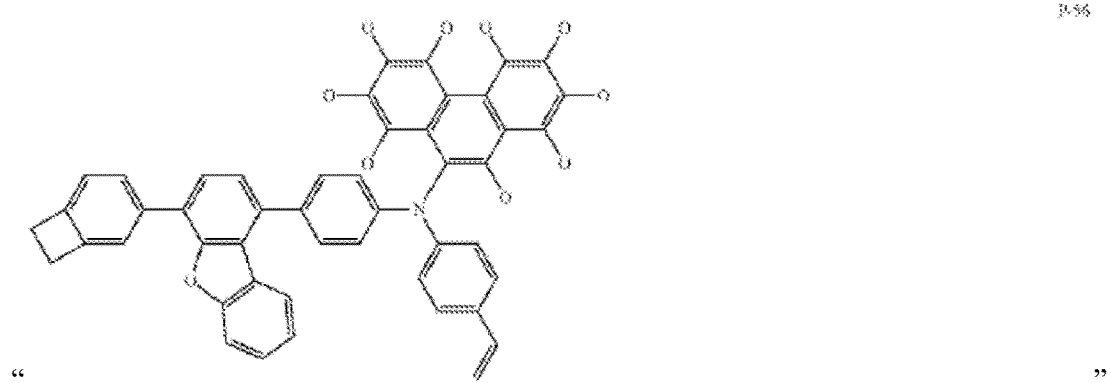

And replace with:

CERTIFICATE OF CORRECTION (continued)
U.S. Pat. No. 11,196,008 B2

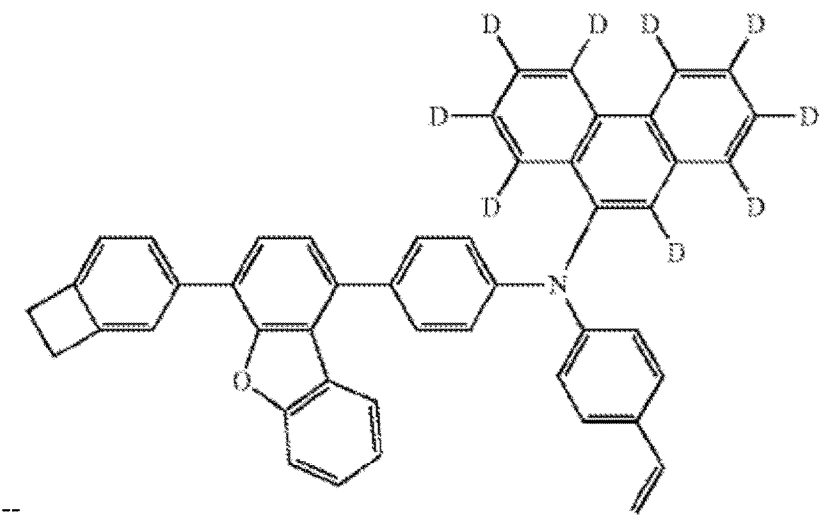

Column 113, Claim 7, Formula P-58:
Please delete:

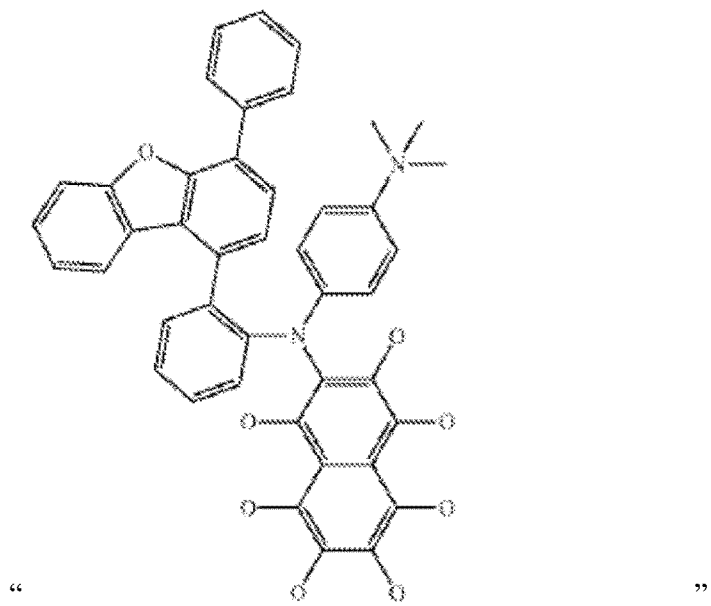

"                                                                                    "

And replace with:

CERTIFICATE OF CORRECTION (continued)
U.S. Pat. No. 11,196,008 B2

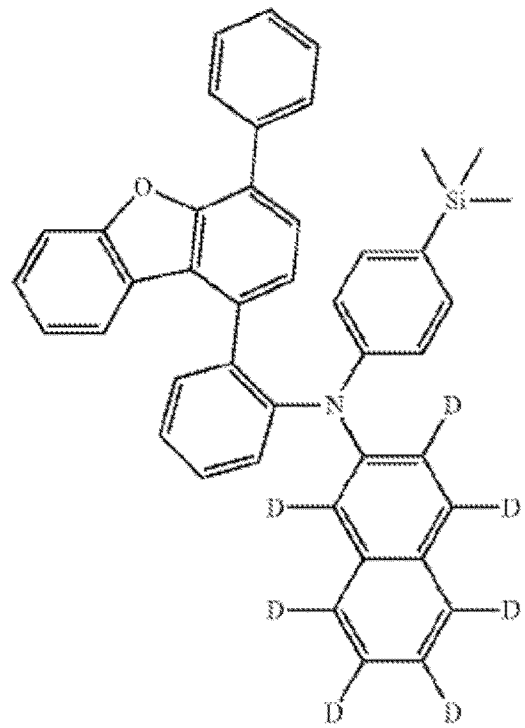

Column 114, Claim 7, Formula P-59:
Please delete:

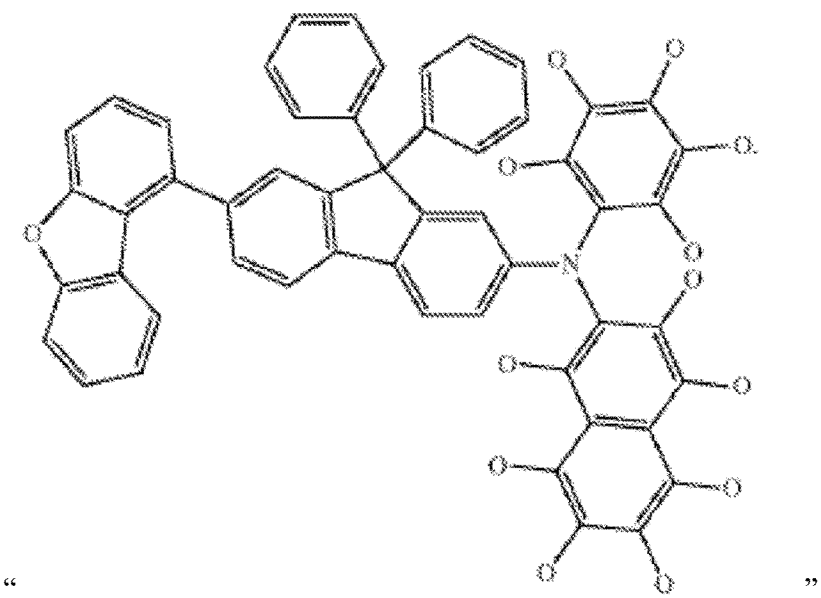

And replace with: